US012716890B2

(12) United States Patent
Traverso et al.

(10) Patent No.: US 12,716,890 B2
(45) Date of Patent: Aug. 25, 2026

(54) MACRO TISSUE EXPLANT, METHODS AND USES THEREFOR

(71) Applicants: Massachusetts Institute of Technology, Cambridge, MA (US); The Brigham and Women's Hospital, Inc., Boston, MA (US)

(72) Inventors: Carlo Giovanni Traverso, Newton, MA (US); Thomas Christian Von Erlach, Cambridge, MA (US); Robert S. Langer, Newton, MA (US); Sarah Saxton, Cambridge, MA (US); Daniel Minahan, Weymouth, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 18/936,294

(22) Filed: Nov. 4, 2024

(65) Prior Publication Data

US 2025/0060360 A1 Feb. 20, 2025

Related U.S. Application Data

(63) Continuation of application No. 15/934,029, filed on Mar. 23, 2018, now abandoned.

(60) Provisional application No. 62/560,485, filed on Sep. 19, 2017, provisional application No. 62/476,181, filed on Mar. 24, 2017.

(51) Int. Cl.

| | |
|---|---|
| ***G01N 33/50*** | (2006.01) |
| ***C12N 5/00*** | (2006.01) |
| ***C12N 5/071*** | (2010.01) |

(52) U.S. Cl.

CPC ....... *G01N 33/5088* (2013.01); *C12N 5/0062* (2013.01); *C12N 5/0679* (2013.01); *C12N 2503/02* (2013.01); *C12N 2503/04* (2013.01); *C12N 2510/00* (2013.01); *C12N 2513/00* (2013.01); *C12N 2531/00* (2013.01)

(58) Field of Classification Search

CPC .............. G01N 33/5088; C12N 5/0062; C12N 5/0679; C12N 2503/02; C12N 2503/04; C12N 2510/00; C12N 2513/00; C12N 2531/00

See application file for complete search history.

(56) References Cited

U.S. PATENT DOCUMENTS

| | | | | |
|---|---|---|---|---|
| 6,309,635 | B1 | 10/2001 | Ingber et al. | |
| 7,390,653 | B2 | 6/2008 | Akers et al. | |
| 8,298,822 | B2 | 10/2012 | Kruse et al. | |
| 8,642,339 | B2 | 2/2014 | Sato et al. | |
| 8,748,180 | B2 | 6/2014 | Shuler et al. | |
| 9,127,254 | B2 | 9/2015 | Cohen et al. | |
| 12,031,977 | B2 * | 7/2024 | Langer | C12N 5/0062 |
| 2010/0047853 | A1 | 2/2010 | Kuo et al. | |
| 2014/0302491 | A1 | 10/2014 | Nadauld et al. | |
| 2015/0329829 | A1 | 11/2015 | Shen et al. | |
| 2018/0002672 | A1 | 1/2018 | Allbritton et al. | |
| 2019/0064153 | A1 | 2/2019 | Traverso et al. | |
| 2023/0101335 | A1 * | 3/2023 | Traverso | G01N 33/5088 435/29 |

FOREIGN PATENT DOCUMENTS

| | | | |
|---|---|---|---|
| EP | 1896572 | A2 | 3/2008 |
| JP | 2013-9598 | A | 1/2013 |
| WO | 2002/061424 | A2 | 8/2002 |
| WO | 2003/053217 | A2 | 7/2003 |
| WO | 2005/009510 | A2 | 2/2005 |
| WO | 2009/132196 | A2 | 10/2009 |
| WO | 2014/069995 | A1 | 5/2014 |
| WO | 2014/082096 | A1 | 5/2014 |
| WO | 2016/123474 | A1 | 8/2016 |
| WO | 2018/175861 | A1 | 9/2018 |

OTHER PUBLICATIONS

Vadstrup et al. "Validation and optimization of an ex vivo assay of intestinal mucosal biopsies in Crohn's disease: Reflects inflammation and drug effects." PloS one 11.5 (2016): e0155335 (Year: 2016).*

Deiss et al. "Platform for high-throughput testing of the effect of soluble compounds on 3D cell cultures." Analytical chemistry 85.17 (2013): 8085-8094 (Year: 2013).*

Randall et al. "Explant culture of gastrointestinal tissue: a review of methods and applications." Cell biology and toxicology 27.4 (2011): 267-284 (Year: 2011).*

Applied Biosystems, MicroAmp 96-Well Tray, 2015 (Year: 2015).*

Assimakopoulos et al., Enterocytes' tight junctions: From molecules to diseases. World J Gastrointest Pathophysiolo.

Autrup et al., Explant culture of rat colon: a model system for studying metabolism of chemical carcinogens. In Vitro. Oct. 1978;14(10):868-77.

Costa et al., Development and evaluation of a porcine in vitro colon organ culture technique. In Vitro Cell Dev Biol Anim. Oct. 2016;52(9):942-952.

Dahlstrand et al., Nestin mRNA expression correlates with the central nervous system progenitor cell state in many, but not all, regions of developing central nervous system. Brain Res Dev Brain Res. Jan. 14, 1995;84(1):109-29.

Danielsen et al., Biosynthesis of intestinal microvillar proteins. Characterization of intestinal explants in organ culture and evidence for the existence of pro-forms of the microvillar enzymes. Biochem J. Mar. 15, 1982;202(3):647-54.

Daulagala et al., E-cadherin Beyond Structure: A Signaling Hub in Colon Homeostasis and Disease. Int J Mol Sci. Jun. 5, 2019;20(11):2756.

(Continued)

*Primary Examiner* — Alexander W Nicol

(74) *Attorney, Agent, or Firm* — McCarter & English, LLP; Jill Mello; Yelena Margolin

(57) ABSTRACT

Tissue explants of the gastrointestinal tract are provided. Methods of making and using the tissue explants are also provided, along with substrates designed for the tissue explants described.

28 Claims, 47 Drawing Sheets
(26 of 47 Drawing Sheet(s) Filed in Color)

(56) References Cited

OTHER PUBLICATIONS

Dedhia et al., Organoid Models of Human Gastrointestinal Development and Disease. Gastroenterology. May 2016;150(5):1098-1112.
Deward et al., Cellular heterogeneity in the mouse esophagus implicates the presence of a nonquiescent epithelial stem cell population. Cell Rep. Oct. 23, 2014;9(2):701-11.
Dimarco et al., Engineering of three-dimensional microenvironments to promote contractile behavior in primary intestinal organoids. Integr Biol (Camb). Feb. 2014;6(2):127-142.
Dimarco et al., Protein-engineered scaffolds for in vitro 3D culture of primary adult intestinal organoids. Biomater Sci. Oct. 15, 2015;3(10):1376-85.
Filimonova, Morphofunctional Characteristics Of Capillaries Endomysia Of The Tibilian Anterior Muscle During Distraction Osteosynthesis According To Ilizarov. International Journal of Applied and Basic Research. 2014;11(part 1):126-130.
Haslam et al., Pancreatoduodenectomy as a source of human small intestine for Ussing chamber investigations and comparative studies with rat tissue. Biopharm Drug Dispos. May 2011;32(4):210-21.
Kik et al., Pathological effects of Phaseolus vulgaris isolectins on pig jejunal mucosa in organ culture. Gut. Aug. 1991;32(8):886-92.
Kuratnik et al., Intestinal organoids as tissue surrogates for toxicological and pharmacological studies. Biochem Pharmacol. Jun. 15, 20135;85(12):1721-6.
Macartney et al., Primary murine small intestinal epithelial cells, maintained in long-term culture, are susceptible to rotavirus infection. J Virol. Jun. 2000;74(12):5597-603.
Markov et al., Physiology, Biochemistry, Biophysics, Protein Expression of Tight Junctions in Rat Colon Epithelium. Vestnik, Saint Petersburg University Bulletin. 2007, Serial 3, Publication 4, pp. 86-92.
Medema et al., Microenvironmental regulation of stem cells in intestinal homeostasis and cancer. Nature. Jun. 15, 2011;474(7351):318-26.
Mingaleeva et al., Application of cell and tissue cultures for potential anti-cancer/oncology drugs screening in vitro. Cell Transplantology and Tissue Engineering. 2013;VIII(2):20-28.
Ootani et al., Sustained in vitro intestinal epithelial culture within a Wnt-dependent stem cell niche. Nat Med. Jun. 2009;15(6):701-6.
Polentarutti et al., Evaluation of viability of excised rat intestinal segments in the Ussing chamber: investigation of morphology, electrical parameters, and permeability characteristics. Pharm Res. Mar. 1999;16(3):446-54.
Ranga et al., Drug discovery through stem cell-based organoid models. Adv Drug Deliv Rev. Apr. 2014;69-70:19-28.
Rozehnal et al., Human small intestinal and colonic tissue mounted in the Ussing chamber as a tool for characterizing the intestinal absorption of drugs. Eur J Pharm Sci. Aug. 15, 2012;46(5):367-73.
Sakolish et al., Modeling Barrier Tissues In Vitro: Methods, Achievements, and Challenges. EBioMedicine. Feb. 13, 2016;5:30-9.
Sato et al., Long-term expansion of epithelial organoids from human colon, adenoma, adenocarcinoma, and Barrett's epithelium. Gastroenterology. Nov. 2011;141(5):1762-72.
Shah et al., A microfluidics-based in vitro model of the gastrointestinal human-microbe interface. Nat Commun. May 11, 2016;7:11535, 15 pages.
Shamir et al., Three-dimensional organotypic culture: experimental models of mammalian biology and disease. Nat Rev Mol Cell Biol. Oct. 2014;15(10):647-64.
Silva-Adaya et al., Thioredoxin system regulation in the central nervous system: experimental models and clinical evidence. Oxid Med Cell Longev. 2014;2014:590808.
Sjoberg et al., Comprehensive study on regional human intestinal permeability and prediction of fraction absorbed of drugs using the Ussing chamber technique. Eur J Pharm Sci. Jan. 23, 2013;48(1-2):166-80.
Thorn et al., Cytochromes P450 and MDR1 mRNA expression along the human gastrointestinal tract. Br J Clin Pharmacol. Jul. 2005;60(1):54-60.
Tsilingiri et al., Probiotic and postbiotic activity in health and disease: comparison on a novel polarised ex-vivo organ culture model. Gut. Jul. 2012;61(7):1007-15.
Verhovskaya et al., Alkoxy-substituted glycerol effect on morphofunctional characteristics of a passaged culture. Cryobiology, pp. 30-34, (1990).
Von Erlach et al., Robotically handled whole-tissue culture system for the screening of oral drug formulations. Nat Biomed Eng. May 2020;4(5):544-559.
Wang et al., A microengineered collagen scaffold for generating a polarized crypt-villus architecture of human small intestinal epithelium. Biomaterials. Jun. 2017;128:44-55.
Invitation to Pay Additional Fees for Application No. PCT/US2018/023982, dated Jun. 8, 2018, 15 pages.
International Search Report and Written Opinion for Application No. PCT/US2018/023982, dated Jul. 31, 2018, 17 pages.
International Preliminary Report on Patentability for Application No. PCT/US2018/023982, dated Oct. 3, 2019, 12 pages.
Tham et al., Expression of extracellular glutathione peroxidase in human and mouse gastrointestinal tract. Am J Physiol. Dec. 1998;275(6): G1463-71.

* cited by examiner 0 days 2 days 7 days 3 weeks 4 weeks

T7d T0

Lysozyme
Claudin-1
R-spondin-1
Nestin
Keratin
E-cadherin
OLFM4
LGR5
Vimentin
CDX2
FABP
GLP-1
Villin
MDR-1
BCRP
MAT1
OCT1
SNAC2
PEPT1
OST-α

0 days 7 days

LGR-5
MUC-2
Nestin
OLFM-4
Villin
KRT20
FABP-1

CDX-2
SYP
Wnt3a
R-Sp
ABCC3
PepT-1
MDR-1

MRP-2
ZO-2
MCT-1
BCRP
OCT-1
OST-α
GLP-1
GIP

Claudin-1
Claudin-4
Claudin-8
Lysozyme-1
CYP3A4

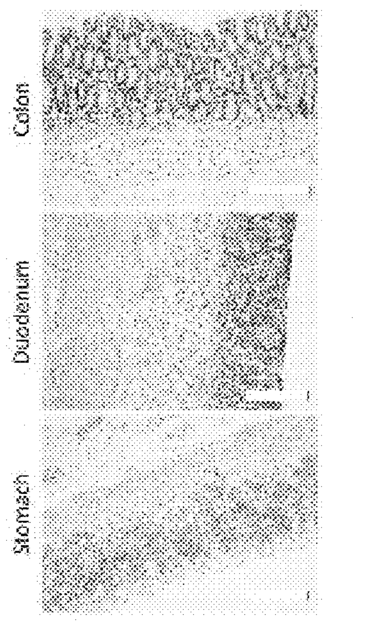
FIG. 2J
FIG. 2K
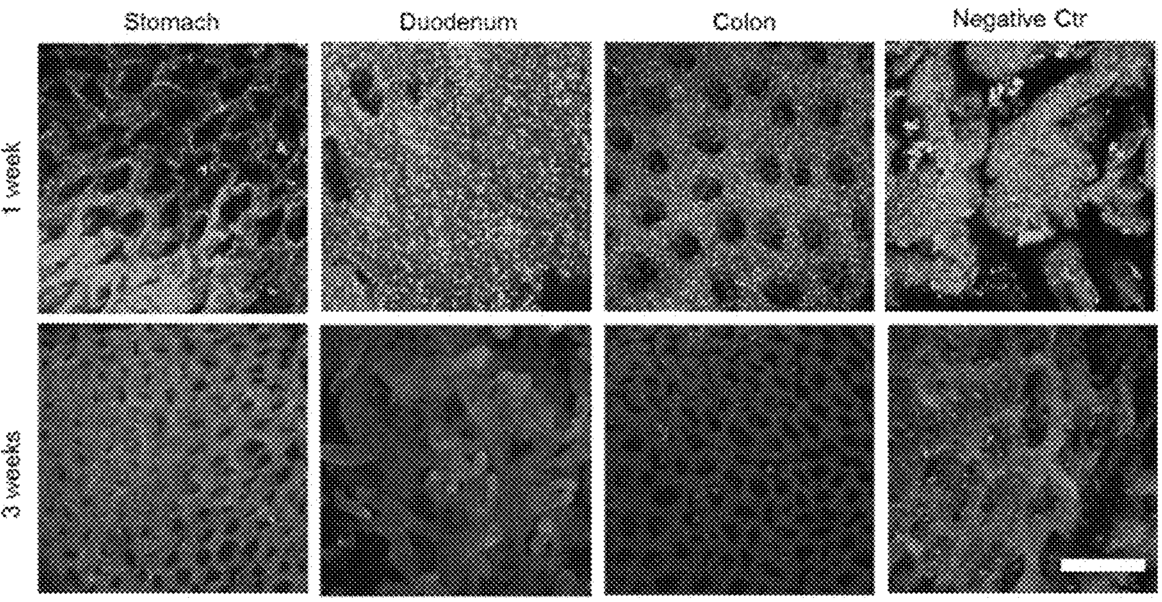

Slow Absorption

Moderate Absorption

Fast Absorption

H28-MTX-E1

C2BBe1

GI Tissue Explant

MACRO TISSUE EXPLANT, METHODS AND USES THEREFOR

RELATED APPLICATIONS

This application is a continuation of U.S. application Ser. No. 15/934,029, filed on Mar. 23, 2018; which claims the benefit of U.S. Provisional Application Ser. No. 62/476,181, filed on Mar. 24, 2017; and U.S. Provisional Application Ser. No. 62/560,485, filed on Sep. 19, 2017. The entire contents of the above-referenced applications are incorporated herein by this reference.

BACKGROUND

Mammalian organs are challenging to study as they are fairly inaccessible to experimental manipulation and optical observation. Recent advances in three-dimensional (3D) culture techniques, coupled with the ability to independently manipulate genetic and microenvironmental factors, have enabled the real-time study of mammalian tissues.

However, these systems fail to fully recapitulate the architecture and functionality of a tissue. Furthermore, these cultures are generally incompatible with high-throughput systems. Therefore, a need remains for systems that can mimic the in vivo architecture and function of a tissue and be subjected to high-throughput experimental testing.

SUMMARY OF DISCLOSURE

The present disclosure is based, in part, on the discovery that tissue explants derived from the gastrointestinal tract can be utilized in high-throughput screening assays for at least drug absorption, drug dissolution, drug-induced gastrointestinal toxicity, and endocrine system modulation. For example, that dissection of the small intestine of a porcine can be manipulated for utilization in a high-throughput system, wherein absorption of a drug can be measured by perfusion.

Accordingly, in some aspects, the disclosure relates to an in vitro cellular composition comprising:

(i) a substrate comprising a plurality of microwells; and (ii) a tissue explant comprising intestinal epithelium from a large, non-human, mammalian gastrointestinal tract, wherein the intestinal epithelium comprises epithelial cells having a polarity in the tissue explant, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects the disclosure relates to an in vitro cellular composition comprising:

(i) a substrate comprising a plurality of microwells; and (ii) a tissue explant comprising intestinal epithelium from a human gastrointestinal tract, wherein the intestinal epithelium comprises epithelial cells having a polarity in the tissue explant, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects of the disclosure, the tissue explant described herein comprises small intestine epithelium, circular muscular layer and intestinal villi. In further aspects of the disclosure, the tissue explant described herein is derived from the ileum of the gastrointestinal tract. In other aspects of the disclosure, the tissue explant described herein is derived from the jejunum of the gastrointestinal tract. In further aspects of the disclosure, the tissue explant described herein is derived from the stomach, duodenum, esophagus, buccal, lingual or colon of the gastrointestinal tract.

In some aspects of the disclosure, the tissue explant described herein comprises a fully intact extracellular matrix. In further aspects of the disclosure, the fully intact extracellular matrix comprises lamina propria. In yet further aspects of the disclosure, the fully intact extracellular matrix comprises lamina muscularis.

In another aspect of the disclosure, the tissue explant described herein is derived from a porcine gastrointestinal tract. In further aspects of the disclosure, the tissue explant described herein forms a mucus layer in culture. In yet further aspects of the disclosure, the tissue explant described herein is maintained in culture for at least 24 hours, 2 days, 3 days, 1 week, 2 weeks, 3 weeks, 4 weeks or more.

In some aspects of the disclosure, the tissue explant described herein does not require an exogenous growth factor to be maintained in culture. In further aspects of the disclosure, the exogenous growth factor is Wnt3a.

In further aspects of the disclosure, the tissue explant described herein is derived after the mammal has been bled.

In some aspects of the disclosure, the tissue explant described herein comprises intestinal enterocytes. In further aspects of the disclosure, intestinal enterocytes are identified by the presence of villin, e-cadherin, keratin 20, and/or fatty acid binding protein 1 (FABP1). In some aspects of the disclosure, the tissue explant described herein comprises tight junctions. In some aspects, tight junctions are identified by the presence of Claudin-1.

In further aspects of the disclosure, the tissue explant described herein comprises mucin secreting goblet cells. In some aspects of the disclosure, mucin secreting goblet cells are identified by the presence of mucin 2 (Muc2) and/or caudal type homeobox 2 (CDX2).

In other aspects of the disclosure, the tissue explant described herein comprises intestinal stem cells. In some aspects of the disclosure, intestinal stem cells are identified by the presence of leucine-rich repeat-containing G-protein coupled receptor 5 (LGR5) and/or olfactomedin 4 (OLFM4).

In further aspects of the disclosure, the tissue explant described herein comprises intestinal endocrine cells. In some embodiments, intestinal endocrine cells are neuroendocrine cells (L-cells). In some aspects of the disclosure, intestinal endocrine cells are identified by the presence of glucagon-like peptide-1 (GLP-1).

In some aspects of the disclosure, the tissue explant described herein comprises at least one drug transporter. In further aspects of the disclosure, the drug transporter is MDR-1. In some aspects, the drug transporter is selected from the group consisting of: MDR-1, ABCC3, MRP-2, PEPT-1, BCRP, OCT-1, OST-α and MCT-1.

In yet further aspects of the disclosure, the tissue explant described herein comprises at least one metabolizing enzyme. In some aspects of the disclosure, the metabolizing enzyme is CYP3A4.

In some aspects of the disclosure, the tissue explant described herein comprises microfold cells. In further aspects of the disclosure, microfold cells are identified by the presence of vimentin.

In some aspects of the disclosure, the tissue explant described herein comprises mucosubstances. In further aspects of the disclosure, the mucosubstances are glycoproteins, glycolipids or mucins.

In further aspects of the disclosure, the tissue explant described herein comprises neural cells. In some aspects of the disclosure, neural cells are identified by the presence of nestin.

In yet further aspects of the disclosure, the tissue explant described herein mimics in vivo architecture of the gastrointestinal tract from which it was derived. In some aspects of the disclosure, the tissue explant described herein maintains a constant level of secreted Wnt3a. In further aspects of the disclosure, the level of secreted Wnt3a is determined by western blot analysis.

In some aspects of the disclosure, the tissue explant described herein comprises intact crypts. In further aspects of the disclosure, the tissue explant described herein comprises thioredoxin reductase activity. In yet further aspects of the disclosure thioredoxin reductase activity is maintained for at least 7 days. In some aspects of the disclosure, the tissue explant comprises cytochrome P450 3A4 (CYP3A4) activity. In yet furthers aspects of the disclosure, CYP3A4 activity is maintained for at least 7 days. In some aspects of the disclosure, the tissue explant comprises uridine 5'-diphospho glucuronosyltransferase (UGT) activity.

In further aspects of the disclosure, the tissue explant described herein is derived from a large non-human mammal at least 3 weeks in age. In some aspects of the disclosure, the large non-human mammal is between 3 weeks and 12 weeks of age.

In some aspects of the disclosure, the tissue explant described herein produces GLP-1 or Muc-2. In some aspects of the disclosure, the tissue explant produces GLP-1. In further aspects of the disclosure, the tissue explant described herein is responsive to glucose.

In yet further aspects of the disclosure, the tissue explant described herein is responsive to toxins. In some aspects, the tissue explant described herein recovers from exposure to toxins. In some aspects of the disclosure, the toxin is a substance with gastrointestinal toxicity or a substance with cell toxicity. In further aspects of the disclosure, the toxin is a nonsteroidal anti-inflammatory drug (NSAID). In yet further aspects of the disclosure, the NSAID is naproxen. In some aspects of the disclosure, the toxin is doxycycline. In some aspects of the disclosure, the toxin is selected from the group consisting of: antibiotics, NSAIDs, bisphosphonates, bronchodilators, antivirals, vasodilators, diuretics, and proton pump inhibitors. In some aspects, the toxin is an antibiotic, wherein the antibiotic is cefpodoxime or doxycycline. In some aspects, the toxin is an NSAID, wherein the NSAID is selected from the group consisting of: meloxicam, mesalamine, naproxen and indomethacin. In some aspects, the toxin is a bisphosphonate, wherein the bisphosphonate is etidronate. In some aspects, the toxin is a bronchodilator, wherein the bronchodilator is theophylline. In some aspects, the toxin is an antiviral, wherein the antiviral is enofovir or oseltamivir. In some aspects, the toxin is a vasodilator, wherein the vasodilator is tadalafil. In some aspects, the toxin is a diuretic, wherein the diuretic is amiloride. In some aspects, the toxin is a proton pump inhibitor, wherein the proton pump inhibitor is omeprazole.

In some aspects, the tissue explant described herein comprises: (a) intestinal epithelium from a large, non-human, mammalian gastrointestinal tract, wherein the intestinal epithelium comprises epithelial cells having a polarity in the tissue explant; and (b) small intestine epithelium, circular muscular layer and intestinal villi.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix comprising lamina propria.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix comprising lamina muscularis.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix comprising lamina propria and lamina muscularis.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix, wherein the tissue explant forms a mucus layer in culture.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix, wherein the tissue explant is maintained in culture for 24 hours, 2 days, 3 days, 1 week, 2 weeks, 3 weeks, 4 weeks or more.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix, wherein the tissue explant is maintained in culture for 24 hours, 2 days, 3 days, 1 week, 2 weeks, 3 weeks, 4 weeks or more, and wherein the tissue explant forms a mucus layer in culture.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix, wherein the tissue explant is maintained in culture for 24 hours, 2 days, 3 days, 1 week, 2 weeks, 3 weeks, 4 weeks or more, and wherein the tissue explant does not require an exogenous growth factor to be maintained in culture.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix, wherein the tissue explant mimics in vivo architecture of the gastrointestinal tract from which it was derived.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; (c) a fully intact extracellular matrix; and (d) intact crypts.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; (c) a fully intact extracellular matrix; and (d) intact crypts, wherein the tissue explant mimics in vivo architecture of the gastrointestinal tract from which it was derived.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix, wherein the tissue explant is responsive to glucose.

In some aspects, the tissue explant described herein comprises: (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix, wherein the tissue explant is responsive to toxins.

In some aspects of the disclosure, the substrate described herein comprises 6, 12, 24, 48, 96, 384 or 1536 microwells. In further aspects of the disclosure, each microwell is completely covered by the tissue explant. In some aspects of the disclosure, the substrate does not comprise exogenous extracellular matrix. In yet further aspects of the disclosure, blood content of the tissue explant has been minimized.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) small intestine epithelium, circular muscular layer and intestinal villi, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) a fully intact extracellular matrix, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) a fully intact extracellular matrix comprising lamina propria, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) a fully intact extracellular matrix comprising lamina muscularis, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) a fully intact extracellular matrix comprising lamina propria and lamina muscularis, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix comprising lamina propria, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix comprising lamina muscularis, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix comprising lamina propria and lamina muscularis, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising intestinal epithelium from a large, non-human, mammalian gastrointestinal tract, wherein the intestinal epithelium comprises epithelial cells having a polarity in the tissue explant, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) small intestine epithelium, circular muscular layer and intestinal villi, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) a fully intact extracellular matrix, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) a fully intact extracellular matrix comprising lamina propria, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) a fully intact extracellular matrix comprising lamina muscularis, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) a fully intact extracellular matrix comprising lamina propria and lamina muscularis, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and
(ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and
(ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix comprising lamina propria, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and
(ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix comprising lamina muscularis, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and
(ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) a fully intact extracellular matrix comprising lamina propria and lamina muscularis, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and
(ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) at least one drug transporter, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and
(ii) a tissue explant comprising (a) intestinal epithelium from a large, non-human, mammalian gastrointestinal tract, wherein the intestinal epithelium comprises epithelial cells having a polarity in the tissue explant; (b) a fully intact extracellular matrix; (c) at least one drug transporter, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and
(ii) a tissue explant comprising (a) intestinal epithelium from a large, non-human, mammalian gastrointestinal tract, wherein the intestinal epithelium comprises epithelial cells having a polarity in the tissue explant; (b) a fully intact extracellular matrix comprising lamina propria; and (c) at least one drug transporter, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and
(ii) a tissue explant comprising (a) intestinal epithelium from a large, non-human, mammalian gastrointestinal tract, wherein the intestinal epithelium comprises epithelial cells having a polarity in the tissue explant; (b) a fully intact extracellular matrix comprising lamina muscularis; and (c) at least one drug transporter, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) a fully intact extracellular matrix comprising lamina propria and lamina muscularis; and (c) at least one drug transporter, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; (c) a fully intact extracellular matrix; and (d) at least one drug transporter, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; (c) a fully intact extracellular matrix comprising lamina propria; and (d) at least one drug transporter, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; (c) a fully intact extracellular matrix comprising lamina muscularis; and (d) at least one drug transporter, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; (c) a fully intact extracellular matrix comprising lamina propria and lamina muscularis; and (d) at least one drug transporter, wherein the tissue explant is in planar contact with the substrate, thereby providing a luminal surface and a basolateral surface of the in vitro cellular composition, and wherein the polarity of the epithelial cells is maintained in the in vitro cellular composition.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; and (b) at least one drug transporter, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; and (c) at least one drug transporter, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) a fully intact extracellular matrix; and (c) at least one drug transporter, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) a fully intact extracellular matrix comprising lamina propria; and (c) at least one drug transporter, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) a fully intact extracellular matrix comprising lamina muscularis; and (c) at least one drug transporter, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) a fully intact extracellular matrix comprising lamina propria and lamina muscularis; and (c) at least one drug transporter, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; (c) a fully intact extracellular matrix; and (d) at least one drug transporter, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; (c) a fully intact extracellular matrix comprising lamina propria; and (d) at least one drug transporter, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; (c) a fully intact extracellular matrix comprising lamina muscularis; and (d) at least one drug transporter, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

In some aspects, the disclosure relates to an in vitro cellular composition comprising:

(i) a substrate comprising a plurality of microwells; and (ii) a tissue explant comprising (a) intestinal epithelium from a large, non-human, mammalian gastrointestinal tract, wherein the intestinal epithelium comprises epithelial cells having a polarity in the tissue explant; (b) small intestine epithelium, circular muscular layer and intestinal villi; (c) a fully intact extracellular matrix comprising lamina propria and lamina muscularis; and (d) at least one drug transporter, wherein the tissue explant is in planar contact with the substrate, thereby providing a luminal surface and a basolateral surface of the in vitro cellular composition, wherein the polarity of the epithelial cells is maintained in the in vitro cellular composition, and wherein the tissue explant does not require an exogenous growth factor to be maintained in culture.

The disclosure also provides a cell culture system for use in a high-throughput drug absorption screening assay, wherein the cell culture system comprises:

(i) a substrate comprising a plurality of microwells; and (ii) a tissue explant comprising intestinal epithelium from a large, non-human, mammalian gastrointestinal tract, wherein the intestinal epithelium comprises epithelial cells having a polarity in the tissue explant, wherein the tissue explant is in planar contact with the substrate, thereby providing a luminal surface and a basolateral surface, and wherein the polarity of the epithelial cells is maintained in the cell culture system, thereby allowing measurement of absorption of a drug through the tissue explant. In some aspects of the disclosure, the tissue explant described herein comprises intestinal epithelium from human gastrointestinal tract.

In other aspects, the disclosure provides a high-throughput system comprising (i) a substrate comprising a plurality of microwells; and (ii) a tissue explant comprising intestinal epithelium from a large, non-human, mammalian gastrointestinal tract, wherein the intestinal epithelium comprises epithelial cells having a polarity in the tissue explant, wherein the tissue explant is in planar contact with the substrate, thereby providing a luminal surface and a basolateral surface, and wherein the polarity of the epithelial cells is maintained in the system. In some aspects of the disclosure, the tissue explant described herein comprises intestinal epithelium from human gastrointestinal tract.

The disclosure also provides methods for determining absorption of a test compound through a gastrointestinal tissue explant, comprising:

(a) contacting a tissue explant with a test compound, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant; and (b) determining absorption by detecting the presence of the test compound at the luminal surface and at the basolateral surface, wherein presence of the test compound at the basolateral surface indicates the ability of the compound to be absorbed through the tissue explant. In some aspects, detecting the presence of the test compound comprises determining concentration of the compound at the luminal and basolateral surfaces. In some aspects of the disclosure, the tissue explant described herein comprises intestinal epithelium from human gastrointestinal tract.

In some aspects, absorption through the tissue explant has a higher Pearson correlation value when compared to absorption measured in vivo, relative to the Pearson correlation value for absorption determined using Caco-2 cells. In some aspects, the higher Pearson correlation value is at least 0.70, at least 0.75, at least 0.80, at least 0.85 or at least 0.90. In some aspects, absorption through the tissue explant has a lower coefficient of variation (CV) relative to absorption determined using Caco-2 cells.

In yet further aspects, the disclosure provides methods for determining concentration of a test compound in a gastrointestinal tissue explant, comprising:

(a) contacting a tissue explant with a compound of interest, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant; and (b) detecting the presence of the compound within the tissue explant. In some aspects, determining concentration of the compound comprises high content confocal analysis. In some aspects of the disclosure, the tissue explant described herein comprises intestinal epithelium from human gastrointestinal tract.

In further aspects, the disclosure provides methods for determining oral bioavailability of a test compound through a gastrointestinal tissue explant, comprising:

(a) contacting a tissue explant with a compound of interest, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant; and (b) detecting the presence of the compound at the luminal surface and at the basolateral surface, wherein presence of the compound at the basolateral surface indicates the oral bioavailability of the compound. In some aspects of the disclosure, the tissue explant described herein comprises intestinal epithelium from human gastrointestinal tract.

In some aspects, the disclosure provides methods for predicting absorption of a test compound through the human gastrointestinal tract, comprising:

(a) contacting a tissue explant with a compound of interest, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant; and (b) predicting absorption by detecting the presence of the compound at the luminal surface and at the basolateral surface, wherein presence of the compound at the basolateral surface indicates ability of the compound to be absorbed through the human gastrointestinal tract. In some aspects of the disclosure, the tissue explant described herein comprises intestinal epithelium from human gastrointestinal tract.

In yet further aspects, the disclosure provides methods for determining the effect of drug-food interactions on absorption of a test compound in a tissue explant, comprising:

(a) contacting a tissue explant with a compound of interest, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant;

(b) contacting the tissue explant with digested food; and (c) determining absorption by detecting the presence of the compound at the luminal surface and at the basolateral surface, wherein presence of the compound at the basolateral surface indicates ability of the compound to be absorbed through the tissue explant. In some aspects of the disclosure, the method further comprises contacting the tissue explant with native intestinal media derived from the large, non-human mammalian gastrointestinal tract. In some aspects of the disclosure, the tissue explant described herein comprises intestinal epithelium from human gastrointestinal tract. In further aspects of the disclosure, the compound of interest is solubilized in native intestinal media prior to contacting the tissue explant with the compound of interest. In some aspects of the disclosure, contacting the tissue explant with the digested food and compound of interest is simultaneous. In other aspects of the disclosure, the method further comprises determining the difference in absorption between a compound of interest in the presence or absence of the digested food.

In some aspects, the disclosure provides methods for time lapse analysis of absorption of a test compound through a gastrointestinal tissue explant, comprising:

(a) contacting a tissue explant with a compound of interest, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant; and (b) determining absorption over a time period, comprising detecting the presence of the compound at the luminal surface and at the basolateral surface at different time points, wherein presence of the compound at the basolateral surface indicates ability of the compound to be absorbed through the tissue explant. In some aspects of the disclosure, the tissue explant described herein comprises intestinal epithelium from human gastrointestinal tract.

In further aspects, the disclosure provides methods for determining the perfusion rate of a test compound through a tissue explant, comprising:

(a) contacting a tissue explant with a compound of interest, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant; and (b) determining perfusion over a time period, comprising detecting the presence of the compound at the luminal surface and at the basolateral surface at different time points, wherein presence of the compound at the basolateral surface indicates ability of the compound to be perfused through the tissue explant. In some aspects of the disclosure, the tissue explant described herein comprises intestinal epithelium from human gastrointestinal tract.

In further aspects, the disclosure provides methods for determining the effect of a test compound on a gastrointestinal tissue explant, comprising:

(a) conducting a first assay on a tissue explant, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant;

(b) contacting the tissue explant with a compound of interest;

(c) conducting a second assay on the tissue explant; and (d) comparing the results of the first assay and the second assay, thereby determining the effect of the compound. In some aspects of the disclosure, the tissue explant described herein comprises intestinal epithelium from human gastrointestinal tract. In some aspects of the disclosure, the first and second assays measure the effect of the compound on cytotoxicity of the gastrointestinal tract. In further aspects of the disclosure, the first and second assays measure the effect of the compound on metabolism of the gastrointestinal tract.

In some aspects, the disclosure provides methods for determining the effect of a drug transporter on absorption of a test compound through a tissue explant, comprising:

(a) modifying expression of the drug transporter in a tissue explant, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant;

(b) contacting the tissue explant with a compound of interest;

(c) determining absorption by detecting the presence of the compound at the luminal surface and at the basolateral surface, wherein presence of the compound at the basolateral surface indicates ability of the compound to be absorbed through the tissue explant; and (d) comparing absorption between the tissue explant with or without a modified drug transporter, thereby determining the effect of the drug transporter on absorption of the compound. In some aspects of the disclosure, the tissue explant described herein comprises intestinal epithelium from human gastrointestinal tract.

In yet further aspects, the disclosure provides methods for determining the effect of a metabolizing enzyme on absorption of a compound through the human gastrointestinal tract, comprising:

(a) modifying expression of the metabolizing enzyme in a tissue explant, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant;

(b) contacting the tissue explant with a compound of interest;

(c) determining absorption by detecting the presence of the compound at the luminal surface and at the basolateral surface, wherein presence of the compound at the basolateral surface indicates ability of the compound to be absorbed through the tissue explant; and (d) comparing absorption between the tissue explant with or without a modified metabolizing enzyme, thereby determining the effect of the drug transporter on absorption of the compound. In some aspects of the disclosure, the tissue explant described herein comprises intestinal epithelium from human gastrointestinal tract.

In some aspects of the disclosure, modifying expression comprises genetic modification. In further aspects of the disclosure, genetic modification comprises siRNA knockdown.

In further aspects, the disclosure provides methods for high-throughput drug screening, comprising contacting a tissue explant with a library of compounds, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant; and determining an effect of the library of compounds on the tissue explant. In some aspects of the disclosure, the tissue explant described herein comprises intestinal epithelium from human gastrointestinal tract.

In some aspects, the disclosure provides high-throughput methods for analyzing absorption of a drug formulation, comprising;

(a) contacting a tissue explant with a formulation library comprising a compound of interest and an excipient, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant;

(b) measuring absorption of the compound of interest through the tissue explant by detecting the presence of the compound at the luminal surface and at the basolateral surface, wherein presence of the compound at the basolateral surface indicates ability of the compound to be absorbed through the tissue explant;

(c) comparing absorption of the compound of interest with each formulation, thereby identifying a formulation for drug absorption. In some aspects of the disclosure, the tissue explant described herein comprises intestinal epithelium from human gastrointestinal tract.

In further aspects, the disclosure provides high-throughput drug absorption screening methods in which a plurality of drug compositions are simultaneously assayed for absorption, comprising:

(a) contacting a tissue explant with a plurality of drug compositions comprising a compound of interest and an excipient at different locations on the tissue explant, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant;

(b) measuring absorption of the compound of interest through the tissue explant by detecting the presence of the compound at the luminal surface and at the basolateral surface, wherein presence of the compound at the basolateral surface indicates ability of the compound to be absorbed through the tissue explant. In some aspects of the disclosure, the tissue explant described herein comprises intestinal epithelium from human gastrointestinal tract.

In yet further aspects, the disclosure provides methods of making an in vitro intestinal model, comprising:

(a) providing a tissue explant, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant; and (b) contacting the tissue explant with a substrate comprising a plurality of microwells. In some aspects of the disclosure, the tissue explant described herein comprises intestinal epithelium from human gastrointestinal tract.

In some aspects, the disclosure provides a substrate assembly suitable for use with a tissue explant, comprising:

a first plate having a main body having a plurality of microwells formed therein and having a plurality of fastener receiving apertures formed therein, a second plate having a main body and having a plurality of microwells formed therein and having a plurality of fastener receiving apertures formed therein, and a plurality of magnets, wherein one or said plurality of magnets is seated within each of the plurality of fastener receiving apertures of the first and second plates. In some aspects, the first plate has a top surface and an opposed bottom surface, wherein the bottom surface has a rim portion formed thereon about a peripheral edge of the bottom surface and extending outwardly therefrom, wherein the rim portion forms a chamber. In further aspects, the substrate assembly further comprises a ridge portion formed along a central portion of the bottom surface of the first plate and extending outwardly therefrom, wherein the ridge portion divides the chamber into a plurality of subchambers, each subchamber adapted to seat a tissue explant. In yet further aspects, the rim portion has formed therein along opposed sides of the main body of the first plate one or more cut-out features. In some aspects, the second plate has a top surface and an opposed bottom surface, wherein the top surface has a rim portion formed thereon about a peripheral edge of the top surface and extending outwardly therefrom, wherein the rim portion forms a chamber.

In some aspects, the substrate assembly further comprises a ridge portion formed along a central portion of the top surface of the second plate and extending outwardly therefrom, wherein the ridge portion divides the chamber into a plurality of subchambers, each subchamber adapted to seat a tissue explant. In some aspects the rim portion formed on the top surface of the second plate has formed therein along opposed sides of the main body of the top plate one or more cut-out features.

In any of the foregoing aspects of the substrate assembly, the plurality of microwells of the first plate and the second plate comprise 6, 12, 24, 28, 96, 384 or 1536 microwells. In some aspects, each microwell of the plurality of microwells is completely covered by a tissue explant.

In some aspects, the disclosure provides methods for determining absorption and dissolution of a test compound simultaneously within a gastrointestinal tract explant, comprising:

(a) dissolving a test compound in a solvent, thereby producing a drug solution, and allowing the drug solution to evaporate over a sufficient period of time to generate a resulting drug powder;

(b) combining the drug powder from (a) with an excipient;

(c) contacting a tissue explant with the drug powder from (b), wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant;

(d) determining dissolution by detecting the concentration in supernatant; and (e) determining absorption by detecting the presence of the test compound at the luminal surface and at the basolateral surface, wherein presence of the test compound at the basolateral surface indicates the ability of the compound to be absorbed through the tissue explant.

In further aspects, the disclosure provides methods for determining the effect of tissue accumulation of a test compound on a gastrointestinal tissue explant, comprising:

(a) conducting at least one first assay on a tissue explant, wherein the tissue explant comprises intestinal epithelium from a large, non-human, mammalian gastrointestinal tract, wherein the intestinal epithelium comprises epithelial cells having a polarity in the tissue explant, wherein the tissue explant provides a luminal surface and a basolateral surface, and wherein the polarity of the epithelial cells is maintained in the tissue explant;

(b) contacting the tissue explant with a compound of interest;

(c) conducting at least one second assay on the tissue explant; and (d) comparing the results of the first assay and the second assay, wherein the first and second assay are the same assay, thereby determining the effect of tissue accumulation of the compound.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 2J provides images of colon, duodenum and stomach tissue stained with hematoxylin and eosin (H&E). Scale bar=400 µm.

FIG. 2K provides images of LiveDead analysis of tissue explants from stomach, duodenum or colon cultured for 1 or 3 weeks ex vivo. Scale bar=200 µm.

DETAILED DESCRIPTION

Definitions

Figure 1A:
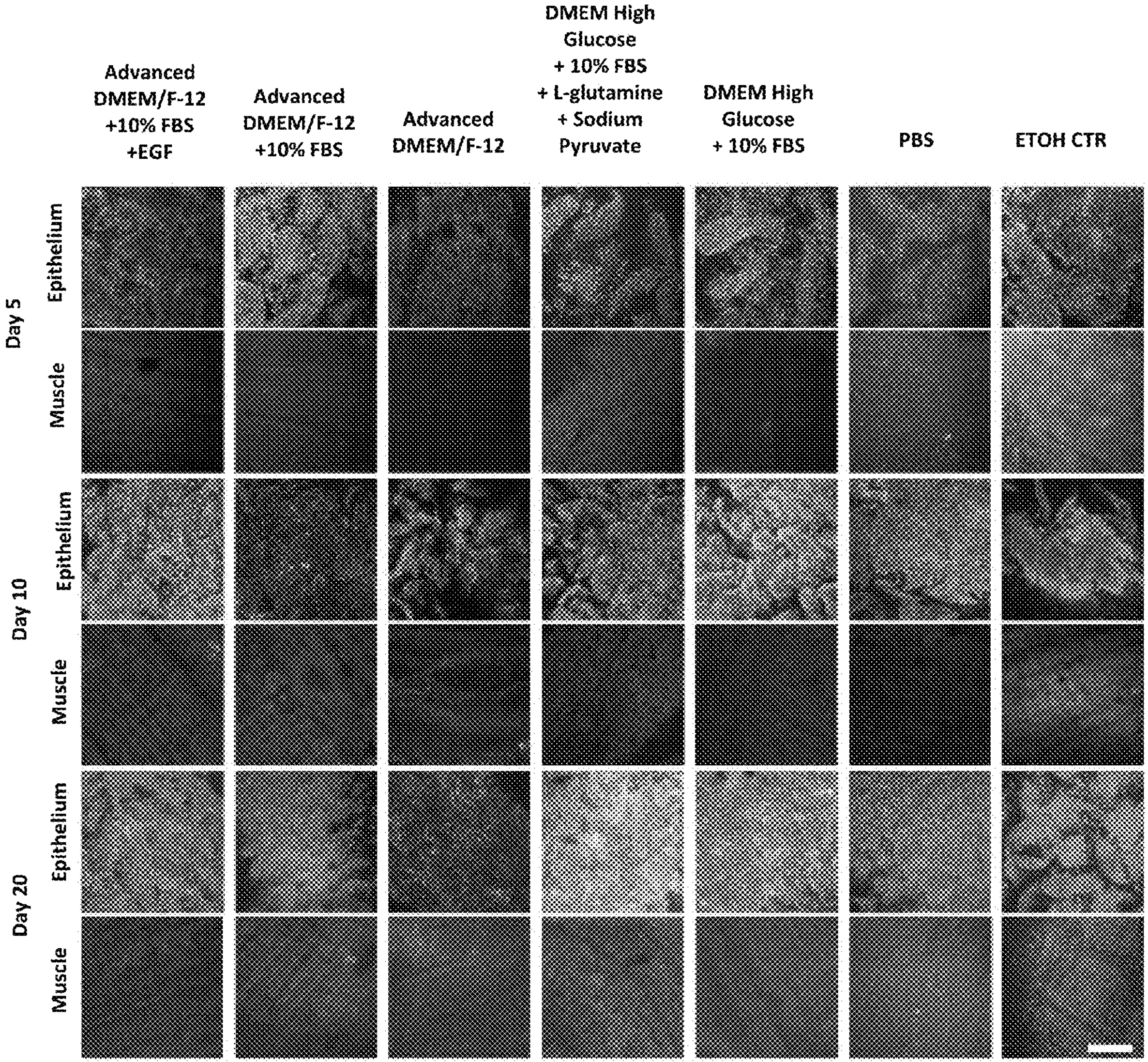
FIG. 1A provides images of LiveDead analysis of small intestinal tissue explants cultured in different media compositions for 5, 10 and 20 days ex vivo. Scale bar=200 µm.

Terms used in the claims and specification are defined as set forth below unless otherwise specified.

It must be noted that, as used in the specification and the claims, the singular forms "a," "an," and "the" include plural referents unless the context clearly dictates otherwise.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

As used herein, "architecture" refers to a tissue structure including the specific cell types within the tissue and the extracellular matrix surrounding the cells. In some embodiments, an in vitro cellular composition of the disclosure comprises a tissue explant comprising intestinal epithelium from a large, non-human, mammalian gastrointestinal tract or a human gastrointestinal tract, wherein the intestinal epithelium comprises epithelial cells having a polarity in the tissue explant and the in vitro cellular composition described herein substantially maintains all or a substantial portion of the source architecture (e.g., the in vivo architecture) of the tissue from which it was derived (e.g., small intestine). For example, when the tissue explant comprises intestinal epithelium comprising epithelial cells having a polarity in the tissue explant, the polarity of the epithelial cells in the tissue explant is substantially maintained as in the source architecture of the tissue from which it was derived (e.g., small intestine) in the in vitro cellular composition, and use thereof. In some embodiments, the tissue explant described herein mimics in vivo architecture. In some embodiments, the tissue explant described herein mimics the in vivo architecture of the small intestine. In some embodiments, a tissue explant mimics in vivo architecture wherein it comprises one or more physical structures representative of the in vivo tissue from which it was derived. For example, wherein the tissue explant is derived from the small intestine, it mimics the in vivo architecture of the small intestine by comprising at least one structure of the small intestine from the tissue from which it was derived, for example, by comprising intact crypts, intestine epithelium, circular muscular layer and/or villi, or any combination of the foregoing. In some embodiments, a tissue explant mimics in vivo architecture by comprising one or more or a majority of the structures of the tissue from which it was derived, for example by comprising intact crypts, intestine epithelium, circular muscular layer and/or villi, or any combination of the foregoing. In some embodiments the tissue explant comprises intact crypts, intestine epithelium, circular muscular layer, and villi from the tissue from which it was derived (e.g., a large, non-human, mammalian gastrointestinal tract or a human gastrointestinal tract). In some embodiments, determination of the architecture of the tissue explant and whether it mimics the in vivo architecture of the tissue from which it is derived can be determined by standard techniques known in the art, for example, by comparing the structure of the tissue explant in the in vitro cellular composition of the disclosure by methods described herein (e.g., histological staining) with images or information available to those of skill in the art (e.g., previously obtained images of the tissue from which the explant is derived). In some embodiments, comparisons are made between tissue explants cultured ex vivo and tissue explants freshly excised.

As used herein, "a basolateral surface" refers to the orientation of the tissue explant when contacted with a substrate, such that the tissue explant comprises apical/luminal-basolateral polarity. In some embodiments, the basolateral surface is opposite of the apical surface, i.e., the luminal surface.

As used herein, "contacting" refers to either placing a substrate on a tissue explant described herein (or causing a tissue explant to come in contact with a substrate), or placing a compound of interest on an in vitro cellular composition described herein (or causing a compound of interest to come in contact with an in vitro cellular composition).

As used herein, "detecting", "detect" and "detection" refer to the identification and/or quantification of a compound of interest (e.g., drug, agent, etc.) in a sample. In some embodiments, detecting comprises determining the absence or presence of a compound of interest in a sample. In some embodiments, detecting comprises quantifying a compound of interest in a sample. In some embodiments, detecting comprises identifying and/or quantifying a compound of interest in a sample at different time points. In some embodiments, detecting comprises identifying and/or quantifying a compound of interest in a first sample and in a second sample.

As used herein, "drug absorption" or "drug perfusion" refers to the movement of drug into the bloodstream and through tissues following administration, as well as movement of drug through the tissue explant following contact of drug with the tissue explant. Drug absorption or perfusion is determined by the drug's physicochemical properties, formulation, and route of administration.

As used herein, "drug dissolution" refers to the rate a dosage form (e.g., tablet) of a drug dissolves in the fluids of the gastrointestinal tract prior to absorption into the systemic circulation.

As used herein, "drug transporter" refers to proteins that move drugs across the cell membrane. In general, drug transporters are divided into two major superfamilies: ATP-binding cassette (ABC) family and solute carrier (SLC) family. The ABC transporters are primary active transporters that utilize the energy from ATP hydrolysis to transport substrates (e.g., drugs) across the membrane. SLC transporters can either be facilitative transporters, which transport their substrates down the gradient across the membrane, or secondary active transporters, which transport their substrates against the gradient across the membrane by coupling a downhill transport of another substrate.

As used herein, "exogenous" refers to molecules or compositions originating or produced from outside an organism, tissue or cell.

As used herein, the "extracellular matrix" refers to a complex non-cellular three-dimensional macromolecular network composed of collagens, proteoglycans/glycosaminoglycans, elastin, fibronectin, laminins, and several other glycoproteins. These molecules are secreted locally by cells and remain closely associated with them to provide structural, adhesive and biochemical signaling support.

As used herein, "ex vivo" refers to a condition that takes place outside an organism. In some embodiments, ex vivo refers to experimentation or measurements done in or on a tissue from an organism in an external environment.

As used herein, "gastrointestinal tract" refers to the complete system of organs and regions that are involved with ingestion, digestion, and excretion of food and liquids. This system generally consists of, but is not limited to, the mouth, esophagus, stomach and or rumen, intestines (small and large), cecum (plural ceca), fermentation sacs, and the anus.

As used herein, "high-throughput" refers to the parallelization of experiments. Specifically, several experiments can be run simultaneously as opposed to single experiments carried out one after another. In some embodiments, high-throughput experiments are carried out using automated techniques.

As used herein, "intestinal cells" refers to cells that make up the mammalian intestinal epithelium. The mammalian intestinal epithelium of the gastrointestinal tract has a well-defined organizational structure. The epithelium can be divided into two regions, a functional region that houses differentiated cells (villi) and a proliferative region (crypts of Lieberkuhn) that represents the epithelium stem cell niche. Multipotent epithelium stem cells reside in the crypts and give rise to four principal epithelial lineages: absorptive enterocytes, mucin secreting goblet cells, peptide hormone secreting enteroendocrine cells, and Paneth cells.

As used herein, "intestine" refers to the mammalian small intestine and mammalian large intestine.

As used herein, "intestinal stem cells," used interchangeably with "epithelial stem cells" refers to stem cells that have the potential to proliferate and differentiate into intestinal epithelial cells. Multipotent epithelial stem cells give rise to various epithelial lineages, and may give rise to all intestinal epithelial lineages, which include: absorptive enterocytes, mucin secreting goblet cells, peptide hormone secreting enteroendocrine cells, and Paneth cells.

As used herein, "in vitro" refers to processes performed or taking place outside of a living organism. In some embodiments, the processes are performed or take place in a culture dish.

As used herein, "in vivo" refers to processes that occur in a living organism.

As used herein, "lamina propria" refers to a thin layer of loose connective tissue, or dense irregular connective tissue, which lies beneath the epithelium and together with the epithelium constitutes the mucosa.

As used herein, "lamina muscularis," "lamina muscularis mucosae" and "muscularis mucosae" refer to a thin layer of muscle of the gastrointestinal tract located outside the lamina propria and separating it from the submucosa.

As used herein, "large mammal" refers to a species in which normal mature adults of either sex may attain a body mass of at least one kilogram. In some embodiments, a large mammal is an ungulate (i.e., hoofed mammals such as pigs, cows, goats, sheep, horses, donkeys, deer, antelopes and the like). In some embodiments, a large mammal is livestock (i.e., mammals raised for agricultural purposes such as pigs, cows, goats, sheep, horses, rabbits, and the link, and/or as beasts of burden such as donkeys, horses, elephants, camels, llamas, and the like). In some embodiments, a large mammal is a human.

As used herein, "luminal surface" refers to the orientation of the tissue explant when contacted with a substrate, such that the tissue explant comprises apical/luminal-basolateral polarity. In some embodiments, the luminal surface is opposite of the basolateral surface.

As used herein, "maintained in culture" refers to the continued application of conditions that are required for the growth or survival of a specific cell type in an artificial environment. In some embodiments the artificial environment includes substrate or medium that supplies the essential nutrients (e.g., amino acids, carbohydrates, vitamins, minerals), growth factors, hormones, gases (e.g., O2, CO2), and physicochemical environment (e.g., pH, osmotic pressure, temperature). In some embodiments, the tissue explant described herein is maintained in culture for up to 1 week. In some embodiments, the tissue explant described herein is maintained in culture for up to 2 weeks. In some embodiments, the tissue explant described herein is maintained in culture for up to 3, 4, 5, 6, 7, 8, 9, 10, 11, 12, 13, 14, 15, 16 or 17 weeks. In some embodiments, the tissue explant described herein is maintained in culture for up to 18 weeks.

As used herein, "drug metabolizing enzyme", "DME" and "metabolizing enzyme" refer to polypeptides responsible for metabolizing a vast array of xenobiotic chemicals, including drugs, carcinogens, pesticides, pollutants and food toxicants, as well as endogenous compounds, such as steroids, prostaglandins and bile acids. Metabolic biotransformation of chemicals by DMEs form more hydrophilic, polar entities, which enhance their elimination from the body and lead to compounds that are generally pharmacologically inactive and relatively nontoxic. In some embodiments, metabolic biotransformation can lead to the formation of metabolites with pharmacological activity. Xenobiotics are metabolized by four different reactions: oxidation, reduction, hydrolysis and conjugation. Oxidation, reduction and hydrolysis are referred to as Phase I reactions, and conjugation is referred to as a Phase II reaction. Oxidative Phase I DMEs include cytochrome P450s (CYPs or P450s), Flavin-containing monooxygenases (FMOs), monoamine oxidase (MAOs), and xanthine oxidase/aldehyde oxidase (XO/AO). Conjugative Phase II DMEs include uridine 5'-diphospho (UDP)-glucuronosyltransferases (UGTs), sulfotransferases (SULTs), glutathione S-transferases (GSTs), N-acetyltransferase (NATs), and methyl (N-methyl-, thiomethyl-, and thiopurinemethyl-) taransferases. Of the DMEs involves in the metabolism of drugs, the dominant players are P450 enzymes, followed by UGTs and esterases. Accordingly, in some embodiments, the tissue explant described herein comprises Phase I and Phase II metabolizing enzymes. In some embodiments, the tissue explant described herein comprises a cytochrome P450 enzyme and a UGT enzyme.

As used herein, "modulation of gene expression" refers to changes in the induction or repression of a gene. Mechanisms that are involved with the gene regulation include structural and chemical changes to the genetic material, binding of proteins to specific DNA elements to regulate transcription, and/or mechanisms that modulate translation of mRNA. In some embodiments, gene expression of the tissue explant described herein is modulated. In some embodiments, gene expression of at least one drug transporter present in the tissue explant described herein is modulated. In some embodiments, gene expression of at least one metabolizing enzyme present in the tissue explant described herein is modulated.

As used herein, "mucus" refers to a viscid secretion that is usually rich in mucins and is produced by mucous membranes which it moistens and protects. In some embodiments, the tissue explant described herein produces mucus.

As used herein, "muscularis externa" refers to the circular muscle layer and the longitudinal muscle layer, which separate the submucosa from the subserous layer. In some embodiments, the tissue explant described herein comprises an intact muscularis externa. In some embodiments, the tissue explant described herein comprises only the circular muscle layer.

As used herein, "oral bioavailability" refers to the degree to which a drug or other substance becomes available to a target tissue after oral administration. Bioavailability is related to the physiochemical properties of a drug or other substance, e.g., dissolution, membrane transport, chemical stability, etc., as well as the interactions with the host, e.g., metabolic fate, distribution and clearance. In some embodiments, the tissue explant described herein predicts the oral bioavailability of a drug or other substance of interest.

As used herein, "Pearson product-moment correlation coefficient" or "Pearson correlation coefficient" refers to a measurement of the strength of a linear association between two variables and is denoted by "r".

As used herein, "planar contact" refers to the placement of the tissue explant on a substrate, such that the tissue explant interacts with a two-dimensional surface of the substrate. Planar contact can be determined by methods known to those of skill in the art. For example, a method for analyzing planar contact comprises (i) contacting a tissue explant with a solution comprising a marker (e.g., dye) to stain the tissue and (ii) detecting the stain on the surface of the tissue by photographic inspection, spectrophotometrically or by laser scanner. The tissue explant is considered to be in planar contact with the substrate if there is no significant difference in variability of the marker within the area contacted with the substrate compared to an equivalent area of non-mounted tissue completely immersed in the solution comprising the marker. In another example, planar contact is determined by (i) coating the substrate with a marker that forms a uniform layer on the surface of the substrate; (ii) contacting the substrate with the tissue explant; and (iii) analyzing the resulting stain on the tissue explant once it is separated from the substrate by visual inspection. The tissue explant is considered to be in planar contact with the substrate if the tissue shows a regular pattern of markings across the entire tissue that correlate with the pattern of the substrate.

As used herein "polarity" refers to the organization of the cell membrane with associated proteins, along with the arrangement of the cytoskeleton and organelles within the cytoplasm. For example, epithelial cells are organized along a cellular axis that extends from the apical side facing an external lumen to the basal side facing either the extracellular matrix or adjacent cells. In addition to the apical-basal axis of polarity, epithelial cells are often oriented within the plane of the tissue along a proximal-distal axis, referred to as "tissue polarity" or "planar polarity In some embodiments, the apical-basal axis of polarity of epithelial cells is maintained in the tissue explant following removal from the source tissue. In some embodiments, the apical-basal axis of polarity of epithelial cells is maintained in the tissue explant following contact with the substrate. In some embodiments, the apical-basal axis of polarity of epithelial cells is maintained in the in vitro cellular composition following use in the methods as described herein. In some embodiments, the proximal-distal axis of polarity is maintained in the tissue explant following removal from the source tissue. In some embodiments, the proximal-distal axis of polarity of epithelial cells is maintained in the tissue explant following contact with the substrate. In some embodiments, the proximal-distal axis of polarity of epithelial cells is maintained in the in vitro cellular composition following use in the methods as described herein. In some embodiments, both the apical-basal axis and proximal-distal axis of polarity are maintained in the tissue explant following contact with the substrate. In some embodiments, the apical-basal axis and the proximal-distal axis of polarity of epithelial cells is maintained in the tissue explant following contact with the substrate. In some embodiments, the apical-basal axis and proximal-distal axis of polarity of epithelial cells is maintained in the in vitro cellular composition following use in the methods as described herein. Methods of determining polarity are known to those of skill in the art. A review of such methods can be found in Chapter 7 of Cell Polarity and Morphogenesis (Academic Press, 2017, herein incorporated by reference in its entirety). In some embodiments, polarity of the tissue explant described herein is analyzed by visual (e.g., microscopic) inspection. For example, in some embodiments, the tissue explant described herein comprises two or more genetically distinct cell populations and polarity can be determined by expression of a labeled protein in only a subset of cells and subsequently visualized by microscopic techniques. In some embodiments, immunohistochemistry and live images of fluorescent reports are used to visualize proteins in their tissue context and evaluate their distribution. In some embodiments, cell polarization is quantified by analyzing protein localization in fluorescent images and calculating the ratio of fluorescence intensity between regions where the protein is present and regions where it is weakly localized or absent. The fluorescence ratio provides a quantitative measure of asymmetric protein distribution. See Marcinkevicius, E., et al. *J. Biol.* 2009, Vol. 8(12): 103, herein incorporated by reference in its entirety. In some embodiments, the fluorescence ratio is normalized by choosing appropriate analysis settings and incorporating internal controls, as described by Shimoni, R., et al. *PLos ONE* 2014, Vol. 9(6): e99885, herein incorporated by reference in its entirety.

As used herein, "reusable" refers to the ability of a tissue explant to be subjected to more than one experiment in succession.

As used herein, "responsive" refers to a reaction elicited by a stimulus. In some embodiments, the tissue explants described herein are responsive to a stimulus. In some embodiments, the tissue explant described herein is responsive to glucose. In some embodiments, increased GLP-1 activity (e.g., increased concentration of active GLP-1 7-36) indicates the tissue explant is responsive to glucose. In some embodiments, when the apical side of the tissue explant is contacted with glucose, GLP-1 activity is increased. In some embodiments, modulation of gut hormones and/or tissue behavior indicates the tissue explant is responsive to glucose. Methods for measuring gut hormones and tissue behavior are described herein.

As used herein, "substrate" refers to a surface or layer that underlies something, for example, a cell, cell culture, cell culture material, etc., or on which processes occur. In some embodiments, a substrate is a surface or material on which an organism lives, grows, and/or optionally obtains nourishment. The term "substrate" also refers to a surface or layer, e.g., a base surface or layer, on which another material is deposited. Exemplary substrates include, but are not limited to, glass, silicon, polymeric material, plastic (e.g., tissue culture plastic), etc. Substrates can be slides, chips, wells and the like.

As used herein, "tissue explant" refers to an isolated piece or pieces of tissue. In some embodiments, the tissue explant is isolated from the gastrointestinal tract.

Tissue Explant

Tissue explants described herein are useful in the method described herein as they provide features of in vivo tissue from which they are derived. Features include, without limitation, prolonged tissue expansion with proliferation, multilineage differentiation, and recapitulation of cellular and tissue architecture, including epithelial tissues, submucosal tissues, and stromal environments.

In some embodiments, tissue explants for use in the disclosure include, but are not limited to, tissues from the stomach, small intestine, duodenum, esophagus, buccal, colon or tongue.

A. Method for Obtaining Tissue Explant

The tissue explant described herein provides for culture, maintenance of in vivo architecture and recapitulation of tissue function, for example, long term or prolonged culture, maintenance of in vivo architecture and recapitulation of tissue function and use in methods described herein. The tissue explants described herein are useful for analysis of the tissue of interest (e.g., small intestine) and high-throughput screening assays.

In some embodiments, the tissue explant described herein is derived from either a human or a large, non-human mammal. In some embodiments, the large, non-human mammal, includes ungulates (i.e., hoofed mammals such as pigs, cows, goats, sheep, horses, donkeys, deer, antelopes and the like) and more generally, livestock (i.e., mammals raised for agricultural purposes such as pigs, cows, goats, sheep, horses, rabbits, and the link, and/or as beasts of burden such as donkeys, horses, elephants, camels, llamas, and the like). In some embodiments, the large, non-human mammal is a pig.

In some embodiments, the tissue of interest (e.g., small intestine) is obtained surgically. In some embodiments, the tissue of interest (e.g., small intestine) is obtained surgically post-exsanguination (i.e., draining of blood). In some embodiments, the tissue explant obtained is the length and width of the substrate of interest. In some embodiments, the tissue explant obtained is the length and width of a standard 6, 12, 24, 48, 96, 384, 1536 or 3456 well plate. In some embodiments, the tissue explant obtained is the length and half the width of a standard 6, 12, 24, 48, 96, 384, 1536 or 3456 well plate. In some embodiments, the tissue explant is about 127.8 mm in length and about 42.75 mm in width. In some embodiments, the tissue explant is about 127.8 mm in length and 85.5 mm in width.

In some embodiments, the age of the animal can have an effect on the maintenance and function of the tissue explant. In some embodiments, the animal is between 3 weeks and 12 weeks of age. In some embodiments the animal is 3 weeks of age. In some embodiments the animal is 12 weeks of age. In some embodiments the animal is 1, 2, 3, 4, 5, 6, 7, 8, 9, 10, 11, 12, 13, 14 or 15 weeks of age. In some embodiments, the animal is 1, 2, 3, 4, 5, 6 or 7 months old. In some embodiments, fetal tissue is utilized.

In some embodiments, the tissue explant is immersed in a series of saline solutions after dissection. In some embodiments, the tissue explant is immersed in 70% ethanol after dissection, followed by washing with saline solutions. In some embodiments, the saline solutions are supplemented with an antibiotic solution. In some embodiments, the saline solutions are supplemented with an antimycotic solution. In some embodiments, the saline solutions are supplemented with an antibiotic and antimycotic solution. Antibiotic and antimycotic solutions are known by those of skill in the art. For example, Gibco® Antibiotic-Antimycotic solution is useful in the methods described herein. In some embodiments, the antibiotic and/or antimycotic solution comprises penicillin, streptomycin, Gibco® amphotericin B, or combinations thereof.

In some embodiments, the tissue explant is immersed in a known preservation solution. Examples of preservation solutions include, but are not limited to, Krebs-Henseleit solution, UW solution, St. Thomas II solution, Collins solution, and Stanford solution (See, for example, U.S. Pat. Nos. 4,798,824 and 4,938,961; Southard and Belzer, *Ann. Rev. Med.* 46:235-247 (1995); and Donnelly and Djuric, *Am. J. Hos. Pharm.* 48:2444-2460 (1991)). The solution may contain one or more of sodium, potassium, calcium, magnesium, glutamate, arginine, adenosine, mannitol, allopurinol, glutathione, raffinose, and lactobionic acid. In some embodiments, the solution is maintained at physiological pH of about 7.2-7.4.

In some embodiments, the tissue is kept on ice before dissection. Therefore, in some embodiments the solutions are 4° C. before being used.

The tissue explant is subsequently mounted on the substrate of interest (e.g., multi-well plate) and cultured in culture media at 37° C. in an airtight container. In some embodiments, the culture media is free of serum. In some embodiments, the culture media comprises serum.

In some embodiments, the culture media does not contain exogenous growth factors (e.g., Wnt3a). In some embodiments, the tissue explant does not require exogenous growth factors due to the presence of the stromal layer. In some embodiments, the culture media is Dulbecco's Modified Eagle Medium (DMEM) or Advanced DMEM/F-12. In some embodiments, the culture media includes fetal bovine serum (FBS). In some embodiments, the culture media include EGF Recombinant Human Protein. In some embodiments, the presence of FBS and/or EGF does not affect the viability of the tissue explant.

In some embodiments, the tissue explant is derived from the gastrointestinal tract of a human or large, non-human mammal. The gastrointestinal tract comprises the mouth, esophagus, stomach and or rumen, intestines (small and large), cecum (plural ceca), fermentation sacs, and the anus. In some embodiments, the tissue explant is derived from the intestine. In some embodiments, the tissue explant is derived from the small intestine.

The roughly 8 meters of intestine in the adult human plays numerous roles in physiologic homeostasis including absorptive, secretory and immune functions. Commensurate with these essential roles, diseases of the intestine are a considerable source of human morbidity and mortality. Indeed, numerous pathologic conditions including cancer, inflammatory bowel diseases, mesenteric ischemia, congenital syndromes and trauma, with or without concomitant intestinal resection, result in "short-gut" syndromes resulting in severe deficiencies of physiologic intestinal function and effective intestinal failure.

The intestine is an organ with tremendous regenerative potential, whereby stem cells resident in proliferative crypt regions give rise to progenitors capable of multilineage differentiation. The intestinal stem cells (ISCs) are able to repopulate epithelium of the entire 8-meter length of the adult human intestine every 5-7 days, helping to maintain the integrity of the mucosal barrier and effecting tissue repair upon injury. It has been postulated that the ISC niche has complex architectural requirements whereby myofibroblasts enveloping the proliferative crypt provide essential signals to crypt stem and/or progenitor cells.

The small intestine has three distinct regions, the duodenum, jejunum and ileum. The duodenum is connected to the distal end of the stomach and receives bile and pancreatic juice through the pancreatic duct. The jejunum and ileum primarily absorb nutrients and water more so than the breaking down of food.

In some embodiments, the tissue explant is derived from the jejunum of the small intestine. In some embodiments, the tissue explant is derived from the ileum of the small intestine. In some embodiments, the tissue explant is derived from the duodenum of the small intestine.

B. Composition of Tissue Explant

Tissue

Intestine

Like other parts of the gastrointestinal tract, the small intestine is comprised of four basic layers: the mucosa, submucosa, muscularis externa, and serosa. It is the body's major digestive organ, the site where digestion is completed and almost all absorption occurs. The small intestine is highly adapted for nutrient absorption. Both its long length and the modifications of its inner surface provide an extraordinary large surface area and enhance absorption enormously.

The outermost layer of the intestine, the serosa, is a smooth membrane consisting of a thin layer of cells that secrete serous fluid, and a thin layer of connective tissue. The muscularis externa, adjacent to the submucosa membrane, comprises two muscle layers of an inner circular and outer longitudinal smooth muscle. It is responsible for gut movement (i.e., peristalsis). The submucosa is a layer of dense irregular connective tissue or loose connective tissue that supports the mucosa and joins it to the underlying smooth muscle. The innermost layer and lining of the small intestine is the mucosa. It is a mucous membrane that secretes digestive enzymes and hormones. The mucosa comprises intestinal villi, an epithelium and a lamina propria. The lamina propria is a thin layer of loose connective tissue, or dense irregular connective tissue, which lies beneath the epithelium and together with the epithelium constitutes the mucosa.

In some embodiments, the tissue explant described herein comprises the serosa, muscularis externa, submucosa and mucosa. In some embodiments, the tissue explant described herein comprises the muscularis externa, submucosa and mucosa. In some embodiments, the tissue explant described herein comprises the inner circular smooth muscle, the submucosa, and the mucosa. Methods for identifying these structures include visual inspection, by, for example, histological staining (e.g., haemotoxylin & eosin stain) followed by microscopic analysis. Using such methods, one of skill in the art can identify the various structures of the tissue explant.

In some embodiments, the tissue explant described herein comprises a fully intact extracellular matrix. In some embodiments, the extracellular matrix comprises the lamina propria. In some embodiments, the extracellular matrix comprises the lamina muscularis.

In some embodiments, the tissue explant described herein maintains polarity (e.g., epithelial cell polarity) as described herein. In some embodiments, the tissue explant described herein is in a planar position, thereby providing a luminal surface and a basolateral surface. In some embodiments, either surface is accessible. Methods of determining polarity are known to those of skill in the art. A review of such methods can be found in Chapter 7 of Cell Polarity and Morphogenesis (Academic Press, 2017, herein incorporated by reference in its entirety). In some embodiments, polarity of the tissue explant described herein is analyzed by visual (e.g., microscopic) inspection. For example, since the tissue explant described herein comprises two or more genetically distinct cell populations, polarity can be determined by expression of a labeled protein in only a subset of cells and subsequently visualized by microscopic techniques. In some embodiments, immunohistochemistry and live images of fluorescent reports are used to visualize proteins in their tissue context and evaluate their distribution. In some embodiments, cell polarization is quantified by analyzing protein localization in fluorescent images and calculating the ratio of fluorescence intensity between regions where the protein is present and regions where it is weakly localized or absent. The fluorescence ratio provides a quantitative measure of asymmetric protein distribution. See Marcinkevicius, E., et al. J. Biol. 2009, Vol. 8(12): 103, herein incorporated by reference in its entirety. In some embodiments, the fluorescence ratio is normalized by choosing appropriate analysis settings and incorporating internal controls, as described by Shimoni, R., et al. *PLos ONE* 2014, Vol. 9(6): e99885, herein incorporated by reference in its entirety.

In some embodiments, the tissue explant described herein maintains the in vivo architecture of the intestinal tissue from which it is derived. In some embodiments, the in vivo architecture is determined by visual inspection by methods known to those of skill in the art and described infra. For example, in some embodiments, determination of the maintenance of the in vivo architecture comprises comparing freshly excised tissue with tissue explants cultured ex vivo over time.

The intestinal villi, fingerlike extensions of the inner mucosal surface, are one of the primary specializations characteristic of the intestine's absorption and digestion functions. The epithelial cells that comprise the villi are chiefly absorptive cells or enterocytes. Their capacity to secrete, absorb, and digest specific ions and nutrients, depends on their position along the length of the intestine. The enterocytes, themselves, have microvilli, giving the mucosal surface a fuzzy appearance sometimes called the "brush border." The microvilli comprise enzymes which aid in digestion, such as disaccharidases and peptidases. In some embodiments, the tissue explant described herein comprises enterocytes. In some embodiments, enterocytes are identified by the presence of villin, e-cadherin, keratin 20, and/or fatty acid binding protein 1 (FABP1). In some embodiments, the tissue explant described herein comprises villi.

The intestinal mucus layer plays an important protective role. The mucus layer is primarily comprised of mucins. Mucins are highly glycosylated large glycoproteins with protein backbone structures rich in serine and threonine, which are linked to a wide variety of O-linked oligosaccharide side chains that make up more than 70% of the weight of the molecule. Up to 20 different mucin genes have been identified, MUC1 to MUC20 according to order of their discovery. Mucin genes are expressed in tissue and cell type-specific manner and are broadly classified into two types, secretory and membrane-associated. In small and large intestine, MUC2 is the major secretory mucin synthesized and secreted by goblet cells. Intestinal mucus layers secreted by goblet cells consist mainly of compact mesh-like network of viscous, permeable, gel-forming MUC2 mucin, which provides the frontline host defense against endogenous and exogenous irritants and microbial attachment and invasion but allows the transport of nutrients. In some embodiments, the tissue explant comprises mucin secreting goblet cells. In some embodiments, the tissue explant forms a mucus layer in culture. In some embodiments, the tissue explant described herein comprises mucosubstances. In some embodiments, the mucosubstances are glycoproteins, glycolipds or mucins.

Mucin 2 (Muc 2) as well as Caudal type homeobox 2 (CDX2) are both markers for the mucin secreting goblet cells within the intestinal epithelium. In some embodiments, goblet cells are identified by the presence of Mucin 2 (Muc 2) and/or Caudal type homeobox 2 (CDX2).

In some embodiments, presence of a mucus layer in the tissue explant described herein is determined by measuring the presence of mucins and/or mucosubstances. In some embodiments, the presence of a mucus layer in the tissue explant described herein is determined by measuring the gene expression of Muc 2 and/or CDX2. In some embodiments, the presence of a mucus layer in the tissue explant described herein is determined by measuring the protein expression of Muc 2 and/or CDX2. In some embodiments, the presence of a mucus layer in the tissue explant described herein is determined by visual inspection (e.g., microscopy). In some embodiments, histological staining, such as with alcian blue tissue stain, is used for visual inspection.

Between the villi, the mucosa is studded with pits or openings which lead into tubular intestinal glands called intestinal crypts or crypts of Lieberkuhn. The epithelial cells which line the crypts secrete intestinal juice, a fluid mixture comprising mucus. Deep in the crypts are Paneth cells which produce various polypeptides, such as cryptdin, lysozyme, type II (secretory) phospholipase A2, intestinal defensin (e.g., RIP-3). In some embodiments, the tissue explant described herein comprises intact crypts. In some embodiments, intact crypts are identified by visual inspection (e.g., microscopy). Methods of visual inspection for identifying intact crypts include, but are not limited to, histological tissue staining and normal light microscopy.

The gastrointestinal tract is characterized by self-renewing epithelium fueled by adult stem cells residing at the bottom of the intestinal crypt and gastric glands. In the adult intestine, cellular division only occurs in the crypt, not in the villus. Several potential stem cell populations have been proposed in the crypt. One of them, named crypt based columnar (CBC) cells is closely associated with Paneth cells at crypt bottoms. CBCs along with Paneth cells have long been proposed to form a restricted stem cell zone within the crypt, which has been confirmed by lineage tracing experiments. Such lineage tracing experiments have revealed that single Lgr5+ (leucine-rich repeat-containing G-protein coupled receptor 5) CBC cells are able to regenerate an entire crypt-villus axis. These cells are in a state of "stemness" and possess long-term self-renewal capabilities as well as multipotent differentiation abilities. In some embodiments, the tissue explant described herein comprises intestinal stem cells. In some embodiments, the intestinal stem cells are Lgr5+. In some embodiments, the presence of intestinal stem cells in the tissue explant described herein is responsible for long-term maintenance of the explant.

In addition to Lgr5+, olfactomedin-4 (OLFM4) emerged as a robust marker for intestinal stem cells based on a gene signature of Lrg5 stem cells. Therefore, in some embodiments, the tissue explant described herein comprises OLFM4+ stem cells. In some embodiments, the tissue explant described herein comprises Lrg5+ and OLFM4+ stem cells. In some embodiments, Lrg5+ and OLFM4_stem cells are detected by methods known to those of skill in the art and further described herein.

Several signaling mechanisms are also involved in maintaining the renewal capacity of the small intestine. Wnt, BMP/TGF-β, Notch and EGF are key regulators of epithelial homeostasis and self-renewal activity. While the cells move across the crypt-villus axis they are exposed to a Wnt gradient. Stem cells become loaded with Wnt mediators that are produced by adjacent Paneth cells, which bind to their cognate Frizzled receptors. Due to their local production and limited diffusion, Wnt molecules as well as their receptors are diminished through turnover by cellular division as the cells leave the stem cell zone and move away from Paneth cells. Besides Lgr5+, the CBC stem cells express a whole set of further Wnt pathway associated genes, which directly controls stemness in the intestinal crypts. The high Wnt activity in CBC stem cells is mediated by binding of secreted R-spondin family members to Lgr family members on the CBC membrane. This binding potentiates the Frizzled mediated Wnt pathway activation and results in robust activation of the Wnt pathway. Moreover, myofibroblasts play a role in maintaining the renewal capacity of the small intestine by providing signaling cues. Specifically, myofibroblasts, which surround the intestinal crypt, secrete factors such as Wnt ligands, HGF, BMP and Noggin, important in regulating differentiation (see Medema, J. and Vermeulen, L., *Nature, Vol.* 474: 318-326, 2011, herein incorporated by reference).

Prior intestinal model systems, including primary intestinal epithelial cells and/or intestinal stem cells, require exogenous addition of Wnt to maintain the systems. The tissue explants described herein do not require exogenous Wnt for culture maintenance. The presence of intact crypts and villi, along with stroma, contribute to this feature of the tissue explants described herein.

In some embodiments, the tissue explant described herein comprises intestinal endocrine cells. Intestinal endocrine cells, or enteroendocrine cells, are restricted to the mucosa and located within the intestinal crypts and villi (Moran, G., et al. Therap Adv Gastroenterol. 2008 July; Vol. 1(1): 51-60, herein incorporated by reference in its entirety). Enteroendocrine cells found in the small intestine include, but are not limited to, cholecystokinin-secreting cells, secretin-secreting S cells, gastric inhibitory polypeptide-secreting cells, motilin-secreting M cells and neurotensin secreting N cells, and neuroendocrine L cells. In some embodiments, the tissue explant described herein comprise L cells. Enteroendocrine cells are characterized by the presence of secretary vesicles. Enteroendocrine cells secrete glucagon-like peptide-1 (GLP-1). In some embodiments, secretion of GLP-1 is in response to the presence of glucose. In some embodiments, secretion of GLP-1 is in response to the presence of acetylcholine. In some embodiments, secretion of GLP-1 is in response to the presence of LiCl. In some embodiments, secretion of GLP-1 is determined by the concentration of GLP-1 7-36. In some embodiments, the tissue explant described herein is responsive to glucose, acetylcholine and/or LiCl due to the presence of enteroendocrine cells.

In some embodiments, the tissue explant described herein comprises tight junctions. In some embodiments, tight junctions are identified by the presence of claudin-1, e-cadherin, or a combination thereof, determined by methods known to those of skill in the art and further described herein. Claudin-1 is an integral membrane protein and e-cadherin is a transmembrane protein, both of which are components of tight junctions. Tight junctions represent one mode of cell-to-cell adhesion in epithelial or endothelial cell sheets, forming continuous seals around cells and serving as a physical barrier to prevent solutes and water from passing freely.

The submucosa contains individual and aggregated lymphoid patches, the latter called Peyer's patches. In the duodenum only, mucus-secreting duodenal glands (also called Brunner's glands) are found. Microfold (M) cells are found in Peyer's patches of the intestine and are specialized for the phagocytosis and transcytosis of gut lumen macromolecules. These cells play an important role in the induction of specific mucosal immune responses in the Peyer's patches, and allow for transport of microbes and particles across the epithelial cell layer from the gut lumen to the lamina propria where interactions with immune cells can take place. In some embodiments, the tissue explant described herein comprises microfold cells. Microfold cells are identified by cytoskeletal and extracellular matrix components expressed at the edge of the cells or on their cell surfaces, including actin, villin, cytokeratin and vimentin. In some embodiments, microfold cells are identified by the presence of vimentin, actin, cytokeratin, villin, or combination thereof. In some embodiments, microfold cells are identified by the presence of vimentin. In some embodiments, microfold cells are identified by the presence of actin. In some embodiments, microfold cells are identified by the presence of villin. In some embodiments, microfold cells are identified by the presence of cytokeratin.

The enteric nervous system (ENS) is the intrinsic nervous system of the gastrointestinal tract. It contains complete reflex circuits that detect the physiological condition of the gastrointestinal tract, integrate information about the state of the gastrointestinal tract, and provide outputs to control gut movement, fluid exchange between the gut and its lumen, and local blood flow. The ENS works in concert with the central nervous system (CNS) to control the digestive system in the context of local and whole body physiological demands.

The ENS originates from neural crest cells. These cells proliferate and differentiate into neurons and glial cells, and form two concentric plexuses of ganglion cells localized in the muscle layers of the gut wall (Furness, J. B. (2006). The organisation of the autonomic nervous system: peripheral connections. Auton. Neurosci. 130, 1-5. doi:10.1016/j.autneu.2006.05.003). In some embodiments, the tissue explant described herein comprises neural cells. In some embodiments, neural cells are identified by the presence of nestin. Nestin is an intermediate filament protein that is a known neural stem/progenitor cell marker.

Colon

In some embodiments, the tissue explant is derived from the colon. The colon is a part of the digestive system that functions in the absorption of water, electrolytes, and nutrients that remain after passing through the small intestine, and also in the compaction of feces. The lining of the colon, and its innermost layer, is the mucosa. The tunica serosa is the outermost covering of the digestive tube. It is comprised of an irregular dense connective tissue surrounded by a mesothelium, a type of squamous epithelium. Underneath the tunica serosa is the muscularis externa, comprising two muscle layers of an inner circular and outer longitudinal muscle. Between the layers are nervous plexus (Auerbach's myenteric). A fibroelastic connective tissue is found at the next level. Called the submucosa, it contains submucosal (Meissner) nervous plexuses, pre- and post-ganglionic parasympathetic fibers, and nonmyelinated preganglionic fibers from the vagus nerve. The innermost layer and lining of the colon is the mucosa. It comprises of an epithelium, a lamina propria, and muscularis mucosae. The epithelium is a simple columnar absorptive epithelium. The lamina propria is a loose connective tissue beneath the epithelium, and the muscularis mucosae is a thin smooth muscle cell layer surrounding the mucosa. The mucosa contains glands or crypts. The crypts comprise goblet cells and regenerative cells or enterocytes. The lamina propria (LP) fills the spaces between the crypts. The crypts are filled with large numbers of goblet cells that secrete mucus to lubricate ejection of the feces.

In some embodiments, the tissue explant described herein retains the in vivo architecture of the colon tissue from which it is derived. For example, in some embodiments, the issue explant comprises the epithelium and lamina propria of the colon. In some embodiments the tissue explant comprises the epithelium, lamina propria and muscularis mucosae of the colon. In some embodiments, the tissue explant further comprises the inner circular muscle from the muscularis externa of the colon. In some embodiments, the tissue explant comprises the inner circular and longitudinal muscle of the muscularis externa. In some embodiments, the tissue explant further comprises the submucosa of the colon. In some embodiments, the tissue explant further comprises intact crypts found in the colon. In some embodiments, the tissue explant derived from the colon comprises a mucus layer. In some embodiments, the tissue explant derived from the colon comprises a mucus layer and bowel content present on the apical side of the colon. In some embodiments, a tissue explant derived from the colon comprising a mucus layer and bowel content present on the apical side of the colon is useful for microbiome studies.

Stomach

In some embodiments, the tissue explant is derived from stomach, or gastric, tissue. The stomach is a muscular, hollow, dilated part of the alimentary canal. It comprises a mucosal layer comprising mucosal epithelium and lamina propria; which is surrounded by a submucosal layer comprising loose connective tissue; which is surrounded by a muscularis layer comprising several thick layers of muscle. The mucosal epithelium is comprised of four major types of secretory epithelial cells: mucous cells, which secrete an alkaline mucus that protects the epithelium against shear stress and acid; parietal cells, which secrete hydrochloric acid; chief cells (also called "peptic cells") which secrete the zymogen pepsinogen; and G cells, which secrete the hormone gastrin. Cells within the mucosal epithelium can be identified by methods known to those of skill in the art. The epithelium is folded into thousands of tiny pits, called gastric pits, at the base of which are gastric glands; the mucous cells reside at the neck of the pits, while the chief cells and parietal cells residue at the base of the pits, in the glandular zone. Other markers of terminal gastric epithelial differentiation include H+/K+ atpase and mucin (MUC5A).

Stomach tissue also comprises a stomach-specific stem cell, a villin$^{+}$Lgr$^{5+}$ cell which is able to give rise to all gastric cell lineages. Current molecular markers for gastric progenitor cells and gastric cancer stem cells are described in J. Gastroenterol. 2011 July; 46(7):855-65, the disclosure of which is incorporated herein by reference.

In some embodiments, the tissue explant described herein retains the in vivo architecture of the stomach tissue from which it is derived. For example, in some embodiments, the tissue explant comprises the mucosal epithelium and lamina propria from the stomach. In some embodiments, the tissue explant further comprises the muscularis layer from the stomach. In some embodiments, the tissue explant derived from the stomach comprises mucous cells, parietal cells, chief cells, G cells, or combinations thereof. In some embodiments, the tissue explant derived from the stomach comprises villin+Lgr5+ stem cells.

Esophagus

In some embodiments, the tissue explant is derived from the esophagus. The esophagus is a muscular tube connecting the throat (pharynx) with the stomach. The esophagus is about 8 inches long and lined with mucosa. The upper esophageal sphincter (UES) is a bundle of muscles at the top of the esophagus which is under conscious control. The lower esophageal sphincter (LES) is a bundle of muscles at the low end of the esophagus, where it meets the stomach, and is not under voluntary control. When closed, the LES prevents acid and stomach contents from traveling backwards.

The esophagus consists of mucosa, submucosa, layers of muscle fibers between layers of fibrous tissue, and an outer layer of connective tissue (serosa). The mucosa (innermost layer) is a stratified squamous epithelium of approximately three layers of squamous cells, which contrasts the single layer of columnar cells of the stomach. At the base of the mucosa lies the muscularis mucosa. The epithelial layer, connective tissue and muscularis mucosa comprise the mucosa.

In some embodiments, the tissue explant described herein retains the in vivo architecture of the esophageal tissue from which it is derived. For example, in some embodiments, the tissue explant comprises the mucosa of the esophagus. In some embodiments, the tissue explant comprises the mucosa and muscularis mucosa of the esophagus. In some embodiments, the tissue explant derived from the esophagus further comprises the serosa.

Buccal and Lingual

In some embodiments, the tissue explant is derived from buccal tissue (oral mucosa; relating to the mouth or cheek). In some embodiments, the tissue explant is derived from lingual tissue (relating to the tongue).

Buccal tissue consists of two layers, the surface stratified squamous epithelium and the deeper lamina propria. The epithelium consists of the following four layers: stratum basale, stratum spinosum, stratum granulosum, and stratum corneum, Depending on the region of the mouth, the epithelium may be keratinized or nonkeratinized. Nonkeratinized squamous epithelium covers the soft palate, inner lips, inner cheeks and floor of the mouth. Keratinized squamous epithelium is present in the attached gingiva and hard palate.

In some embodiments, the tissue explant retains the in vivo architecture of the buccal tissue from which it is derived. For example, in some embodiments, the tissue explant comprises the surface stratified squamous epithelium of the buccal tissue. In some embodiments, the tissue explant comprises the stratum basale, stratum spinosum, stratum granulosum, stratum corneum, or combinations thereof. In some embodiments, the tissue explant comprises the surface stratified squamous epithelium and the lamina propria of the buccal tissue. In some embodiments, the tissue explant derived from the buccal tissue comprises keratinized epithelium. In some embodiments, the tissue explant derived from the buccal tissue comprises nonkeratinized epithelium.

The tongue is a muscular organ in the mouth covered in mucosa. It is a mass of interlacing skeletal muscle, connective tissue with some mucous and serous glands, and pockets of adipose tissue. The tongue is anchored to the mouth via webs of tough tissue and mucosa. The tether holding down the front of the tongue is called the frenum. In the back of the mouth, the tongue is anchored into the hyoid bone. The tongue consists of lingual papillae, which are the small structure on the upper surface of the tongue. Four types of papillae are found on the tongue: circumvallate papillae, fungiform papillae, filiform papillae and foliate papillae. All except the filiform papillae are associated with taste buds.

In some embodiments, the tissue explant described herein retains the in vivo architecture of the lingual tissue from which it is derived. For example, in some embodiments, the tissue explant comprises the connective tissue of the lingual tissue. In some embodiments, the tissue explant comprises mucous and serous glands present in the lingual tissue. In some embodiments, the tissue explant derived from the lingual tissue comprises intact lingual papillae. In some embodiments, the tissue explant derived from the lingual tissue comprises circumvallate papillae, fungiform papillae, filiform papillae, foliate papillae, or combinations thereof.

Culture and Activity of Tissue Explant

In some embodiments, the tissue explant described herein retains the functional characteristics of the tissue from which it is derived. In some embodiments, the functional characteristic retained is drug transportation/absorption.

Drug transportation is mediated by ATP-binding cassette (ABC) transporter and solute carrier (SLC) transporter families. These intestinal transporters are located in the brush border membrane as well as basolateral membrane. Each transporter exhibits its own substrate specificity, and some have broader specificities than others. In addition, the distribution and characteristics of the intestinal transporters exhibit regional differences along the intestine, implying diverse physiologic functions and in some cases pathologic responses. The International Transporter Consortium describe a limited number of transporters based on clinical evidence that they influence drug disposition and/or side effects (Nat Rev Drug Discov, 2010 March; 9(3): 215-236, herein incorporated by reference in its entirety). In some embodiments, the tissue explant comprises at least one intact drug transporter. In some embodiments, the at least one intact drug transporter is MDR-1 (multidrug resistance P-glycoprotein), canalicular multispecific organic anion transporter 2 (ABCC3), multidrug resistance-associated protein 2 (MRP-2), breast cancer resistance protein (BCRP), organic cation transporter 1 (OCT1), sodium-dependent neutral amino acid transporter 2 (SNAT2), peptide transporter 1 (PEPT1), monocarboxylate transporter 1 (MCT1) or organic solute transporter subunit alpha (OST-alpha).

Drug transporters often work together with drug-metabolizing enzymes (DMEs) in drug absorption and eliminations. Drug metabolism has a significant effect on drug efficacy and toxicity. Drug metabolic reactions are categorized as Phase I, which functionalize the drug molecule and prepare it for further metabolism, and Phase II, which are conjugative. In general, Phase I reaction products are partially or fully inactive. However, Phase I reaction products are sometimes more active than the originally administered drug. The major classes of Phase I enzymes include, but are not limited to, cytochrome P450 and flavin-containing monooxygenase. The major classes of Phase II enzymes include, but are not limited to, UDP glucuronyltransferase, sulfotransferase, glutathione S-transferase, N-acyltransferase, and N-acetyl transferase. Therefore, in some embodiments, the tissue explant described herein comprises at least one drug-metabolizing enzyme. In some embodiments, the at least one drug-metabolizing enzyme is a Phase I enzyme. In some embodiments, the at least one drug metabolizing enzyme is CYP3A4. CYP3A4 is an isoform of cytochrome P450. In some embodiments, the at least one drug-metabolizing enzyme is a Phase II enzyme. In some embodiments, the at least one drug metabolizing enzyme is uridine 5'-diphospho glucuronosyltransferase (UGT). UGT is a drug metabolizing enzyme expressed in the intestine that catalyzes glucuronidation, wherein it adds a glucuronic acid moiety to drugs or other substances, thereby triggering their elimination via the kidneys. In some embodiments, the at least one drug metabolizing enzyme is sulfotransferase, N-acetyltransferase, S-methyltransferase, thiopurine methyltransferase, glutathione s-transferase, or glucuronyltransferase.

In some embodiments, the tissue explant described herein retains thioredoxin reductase activity. Thioredoxin reductase is a ubiquitous enzyme involved in many cellular processes such as cell growth, and protection against oxidation stress. Thioredoxin plays a crucial role in a wide number of physiological processes, which span from reduction of nucleotides to deoxyriboucleotides to the detoxification from xenobiotics, oxidants and radicals. The redox function of thioredoxin is critically dependent on thioredoxin reductase. The thioredoxin system includes thioredoxin, thioredoxin reductase and NADPH. Thioredoxins serve as electron donors for enzymes such as ribonucleotide reductases, thioredoxin peroxidases, and methionine sulfoxide reductases. Many transcription factors require thioredoxin reduction for DNA binding.

In some embodiments, thioredoxin reductase activity of the tissue explant is determined using methods known to one of skill in the art. In some embodiments, thioredoxin reductase activity of the tissue explant is determined using a commercially available kit (e.g., Thioredoxin Reductase Activity Assay Kit, Ray Biotech).

In some embodiments, the tissue explant described herein retains protease activity. Proteases represent up to 2% of the human genome, with 500-600 different proteases identified. Proteases specifically cleave proteins at their extremities (N-terminal or C-terminal regions) and are referred to as exopeptidases, or in the middle of the proteins, and are referred to as endopeptidases. Depending on the mechanism, human proteases are classified as serine, threonine, cysteine, aspartic or metalloproteases. Some proteases are secreted and released in the extracellular milieu, while others have intracellular functions and exclusively remain inside cells. Proteases are heavily present in the gastrointestinal tract, both in the lumen and deeply into the tissues. Pancreatic proteases (tyrpsins, chymotrypsin, elastase, etc.) are released into the lumen of the upper gastrointestinal tract, where they exert digestive functions. The microbiota constitutes an important source of proteases.

In some embodiments, protease activity of the tissue explant is determined using methods known to one of skill in the art. For example, protease activity of the tissue explant can be determined using a commercially available kit (e.g., Protease Activity Assay Kit, RayBiotech).

In some embodiments, the tissue explant described herein is responsive to toxins. In some embodiments, the tissue explant described herein is responsive to substances with gastrointestinal toxicity. In some embodiments, the tissue explant described herein is responsive to substances with cellular toxicity. In some embodiments, the toxin is a non-steroidal anti-inflammatory drug (NSAID), a bronchodilator, a bisphosphonate, an antibiotic, an antiviral, a vasodilator or a diuretic. In some embodiments, the NSAID is naproxen, mesalamine, ketoprofen, indomethacin or meloxicam. In some embodiments, the bronchodilator is theophylline. In some embodiments, the bisphosphonate is etidronate. In some embodiments, the antibiotic is doxycycline or cefpodoxime. In some embodiments, the antiviral is oseltamivir or tenofovir. In some embodiments, the vasodilator is tadalafil. In some embodiments, the diuretic is amiloride. In some embodiments, the toxin is doxycycline.

In some embodiments, toxicity is assayed by determining viability of the tissue explant described herein. For example, a toxic substance may reduce viability of the tissue explant. Assays for viability include, but are not limited to, Live/Dead assays which stain the cells and allow for subsequent microscopic analysis. In some embodiments, FACS analysis is used to analyze viability (e.g., Live/Dead staining). In some embodiments, toxicity is assayed by determining the difference in cell culture maintenance of the tissue explant described herein. For example, a toxic substance may reduce the time in which the tissue explant can be maintained in culture. In some embodiments, toxicity is assayed by determining the difference in architecture of the tissue explant described herein. For example, a toxic substance may alter the architecture in a way that it no longer mimics the in vivo tissue from which the tissue explant was derived. In some embodiments, toxicity is assayed by analyzing metabolic activity. In some embodiments, metabolic activity is measured via alamarBlue® staining. In some embodiments, toxicity is measured by analyzing release of cellular compounds into medium. In some embodiments, release of cellular compounds is measured via adenylate kinase. In some embodiments, toxicity is measured by analyzing necrosis and/or apoptosis markers. In some embodiments, apoptosis markers include, but are not limited to, cleaved caspase3, cleaved lamin A and pHistone H2A. A person of ordinary skill in the art can readily determine induction of apoptosis using a variety of methods, for example, caspase activation assays (e.g., caspase-3/7 activation assays), stains and dyes (e.g., CELLTOX™, MITOTRACKER® Red, propidium iodide, and YOYO3), cell viability assays, cell morphology, and PARP-1 cleavage. In some embodiments, staining of cells with necrosis and/or apoptosis markers is analyzed via FACS. In some embodiments, toxicity is measured using a TUNEL assay.

In some embodiments, the tissue explant described herein recovers from exposure to a toxin. As used herein, the terms "recovery" and "recovers" refer to an increase in viability and/or a decrease in toxicity as measured by the methods described herein, such as by alamarBlue® assay. In some embodiments, recovery occurs over 1 day, 2 days, 3 days, 4 days, 5 days, 6 days or at least 7 days after initial exposure to a toxin.

In some embodiments, the tissue explant described herein is maintained in culture. A tissue explant is considered to be maintained in culture if it is viable. In some embodiments, the tissue explant is maintained in culture for 2, 4, 6, 8, 10 or 12 hours in culture. In some embodiments, the tissue explant is maintained in culture for 24 hours. In some embodiments, the tissue explant is maintained in culture for at least 2 days. In some embodiments, the tissue explant is maintained in culture for at least 3 days. In some embodiments, the tissue explant is maintained in culture for at least 4 days. In some embodiments, the tissue explant is maintained in culture for 1 week. In some embodiments, the tissue explant is maintained in culture for at least 1 week. In some embodiments, the tissue explant is maintained in culture for 2 weeks. In some embodiments, the tissue explant is maintained in culture for at least 2 weeks. In some embodiments, the tissue explant is maintained in culture for 3 weeks. In some embodiments, the tissue explant is maintained in culture for 4 weeks. In some embodiments, the tissue explant is maintained in culture for 5 weeks. In some embodiments, the tissue explant is maintained in culture for 6 weeks. In some embodiments, the tissue explant is maintained in culture for 7 weeks. In some embodiments, the tissue explant is maintained in culture for 8 weeks. In some embodiments, the tissue explant is maintained in culture for 9 weeks. In some embodiments, the tissue explant is maintained in culture for 10 weeks. In some embodiments, the tissue explant is maintained in culture for 11 weeks. In some embodiments, the tissue explant is maintained in culture for 12 weeks. In some embodiments, the tissue explant is maintained in culture for 13 weeks. In some embodiments, the tissue explant is maintained in culture for 14 weeks. In some embodiments, the tissue explant is maintained in culture for 15 weeks. In some embodiments, the tissue explant is maintained in culture for 16 weeks. In some embodiments, the tissue explant is maintained in culture for 17 weeks. In some embodiments, the tissue explant is maintained in culture for 18 weeks. In some embodiments, the tissue explant is maintained in culture for 18 weeks or more.

Analysis of Tissue Explant

As described supra, the tissues within the gastrointestinal tract comprise distinguishing features and cell types. In some embodiments, the architecture of the tissue explant is maintained in culture. In some embodiments, architecture is analyzed via microscopic evaluation. In some embodiments, electron microscopy is used to analyze architecture of the tissue explant. Electron microscopy includes, but is not limited to, transmission electron microscopy (TEM), scanning electron microscopy (SEM) and focused ion beam (FIB) microscopy. In some embodiments, the architecture of the tissue explant is evaluated by staining the tissue explant and observing it microscopically. Methods for staining tissue are known by those of skill in the art, and include, but are not limited to immunohistochemistry assays, immunofluorescence assays, and in situ hybridization assays. In some embodiments, the tissue explant is stained with hematoxylin and eosin (H&E). In some embodiments, the tissue explant is stained with Masson's Trichrome. Masson's Trichrome stains connective tissue, nuclei and cytoplasm. In some embodiments, the tissue explant is stained with Alcian blue. Alcian blue stains acid mucosubstances and acetic mucins.

Methods for identifying specific cell types are also known to one of skill in the art. For example, staining with an antibody which recognizes a specific marker of the cell type, or using a probe such as DNA/RNA for in situ hybridization. Immunohistochemical staining of the tissue explant is used to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of a polypeptide or against a synthetic peptide based on the DNA sequences encoding the polypeptide or against an exogenous sequence fused to a DNA encoding a polypeptide and encoding a specific antibody epitope.

Further, expression of proteins within the tissue explant can be determined. Assays for protein expression include, but are not limited to, ELISA (enzyme linked immunosorbent assay), SPR assays, immunoprecipitation assay, affinity chromatography, Western blots, RIA, "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

In some embodiments, the tissue explant is freshly isolated. In some embodiments, the tissue explant is frozen. In some embodiments, the tissue explant is formalin-fixed paraffin-embedded. In some embodiments, the tissue explant is lysed.

Substrates for the Tissue Explant

In some embodiments, the tissue explant described herein is placed on a substrate. Various culture substrates can be used in the methods and systems of the disclosure. Such substrates include, but are not limited to, glass, polystyrene, polypropylene, stainless steel, silicon and the like. In some embodiments, the substrate is poly(methyl methacrylate). In some embodiments, the substrate is a polycarbonate, acrylic copolymer, polyurethane, aluminum, carbon or Teflon (polytetrafluoroethylene). The cell culture surface can be chosen from any number of rigid or elastic supports. For example, cell culture material can comprise glass or polymer microscope slides. In some embodiments, the substrate may be selected based upon a tissue's propensity to bind to the substrate. In some embodiments, the substrate may be selected based on the potential effect of the substrate on the tissue explant (e.g., electrical stimulation/resistivity, mechanical stimulation/stress).

The cell culture surface/substrate can be made of any material suitable for culturing mammalian cells. For example, the substrate can be a material that can be easily sterilized such as plastic or other artificial polymer material, so long as the material is biocompatible. In some embodiments, the substrate is any material that allows cells and/or tissue to adhere (or can be modified to allow cells and/or tissue to adhere or not adhere at select locations). Any number of materials can be used to form the substrate/surface, including but not limited to, polyamides; polyesters; polystyrene; polypropylene; polylacrylates; polyvinyl compounds (e.g., polyvinylchloride); polycarbonate; polytetrafluoroethylene (PTFE); nitrocellulose; cotton; polyglyolic acid (PGA); cellulose; dextran; gelatin; glass; fluoropolymers; fluorinated ethylene propylene; polyvinylidene; polydimethylsiloxane; and silicon substrates (such as fused silica, polysilicon, or single silicon crystals), and the like. Also, metals (e.g., gold, silver, titanium films) can be used.

In some embodiments, the substrate may be modified to promote cellular adhesion (e.g., coated with an adherence material). For example, a glass substrate may be treated with a protein (i.e., a peptide of at least two amino acids) such as collagen or fibronectin to assist cells of the tissue in adhering to the substrate. In some embodiments, a single protein is adhered to the substrate. In some embodiments, two or more proteins are adhered to the substrate. Proteins suitable for use in modifying the substrate to facilitate adhesion include proteins to which specific cell types adhere under cell culture conditions.

The type of adherence material(s) (e.g., ECM materials, sugars, proteoglycans, etc.) deposited on the substrate will be determined, in part, by the cell type or types in the tissue explant.

In some embodiments, the substrate does not require adherence material. Prior gastrointestinal culture systems utilizing primary cells require exogenous extracellular matrix. In some embodiments, the tissue explant described herein does not require exogenous extracellular matrix.

In some embodiments, the substrate is a singular well plate. In some embodiments, the substrate is a multi-well plate or assembly. In some embodiments, the substrate comprises microwells. In some embodiments, the substrate comprises 6, 12, 24, 48, 96, 384 or 1536 microwells. In some embodiments, the substrate comprises 96 microwells. In some embodiments, the substrate comprises 384 microwells. In some embodiments, the substrate comprises 1536 microwells. In some embodiments, each microwell is completely covered by the tissue explant described herein.

Figure 2A:
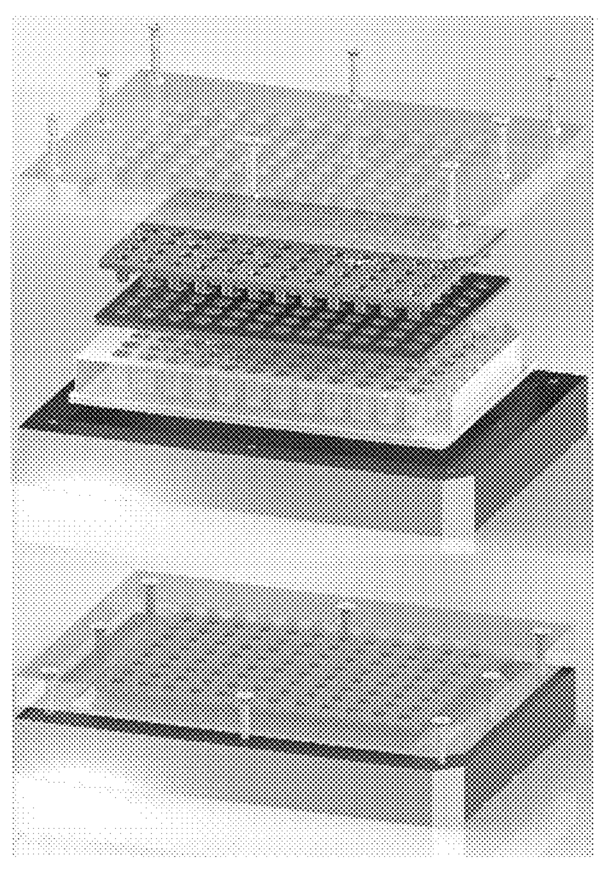
FIG. 2A is an image showing the schematic of the 96 well plate device set-up used for high-throughput assays.
Figure 2B:
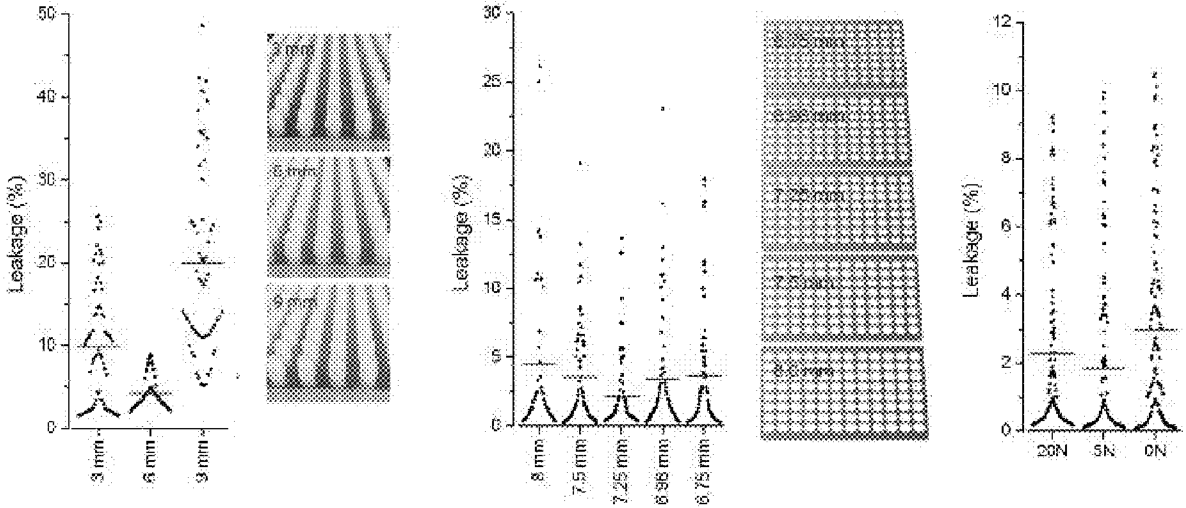
FIG. 2B provides graphs of the percent leakage between wells of various diameters (left and middle graphs) and with different compression forces (right graph). Data represents one leakage experiment, mean is represented by the line. n=96.
Figure 2C:
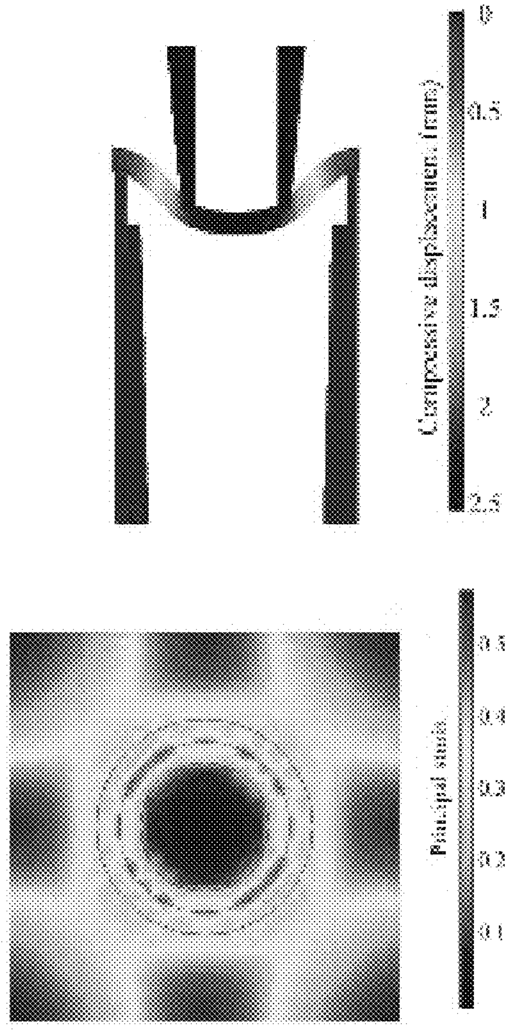
FIG. 2C shows the computational model of force and displacement on tissue as a function of well geometry and compression applied.
Figure 2D:
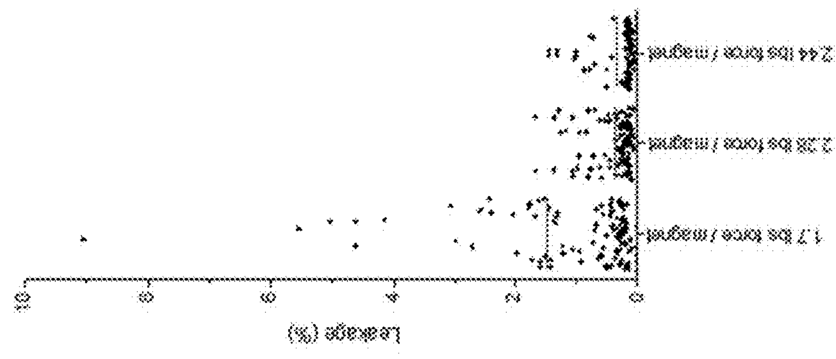
FIG. 2D provides graphs showing perfusion of FITC and FITC-Dextran 4 kDa over 50 minutes in a magnet-based interface system comprising small intestinal tissue explants (left), along with graphs showing FITC perfusion and well-to-well leakage dependent on magnet strength (right).
Figure 2D:
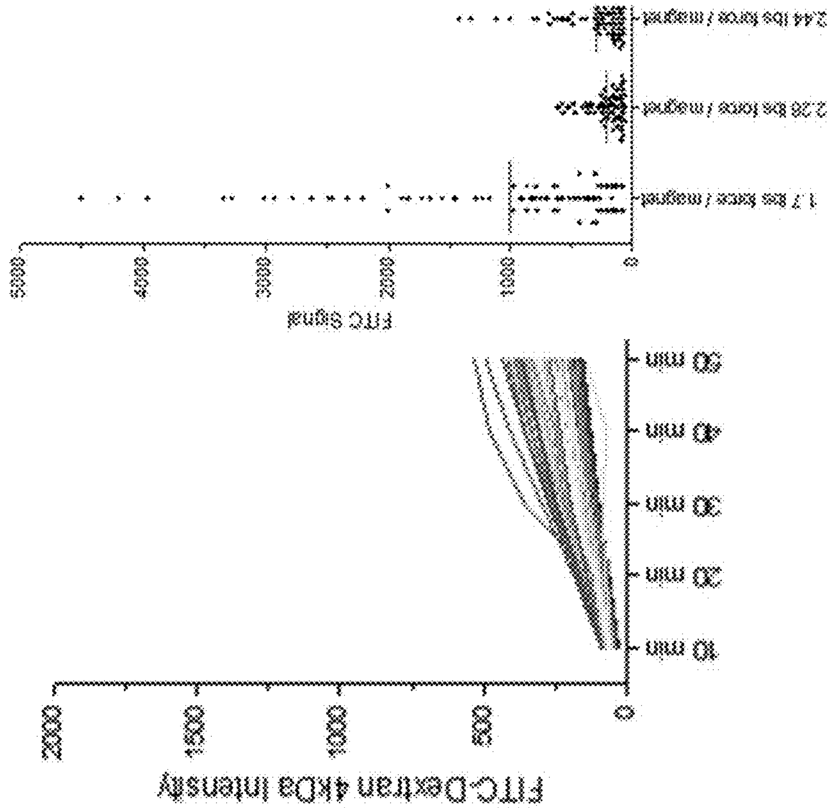
Figure 2D:
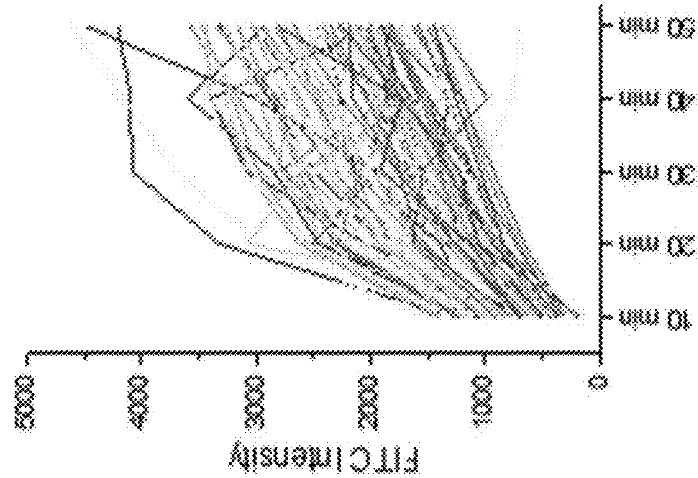
Figure 2E:
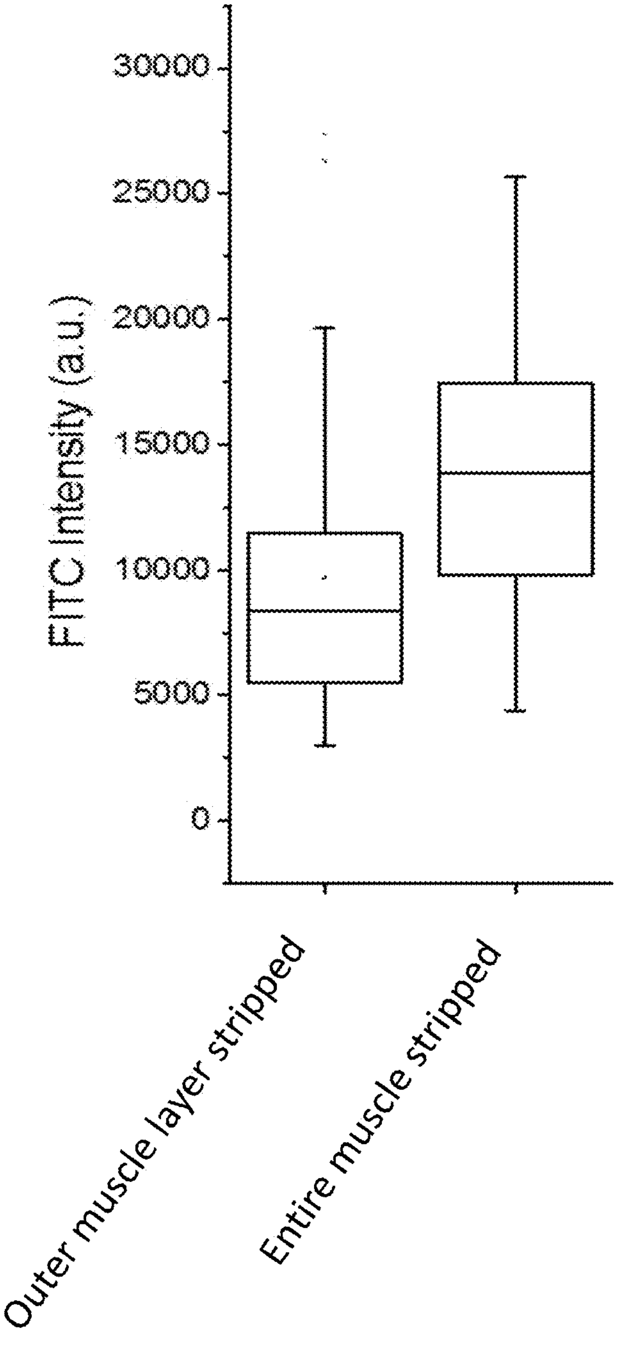
FIG. 2E is a graph depicting perfusion of fluorescein (FITC) through intestinal tissue explants with or without serosa and outer muscle layer. Relative standard deviation (a) shows the variability across 480 samples analyzed.
Figure 2F:
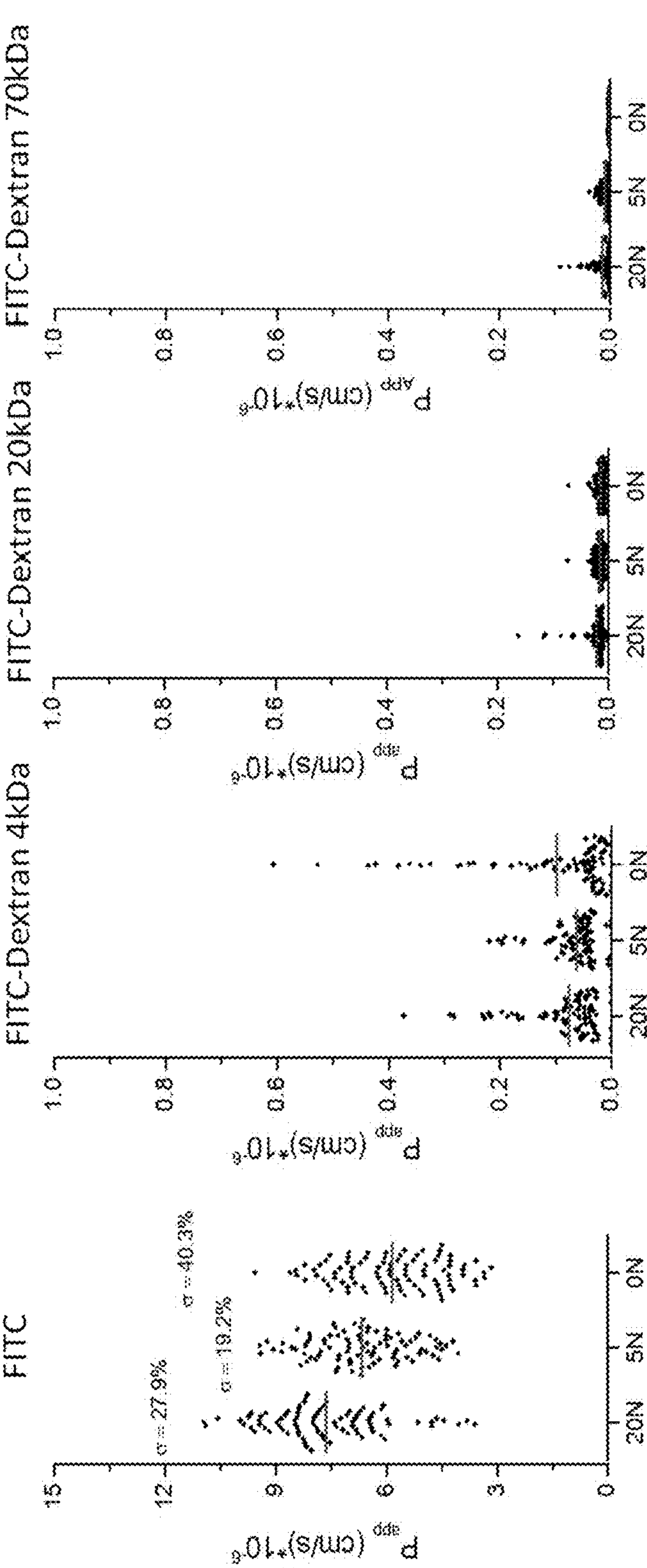
FIG. 2F provides graphs depicting effect of tissue compression on perfusion of various model drugs. Relative standard deviation (a) shows the variability across 100 samples form 3 different batches analyzed.
Figure 2G:
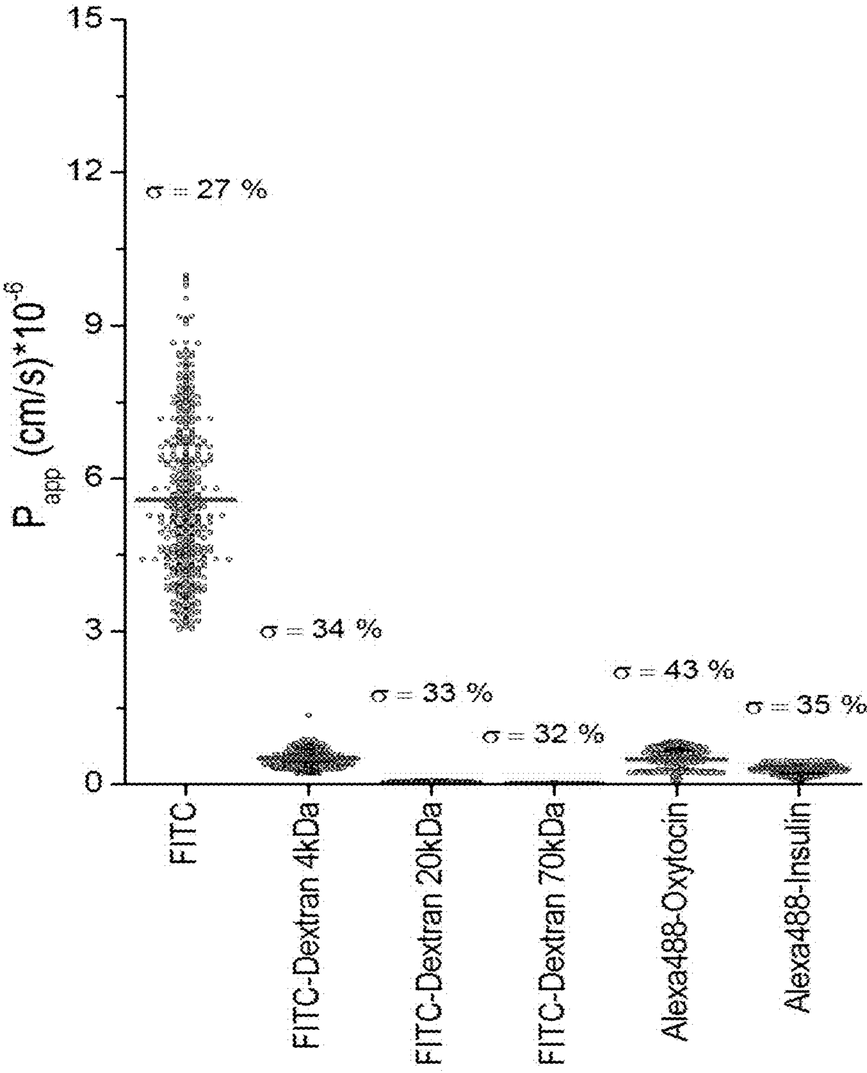
FIG. 2G is a graph depicting variability analysis of perfusion of various model drugs. Relative standard deviation (a) shows the variability across 500 samples each from 6 different animal batches.
Figure 2H:
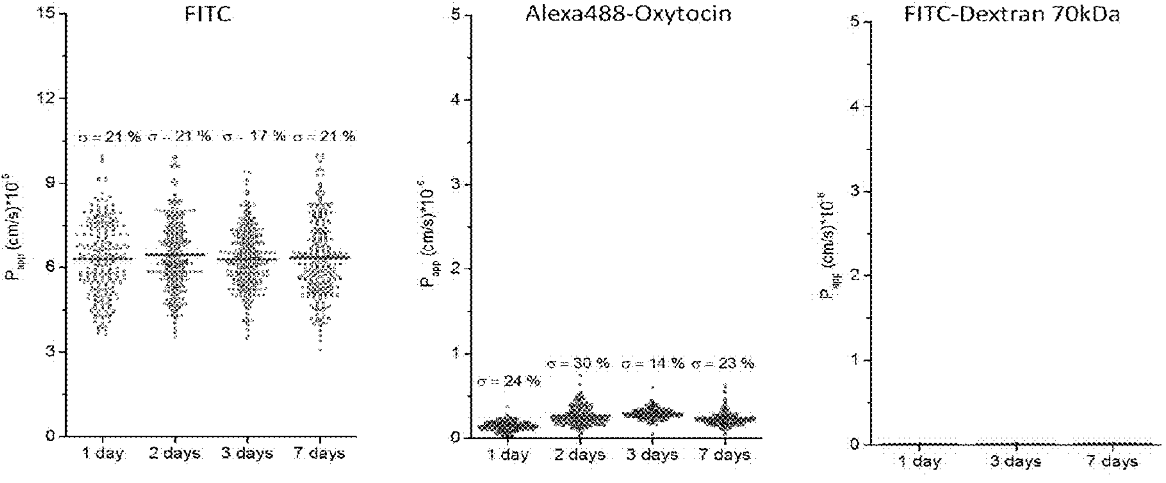
FIG. 2H provides graphs depicting variability analysis of perfusion of various model drugs conducted with the intestinal tissue explant incubated ex vivo for 1, 2 3 or 7 days prior to the experiment. Relative standard deviation (a) shows the variability across 500 samples each from 3 different animal batches.
Figure 2I:
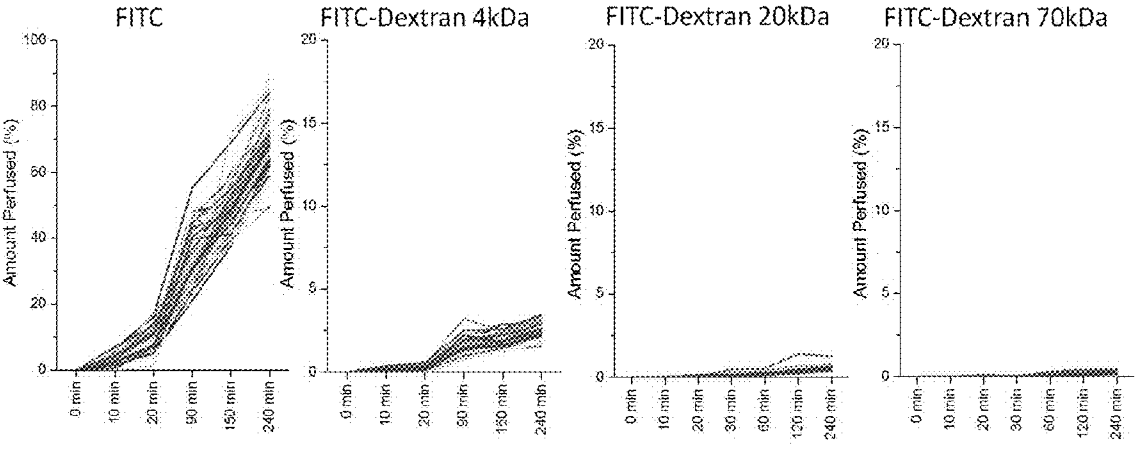
FIG. 2I provides line graphs of 96 individual intestinal perfusion time lapse analyses (over 2 hours) of various model drugs.
Figure 2L:
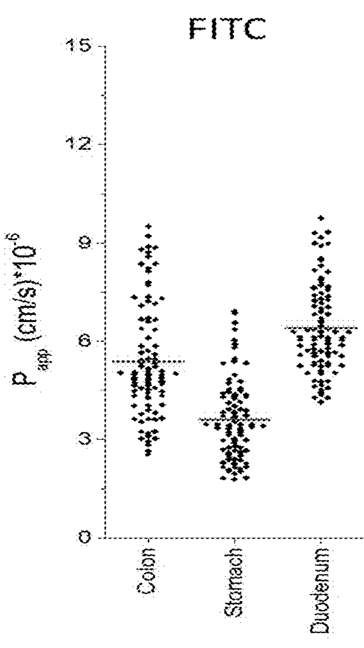
FIG. 2L provides graphs depicting variability analysis of perfusion of various model drugs in colon, duodenum and stomach tissue explants.
Figure 2L:
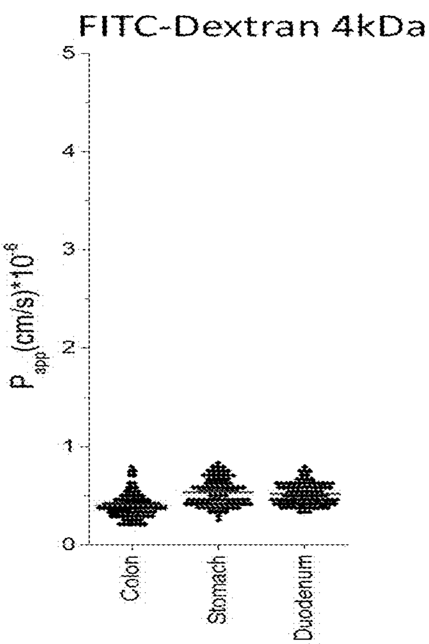
Figure 2M:
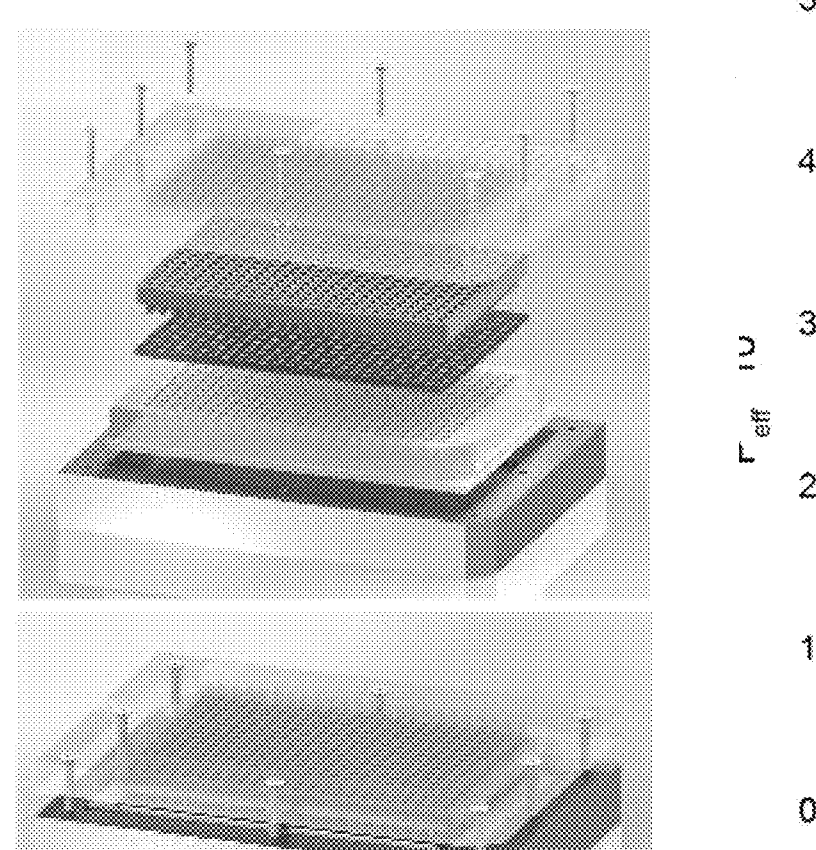
FIG. 2M is an image showing the schematic of the 384 well plate device set-up used for high-throughput assays.

In some embodiments, the tissue explant described herein is placed on an interface apparatus comprising a standard plate, a thin middle plate, and an upper load plate (see FIGS. 2A and 2M for exemplary setups). The tissue explant is placed over the through holes of the middle plate and the upper load plate is then placed onto the tissue explant to compress it onto the middle plate and around the through holes, while mounted on the standard plate. In some embodiments, each plate comprises 6, 12, 24, 48, 96, 384 or 1536 microwells.

In some embodiments, the upper load plate comprises posts having a diameter from 3 mm to 5 mm. In some embodiments, the upper load plate comprises posts having a diameter from about 3 mm to about 5 mm. In some embodiments, the upper load plate comprises posts having a diameter of 4 mm. In some embodiments, the upper load plate comprises posts having a diameter of about 4 mm. In some embodiments, the tissue explant placed on the middle plate is slightly recessed into each well by forces from the upper plate. In some embodiments, the middle plate thickness is 1 mm or 2 mm. In some embodiments, the middle plate thickness is about 1 mm or about 2 mm. In some embodiments, the middle plate thickness is 1 mm. In some embodiments, the middle plate thickness is about 1 mm. In some embodiments, the diameter of posts of the middle plate is larger than the diameter of the upper load plate to ensure the tissue explant rests between the upper and middle plate. In some embodiments, the middle plate comprises posts having a diameter from 6.5 mm to 8 mm. In some embodiments, the middle plate comprises posts having a diameter from about 6.5 mm to about 8 mm. In some embodiments, the middle plate comprises posts having a diameter of 6 mm. In some embodiments, the middle plate comprises posts having a diameter of about 6 mm.

In some embodiments, the pressure applied to the tissue explant minimizes well-to-well leakage. In some embodiments, the pressure applied to the tissue explant is 20N, 15N, 10N, or 5N. In some embodiments, the pressure applied to the tissue explant is about 20N, about 15N, about 10N, or about 5N. In some embodiments, the pressure applied to the tissue explant is 5N. In some embodiments, the pressure applied to the tissue explant is about 5N.

Figure 16:
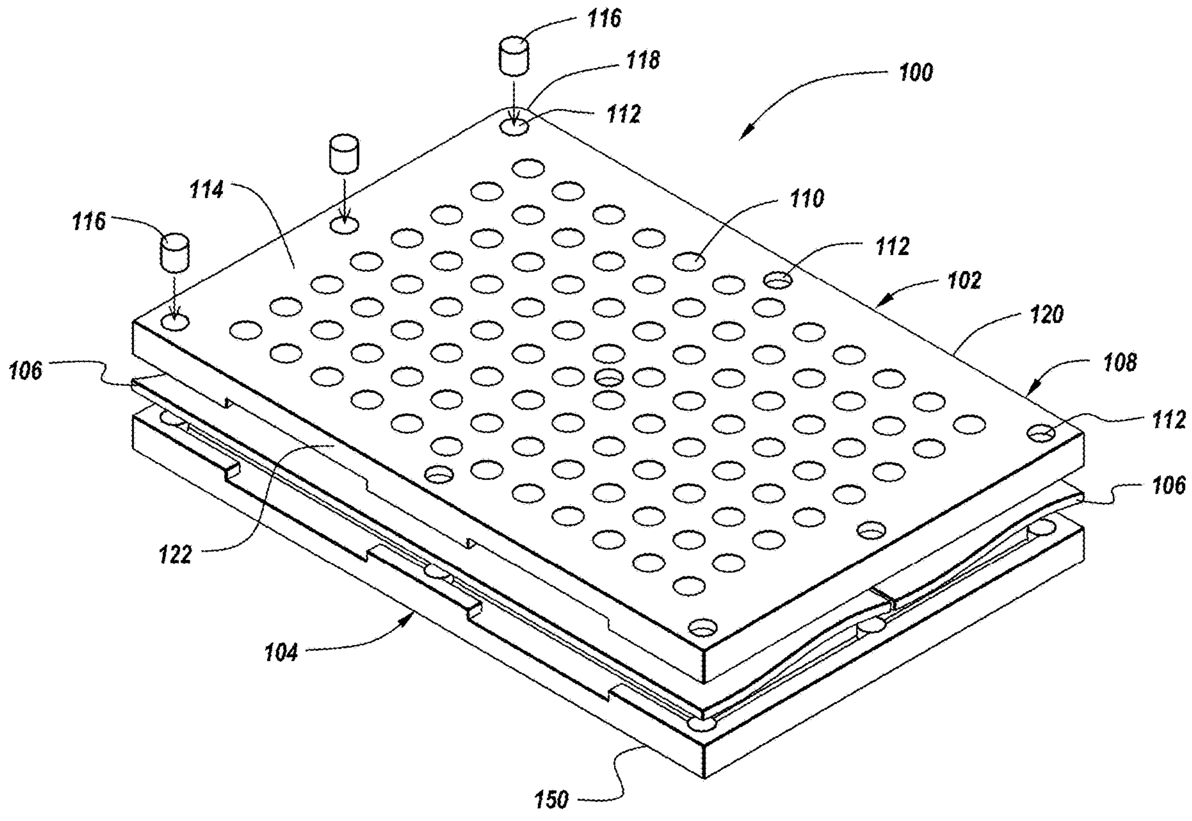
FIG. 16 is a schematic perspective view of another embodiment of the substrate or plate assembly of the present disclosure showing a tissue explant mounted therein.
Figure 17:
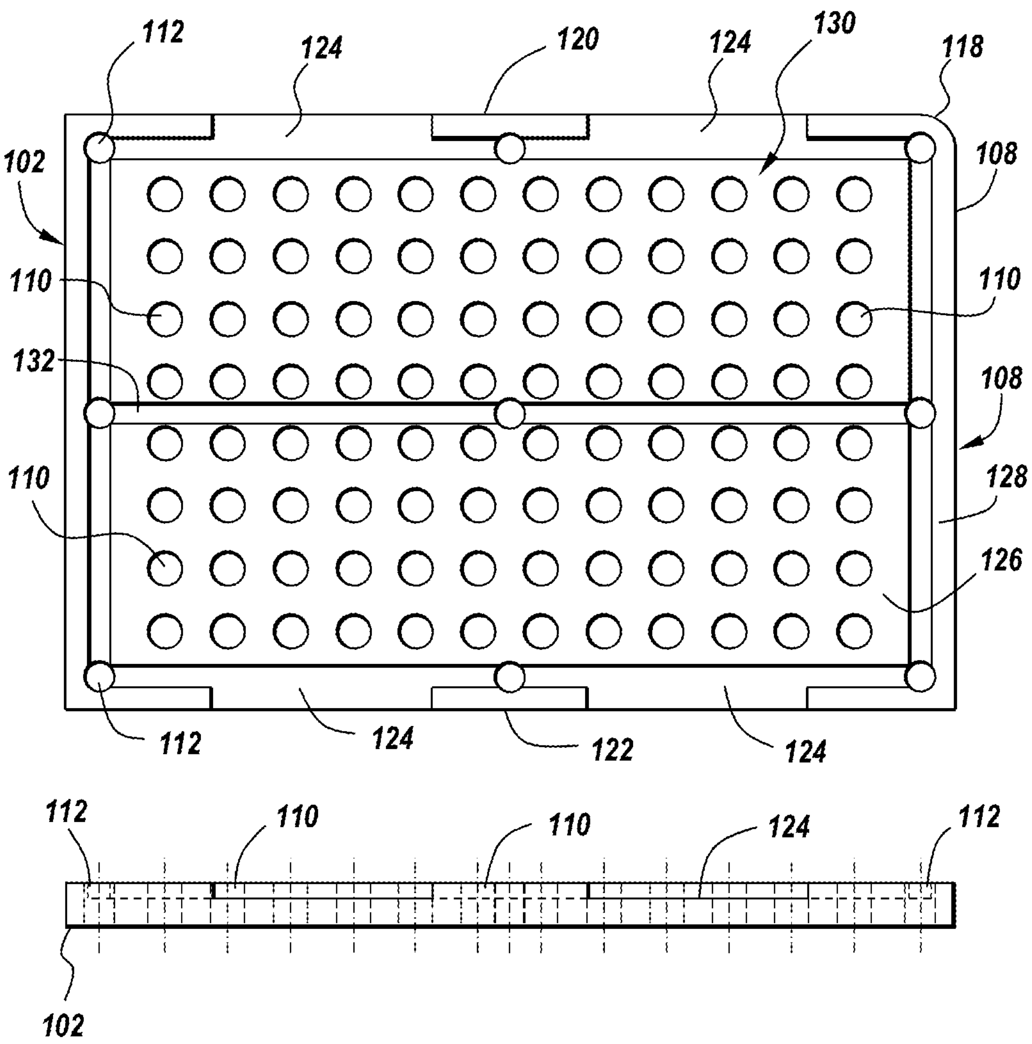
FIG. 17 is a bottom view of the top plate of the plate assembly of FIG. 16 according to the teachings of the present disclosure.
Figure 18:
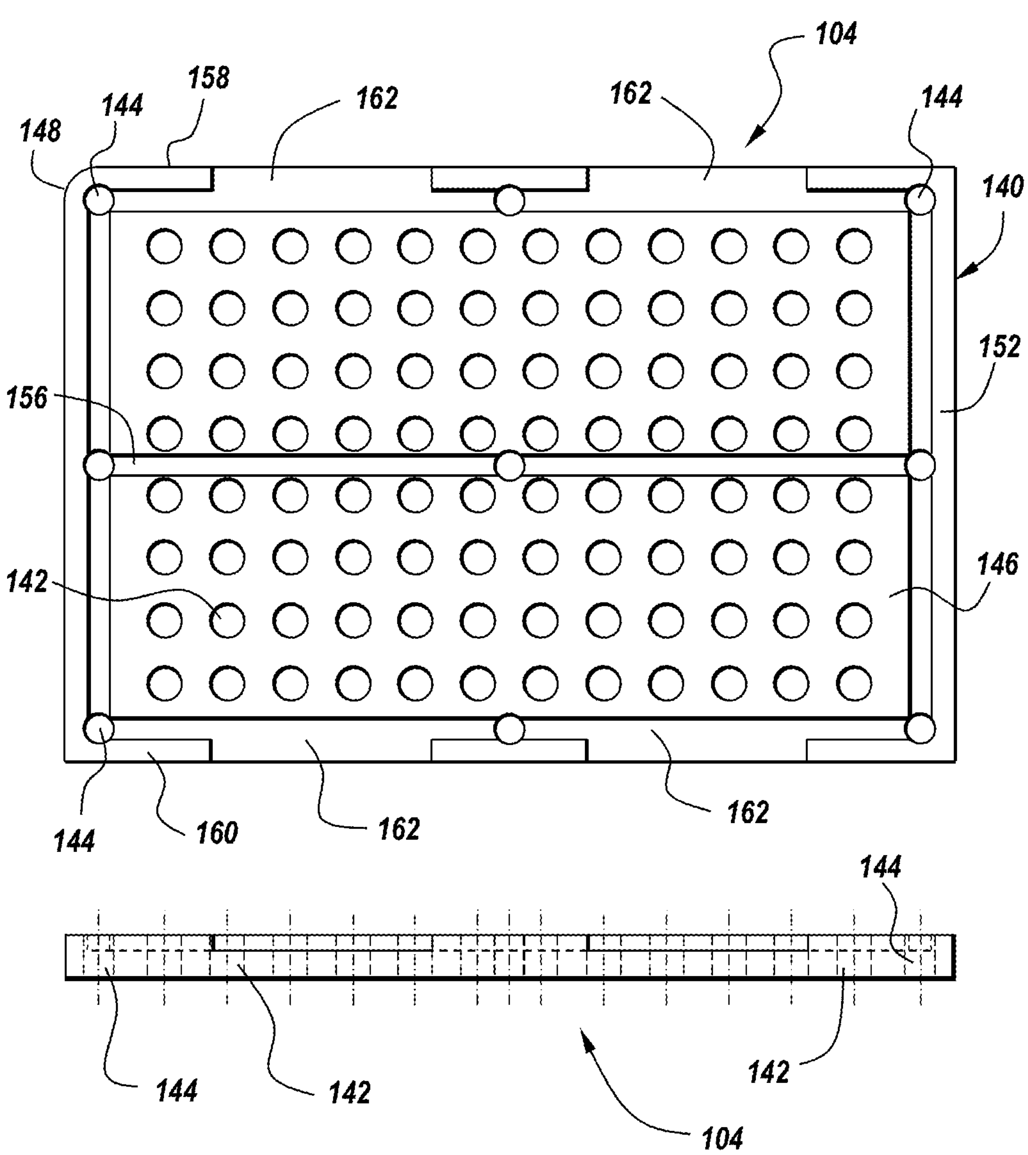
FIG. 18 is a top view of the bottom plate of the plate assembly of FIG. 16 according to the teachings of the present disclosure.

The present disclosure also contemplates the use of another embodiment of a substrate or plate assembly 100 suitable for use with the present disclosure, as shown in FIGS. 16 through 18. The substrate assembly 100 can be used in conjunction with a tissue explant as described herein. The tissue explant can include, for example, intestinal epithelium from a large, non-human, mammalian gastrointestinal tract, such as from the intestine of a porcine. The tissue explant can comprise a single layer or piece of tissue or can comprise multiple pieces or layers of tissue. The substrate assembly 100 of the present disclosure can form part of or can be used in conjunction with a conventional high-throughput drug absorption screening assay system (not shown). Conventional high throughput assay systems are known in the art and are well understood. The conventional assay systems can include a robotic arm (not shown) to grasp and manipulate the plate assembly during use.

The illustrated substrate assembly 100 of the present disclosure can comprise any selected number of plates and components. As illustrated, the substrate assembly 100 includes a top plate 102 and an opposed bottom plate 104. The tissue explant 106 is adapted to be disposed between the top and bottom plates. The top plate 102, as shown in FIGS. 16 and 17, includes a main body 108 having a plurality of microwells 110 formed therein, as is known in the art. The microwells 110 can comprise an array of microwells arranged in any selected configuration and can include any selected number of rows and columns, depending upon the total number of microwells desired to be formed in the plate. The microwells 110 can have any selected diameter as is known in the art. The main body 108 also has a plurality of apertures 112 formed in a top surface 114 thereof at selected locations. According to one practice, the apertures 112 are formed at selected locations in the plate 102, including about the peripheral region of the plate. Those of ordinary skill in the art will readily recognize that any selected number of apertures 112 can be formed therein and can be arranged in any selected configuration. According to a preferred embodiment, the apertures 112 are evenly distributed about the top surface 114 of the plate 102. The apertures 112 can be fastener receiving apertures for receiving and mounting known fasteners therein, such as screws, magnets and the like. According to a preferred embodiment, the apertures 112 are adapted to seat magnets 116 therein. The magnets 116 employed in connection with the top plate 102 can be any selected type of magnet having any selected strength, and preferably includes high strength magnets providing a selected amount of force, such as between about 1.7 lb force per magnet and about 2.5 lb force per magnet, and preferably about 2.28 lb force per magnet. Those of ordinary skill in the art will readily recognize that the magnet strength can be selected as a function of the force needed to place the tissue explant in fluid sealing contact with the top and bottom plates. The force applied by the magnets when mounted within the top and bottom plates can be structured such that only tissue not within the area of the reaction well is exposed to compressive forces.

The main body 108 of the top plate 102 has a generally quadrilateral shape, and preferably has a rectangular shape. According to one practice, the main body 108 can optionally have three corners forming substantially right angles and a fourth corner 118 that is rounded. The rounded corner 118 provides a visual indicator to the user or to the assay system of the orientation of the substrate assembly 100.

The illustrated top plate 102 has a bottom surface 126 that has a rim portion 128 formed along the peripheral portion or edge of the plate and extending outwardly therefrom. The rim portion 128 thus forms a chamber or recess 130 therein. The bottom surface 126 of the plate 102 also has an optional ridge portion 132 formed along a central portion of the bottom surface and extending outwardly therefrom. The ridge portion 132 if present can thus divide the recess 130 into a plurality of subchambers, each subchamber adapted to seat a tissue explant. The rim portion 128 also has formed therein along opposed sides 120 and 122 of the main body selected cut-out features 124. The cut-out features 124 are formed therein to provide a space or region for a user to manipulate the plates so as to place them together or to pull them apart. Further, the cut-out features allow a robotic arm of an assay system to manipulate the substrate assembly by coupling to the assembly via the cut-out features.

The bottom plate 104 of the substrate assembly 100 is shown in FIGS. 16 and 18. The bottom plate 104 is structured in a manner similar to the top plate 102. The illustrated bottom plate 104 has a main body 140 having a plurality of microwells 142 formed therein, as is known in the art. The microwells 142 can also be arranged as an array of microwells in any selected configuration and can include any selected number of rows and columns, depending upon the total number of microwells desired to be formed in the plate 104. The number of microwells 142 in the bottom plate preferably matches the number of microwells 110 formed in the top plate 102. The microwells 142 can have any selected diameter as is known in the art. The main body 140 also has a plurality of apertures 144 formed in a top surface 146 thereof at selected locations. The main body also has an opposed bottom surface 150. According to one practice, the apertures 144 are formed at selected locations in the bottom plate 104, including about the peripheral region of the plate. Those of ordinary skill in the art will readily recognize that any selected number of apertures 144 can be formed therein and can be arranged in any selected configuration. According to a preferred embodiment of the disclosure, the apertures 144 are evenly distributed about the top surface 146 of the bottom plate 104. The apertures 144 can be formed as fastener receiving apertures for receiving and mounting known fasteners therein, such as screws, magnets and the like. According to a preferred embodiment, the apertures 144 are adapted to seat magnets 116 therein. The magnets 116 mounted in the top plate 102 and the bottom plate 104 help magnetically retain or secure the plates together according to known techniques.

The main body 140 of the bottom plate 104 also has a generally rectangular shape. According to one practice, the main body can optionally have three corners forming substantially right angles and a fourth corner 148 that is rounded. The rounded corner 148 provides a visual indicator to the user or to the assay system of the relative orientation of the substrate assembly 100.

The top surface 146 of the bottom plate 104 also has a rim portion 152 formed along the peripheral portion or edge of the plate and extending outwardly therefrom. The rim portion 152 thus forms a chamber or recess 154 therein. The top surface 146 of the plate 104 also has an optional ridge portion 156 formed there along and extending outwardly from the top surface. The ridge portion 156 if present can thus divide the recess 130 into a plurality of subchambers, each subchamber adapted to seat a tissue explant. The rim portion 152 also has formed therein along opposed sides 158 and 160 of the main body selected cut-out features 162. The cut-out features 162 are similar to the cut-out features 124 of the top plate and are formed therein to provide a space or region for a user to manipulate the plates so as to place them together or to pull them apart. Further, the cut-out features allow a robotic arm of an assay system to manipulate the substrate assembly by coupling to the assembly via the cut-out features 124, 162.

The top plate 102 and the bottom plate 104 can be formed from any selected material, and is preferably formed from a material that is biologically compatible with the tissue explant while concomitantly having high mechanical strength and having a relatively low weight. Examples of materials suitable for use as the top and bottom plates 102, 104 includes polyurethane, polycarbonate, acrylic, aluminum, titanium, polytetrafluoroethylene (PTFE), glass, and polystyrene. The plates can also have any selected color so as to better identify the plates relative to each other. Further, having different color plates enables different information read-out abilities, such as by employing known bioluminescence and fluorescence techniques. Although the substrate assembly 100 is illustrated as employing a pair of plates 102, 104, those of ordinary skill in the art will recognize that additional components, layers, or plates can also form part of the assembly.

When the tissue explant 106 is placed between the top plate 102 and the bottom plate 104, the tissue explant 106 is placed in planar contact with the microwells of the plates, thereby providing a top luminal surface and a bottom basolateral surface of the tissue explant. The tissue explant 106 seats within the recess or chambers 130, 154 formed in the plates. The magnets 116 mounted within the top and bottom plates help magnetically align the plates to each other, thus capturing and retaining the tissue explant there between. The compressive force formed by the magnets to the tissue explant is formed or focused on the non-microwell areas or regions of the tissue explant, thus avoiding well-to-well leakage of a solution applied to the explant via the microwells of the top plate 102.

The tissue explant can be formed as a single piece that is adapted to cover the entire array of microwells or can be formed in multiple pieces that are adapted to cover the entire array of microwells. If the tissue explant is formed as a single piece, then the optional ridge portions 132, 156 of the top and bottom plates, respectively, can be omitted.

According to aspects of the present disclosure, the plates 102, 104 of the substrate assembly 100 as described herein include a selected number of microwells (e.g., such as 6, 12, 24, 48, 96, 384 or 1536 microwells). In further aspects of the disclosure, each microwell of the array of microwells formed in each plate is completely covered by a selected surface of the tissue explant when secured or retained between the plates.

According to other aspects of the present disclosure, the substrate assembly is suitable for use in a high-throughput drug absorption screening assay system, where the tissue explant is disposed in relatively planar contact with the microwells of the plates, thereby providing a luminal surface and a basolateral surface for allowing measurement of absorption of a drug through the tissue explant. In other aspects of the present disclosure, the substrate assembly is suitable for use in a high-throughput absorption-dissolution screening assay system, where the tissue explant is disposed in relatively planar contact with the microwells of the plates, thereby providing a luminal surface and a basolateral surface for allowing measurement of absorption of a drug through the tissue explant before or after measuring the dissolution of the drug.

In further aspects of the present disclosure, the substrate assembly is suitable for use in a high-throughput toxicity screening assay system, wherein the tissue explant is disposed in relatively planar contact with the microwells of the plates, thereby allowing for measurement of toxicity on the tissue explant. In yet further aspects of the present disclosure, the substrate assembly is suitable for use in a high-throughput GLP-1 stimulation screening assay system, wherein the tissue explant is disposed in relatively planar contact with the microwells of the plates, thereby providing a luminal and a basolateral surface for allowing measurement of GLP-1 secretion from the tissue explant.

According to still other aspects, the present disclosure also provides methods for determining absorption of a test compound through the tissue explant when placed in the substrate assembly. The method involves contacting the tissue explant with a test compound supplied through the microwells 110 of the top plate 102. The top surface of the tissue explant forms a luminal surface and a bottom surface of the tissue explant forms a basolateral surface. The method also includes the steps of determining absorption of the test compound by detecting the presence of the test compound at the luminal surface and at the basolateral surface. The presence of the test compound at the basolateral surface indicates the ability of the compound to be absorbed through the tissue explant. In some aspects, detecting the presence of the test compound comprises determining concentration of the compound at the luminal and basolateral surfaces. A similar methodology can also be used to determine the perfusion rate of the test compound over time. In some aspects, the method further comprises determining the dissolution of the test compound.

Methods of Making an In Vitro Cellular Composition

In some aspects, the disclosure provides an in vitro cellular composition comprising a substrate as described herein, and a tissue explant as described herein, wherein the tissue explant is contacted with the substrate.

In some embodiments, the tissue explant is in planar contact with the substrate. Planar contact can be determined by standard methods known to those of skill in the art. For example, a solution comprising a marker (e.g., fluorophore or colored compound) is added to the tissue explant when in contact with the substrate. The solution stains the surface of the tissue and enables detection of the tissue via photographic inspection, spectrophotometrics, or via laser scanner based techniques. If there is no significant difference in variability of the stain within the tissue explant in contact with the substrate, compared to an equivalent area of non-mounted tissue completely immersed in the solution, then the tissue explant is in planar contact with the substrate. In some embodiments, the substrate comprises a plurality of microwells. Accordingly, the solution comprising a marker can be placed within the microwells and a comparison between stain within the microwell and non-mounted tissue is carried out.

In some embodiments, planar contact is determined by coating the surface of a substrate with a marker prior to contacting it with the tissue explant, and analyzing the distribution of the marker. For example, the entire area of the substrate facing the tissue is coated with a marker that forms a uniform layer on the surface of the substrate. This coating stains the tissue when placed in close contact, and the resulting stain on the tissue remains intact after the substrate and tissue are separate. The resulting stain is analyzed by visual inspection, and if a regular pattern of markings corresponding to the substrate set-up is observed, the tissue explant is in planar contact with the substrate. In some embodiments, the substrate comprises a plurality of microwells and therefore the stain on the tissue can correlate with the microwell set-up.

In some embodiments, the substrate comprises a plurality of microwells, and upon contact with the tissue explant, each microwell is completely covered by the tissue explant. In some embodiments, well-to-well leakage is minimized in the in vitro cellular composition. In some embodiments, complete coverage of the tissue explant by each microwell in a substrate minimizes well-to-well leakage.

In some embodiments, an in vitro cellular composition comprising a substrate with a plurality of microwells has low sample variability between microwells. Sample variability can be determined by standard methods known to those of skill in the art. For example, analysis of the perfusion of a drug can be determined in each microwell of the substrate and compared to determine sample variability.

In some embodiments, the tissue explant is contacted to the substrate immediately after it is excised from the gastrointestinal tract. In some embodiments, the tissue explant is kept in a first container (e.g., a cell strainer) for a period of time before being contacted to the substrate. In some embodiments, the properties of the tissue explant described herein are maintained when kept in a first container prior to contact with the substrate.

In some embodiments, the in vitro cellular composition is maintained for 24 hours, 2 days, 3 days, 1 week, 2 weeks, 3 weeks, 4 weeks or more, prior to being used in the methods described herein.

Methods of Use

A. Predicting or Determining Drug Absorption and Oral Availability

In some aspects of the disclosure, the tissue explant described herein is useful for predicting the absorption of a compound or composition of interest. In further aspects of the disclosure, the tissue explant described herein is useful for predicting the oral availability of a compound or composition of interest.

The small intestine is an important site for the absorption of pharmacological agents. The proximal part of the small intestine has the greatest capacity for absorption of drugs. The current standard for predicting drug absorption is the CaCo-2 monolayer model. However, there are many defects in this model system. The CaCo-2 model lacks the intestinal mucus layer, metabolic enzymes, and extracellular matrix, along with the architecture and various cell types found in vivo. Moreover, CaCo-2 cells are heterogeneous human epithelial colorectal adenocarcinoma cells, which by their nature are very different compared to primary cells with regard to cell behavior (e.g., protein/gene expression, continuous cell division, and cell-cell adhesion complexes). Other systems have been developed to overcome the defects in the CaCo-2 system and are described (Dedhia, P., et al. Gastroenterology 2016; Vol. 150: 1098-1112; Ranga, A., et al. Advanced Drug Delivery Reviews 69-70 2014; 19-28; Shamir, E. and Ewald, A., Nature Reviews: Molecular Cell Biology 2014; Vol. 15: 647-664, Ootani, A., et al. Nature Medicine 2009 June; Vol. 15(6): 701-706).

However, these systems still fail to fully recapitulate the complex in vivo architecture and function of the gastrointestinal tract (e.g., small intestine). The tissue explant described herein provides significant advantages over the current model systems. For example, as discussed supra, the tissue explant described herein maintains the in vivo architecture of the gastrointestinal tract (e.g., small intestine) from which it was derived. In addition, the tissue explant comprises the components necessary for drug absorption (e.g., drug metabolizing enzymes, drug transporters). The tissue explant described herein can also be maintained in culture for long periods of time, unlike previously developed systems. Further, the tissue explant described herein does not require exogenous factors for maintenance in culture. Moreover, as discussed infra, the tissue explant described herein can be used for high-throughput screening. These characteristics highlight the improvements over prior model systems.

The tissue explant described herein provides a model system for testing and predicting drug absorption of a compound of interest. Effective drug therapy relies on the interplay between the pharmacokinetics and pharmacodynamics (PK/PD) of the compound upon administration. During the initial stages of drug discovery, numerous studies are performed to assess the pharmacological effectiveness of new chemical entities (NCEs) to select a lead compound(s) that offers the greatest promise for therapeutic efficacy. While the ability of a drug to bind to a therapeutic target is critical to its clinical success, the ultimate effectiveness is also a function of its ability to reach the therapeutic target in sufficient concentrations to mitigate or treat the ailment. Therefore, the pharmacokinetics of any NCE must also be evaluated early in the drug discovery stages to enhance the rational selection of a lead compound from the many NCEs that are screened, based on not only biological activity but also potential in vivo bioavailability. Bioavailability is defined by the US FDA as "the rate and extent to which the active ingredient or active moiety is absorbed from a drug product and becomes available at the site of action" (21 CFR 320.1(a)). The overall bioavailability is largely determined by the absorption, distribution, metabolism, and excretion of selected compounds in targeted patient populations. Absorption across intestinal epithelium is especially important. The tissue explants described herein offer a unique tool for measuring absorption rates of candidate agents. Similarly, tissue explants described herein are useful for screening for agents that modulate digestive enzymes.

In some aspects of the disclosure, drug absorption is predicted by determining the perfusion of a compound of interest through the tissue explant. Specifically, a compound of interest is added to the tissue explant followed by detection of the compound at both the basolateral and luminal surfaces of the tissue. Presence of the compound at the basolateral surface indicates the ability of the compound to perfuse through the tissue explant, thereby predicting drug absorption and oral bioavailability. A person of ordinary skill in the art can readily determine the concentration of a compound using a variety of methods, for example, spectrophotometric analysis, high performance liquid chromatography with spectrophotometric detection or liquid chromatography-mass spectrometry. In some embodiments, the candidate agent is radiolabeled, allowing for detection in the receiver chamber and within the tissue.

In some embodiments, the disclosure provides methods for determining the concentration of a test compound in a tissue explant described herein. In some embodiments, a tissue explant is contacted with a compound of interest, and the presence of the compound within the tissue explant is determined. In some embodiments, concentration of the compound within the tissue explant is determined using high content confocal analysis. In some embodiments, a test compound comprises a fluorescence signal, and concentration of the compound can be measured with an excitation source (e.g., fluorescence emission detector). Specifically, the amount of fluorescence signal about excitation corresponds to the concentration of the compound within a tissue explant.

In some embodiments, the disclosure provides methods for analyzing the effect of drug-food interactions on absorption of a test compound. Specifically, a tissue explant is contacted with a compound of interest and digested food. In some embodiments, a tissue explant is contacted simultaneously with the compound of interest and digested food. In some embodiments, the compound of interest is contacted with the digested food prior to contact with the tissue explant. In some embodiments, the tissue explant is contacted with the digested food prior to contacting the tissue explant with a compound of interest. In some embodiments, the effect of drug-food interactions is determined utilizing native intestinal media derived from the animal in which the tissue explant was derived. In some embodiments, the effect of drug-food interactions is determined using native intestinal media and the ex vivo microbiome from the animal in which the tissue explant was derived. In some embodiments, the compound of interest is solubilized in the native intestinal media prior to contacting the tissue explant with the compound of interest. In some embodiments, determining the effect of drug-food interactions on absorption of a test compound comprises determining the difference in absorption between a compound of interest in the presence or absence of the digested food.

In some embodiments, the disclosure provides methods for analyzing absorption of a test compound over time (i.e., time-lapse analysis). In some embodiments, the disclosure provides methods for determining the perfusion rate of a test compound through a tissue explant. To determine the perfusion rate and/or time-lapse analysis, the tissue explant is contacted with a compound of interest, and the presence and/or concentration of the compound at the donor (e.g., luminal) and receiver (e.g., basolateral) surfaces is measured at different time points. In some embodiments, the presence and/or concentration of the compound is measured continuously.

In some embodiments, the disclosure provides methods for determining the effect of a drug transporter and/or metabolizing enzyme on absorption of a test compound. In some embodiments, effect of a drug transporter and/or metabolizing enzyme is determined by modifying expression of a drug transporter and/or metabolizing enzyme in a tissue explant described herein, contacting the tissue explant with a compound of interest, determining absorption of the compound, and comparing absorption of the compound in a tissue explant with and without a modified drug transporter and/or metabolizing enzyme. Methods for modifying expression of the drug transporter and/or metabolizing enzyme are described infra. In some embodiments, the drug transporter is MDR-1. In some embodiments, the metabolizing enzyme is CYP3A4.

In some embodiments, the disclosure provides methods for determining the anatomical site of drug absorption. Using the methods described herein, comparison of absorption of a test compound between different tissues from the gastrointestinal tract (stomach, jejunum, ileum, etc.) is predicative of where drug absorption occurs in vivo.

B. Predicting or Determining Gastrointestinal Toxicity

In some aspects of the disclosure, the tissue explant described herein is useful for predicting the gastrointestinal toxicity of a compound or composition of interest. In further aspects of the disclosure, the tissue explant described herein is useful for predicting the reduction of gastrointestinal toxicity of a formulation comprising a compound or composition of interest.

Gastrointestinal side effects are common in virtually all orally administered drugs. Most of those side effects are self-limiting, however certain drugs can cause more serious gastrointestinal side effects such as ulcer formation or bleeding, and in a small percentage of patients it can be life threatening. These toxic effects remain mainly a "silent epidemic", with many physicians and most patients unaware of the magnitude of the problem. It is estimated that gastrointestinal side effects account for 20-40% of drug induced adverse effects (DIAE). DIAE account for 100,000 deaths per year in the USA and account for 5% of all hospital admissions. Even just NSAIDs prescribed to rheumatoid arthritis and osteoarthritis patients is estimated to cause 16,500 deaths per year in the U.S. because of gastrointestinal side effects. Co-formulation of NSAIDs with proton pump inhibitors is currently the only way to prevent or manage NSAID induced gastric ulcers. However, the effectiveness of this strategy is limited, as it is only applicable to drug induced damage within the stomach and limited to only certain drugs. Ways to lower the gastrointestinal side effects of existing drugs are needed but challenges to test for local gastrointestinal toxicity form a major barrier.

Currently, preclinical evaluation of drug toxicity is performed in animal models. The predictability of human toxicity of large animal models is estimated to be around 60-70% overall, and specifically for gastrointestinal tissue toxicity around 85%. Rodent animal models show a significantly lower concordance with the observed human toxicity of around 50%. While large animal models appear to predict human gastrointestinal toxicity very well, they are confined to a low sample throughput because of high cost in terms of time, resource consumption and animal usage in addition to ethical considerations. Therefore, gastrointestinal toxicity testing is limited to validation of pharmaceutical compounds at the end of the pre-clinical drug discovery phase as part of the regulatory safety assessment before entering clinical studies.

Traditional in vitro cytotoxicity assays enable quantitative high-throughput sample screening and have made significant impact in mechanism of action identification and generation of highly robust datasets that enhanced the simplicity and effectiveness of machine learning and predictive model construction. However, current cell based in vitro assays are predominantly based on two-dimensional cell environments that do not account for the three-dimensional tissue architecture as well as the complex cell-cell and extracellular matrix-cell interactions. As a result, biomedical research has moved towards the use of three-dimensional models which can more accurately replicate some of these aspects with various success. Most of these in vitro assays are based on using tumor derived model cells that show a very different behavior compared to primary cells, but are easier to culture compared to primary cells derived from the gastrointestinal epithelium.

For modelling drug-gastrointestinal tissue interaction, the tissue architecture dictates the cellular drug exposure by tissue barrier function and the mucus layer. The tissue explant described herein overcomes this limitation.

In some embodiments, the gastrointestinal toxicity of a compound or composition of interest is determined by: contacting the tissue explant described herein with the compound or composition; waiting a sufficient period of time; and conducting a toxicity assay. Methods for analyzing the toxicity of a compound or composition are known to those of skill in the art and further described herein. For example, in some embodiments, the toxicity assay is a resazurin-based viability assay. Resazurin is an oxidation-reduction indicator, wherein it is irreversibly reduced to the pink colored and highly red fluorescent resorufin in metabolizing cells. In some embodiments, the toxicity assay is a Live/Dead assay. In some embodiments, the toxicity assay is an alamarBlue® assay. In some embodiments, toxicity is determined by measuring the protein expression of apoptosis markers, such as cleaved caspase 3 and cleaved lamin A/C. In some embodiments, toxicity is determined by measuring the protein expression of DNA damage markers, such has histone H2A phosphorylation. Methods for analyzing protein expression are known to those of skilled in the art and described herein.

C. Predicting or Determining Endocrine Stimulation

In some aspects of the disclosure, the tissue explant described herein is useful for identifying compounds or compositions that induce endocrine stimulation. For example, in some embodiments, the tissue explant responds to glucagon-like peptide 1 (GLP-1) inducing stimulants. In some embodiments, the tissue explant comprises enteroendocrine cells which secrete GLP-1 upon stimulation.

The gastrointestinal endocrine system, also known as the enteric endocrine system, controls and/or regulates a variety of processes, such as food intake, energy metabolism and endocrine balance. The gastrointestinal tract is the largest endocrine organ in the body, and the relationship between the gastrointestinal tract and the endocrine system is multidirectional, wherein hormones released by traditional endocrine organs can also regulate gastrointestinal function.

GLP-1 is a gastrointestinal hormone that lowers postprandial glucose concentrations by regulating pancreatic islet-cell function, with stimulation of glucose-dependent insulin and suppression of glucagon secretion. It has also been suggested that GLP-1 directly stimulates hepatic glucose uptake and suppressed hepatic glucose production, thereby adding to reduction of fasting and postprandial glucose levels. GLP-1 receptor agonists, which mimic the effects of GLP-1, have been developed for the treatment of type 2 diabetes. Accordingly, agents that stimulate GLP-1 secretion may be useful for treating type 2 diabetes and/or metabolic disease in general, including diabetes.

Methods for assessing GLP-1 secretion by the tissue explant in response to an agent can be determined by methods known to those of skill in the art. For example, supernatant of the tissue explant can be analyzed by ELISA or mass spectrometry for the presence of GLP-1. In some embodiments, comparison of the GLP-1 values obtained before and after the tissue explant is contacted with the agent indicates whether the agent stimulates GLP-1 secretion.

D. Screening Methods

In some aspects of the disclosure, candidate drug formulations are screened for their ability to be absorbed by the tissue explant described herein. The effect of a formulation is determined by adding the compound of interest in combination with a formulation to the tissue explant described herein, and measuring the concentration of the compound on either side of the tissue explant. The presence of the compound on the basolateral side indicates the compound perfused through the tissue explant.

In some aspects, the dissolution of a drug is determined in conjunction with an absorption screen. For example, in some embodiments, a method for measuring absorption and dissolution simultaneously comprises: (1) combination of drug+solvent to form a drug solution; (2) evaporation of the solution to form a drug powder; (3) combination of the drug powder with an excipient library; (4) spectrophotometric detection of drug concentration in supernatant to obtain dissolution data; (5) contacting the intestinal tissue explant with the supernatant; and (6) spectrophotometric detection of perfused drug concentration. Upon analysis, formulations that enhance dissolution and absorption can be identified.

In some embodiments, the dissolution of a known drug with poor solubility with or without poor permeability is enhanced based on the absorption and dissolution screening assays described supra.

In further aspects, candidate agents are screened for their toxicity effect. The tissue explant is exposed to the candidate agent or vehicle, and its viability, maintenance in culture and architecture is assessed. In some embodiments, a toxic agent decreases viability. In some embodiments, a toxic agent decreases the time in which the tissue explant is maintained in culture. In some embodiments, a toxic agent modifies the architecture of the tissue explant.

The tissue explant described herein is capable of analyzing gastrointestinal toxicity with higher in vivo predictability compared to conventional in vitro assays. In some aspects, the tissue explant is used as a screening platform to predict gastrointestinal toxicity and/or gastrointestinal side effects. Moreover, the tissue explant described herein can be used to screen excipients that alter the gastrointestinal toxicity of drugs. In some embodiments, the excipients include, but are not limited to, those from the GRAS list, inactive ingredients list from FDA, other biocompatible and/or non-toxic small molecular compounds, and polymers as well as nutrients.

In another aspect of the disclosure, a method is provided for screening for agents for their effect on cells of different tissues, including processes of cancer initiation and treatment, and including the use of experimentally modified explants described herein. Tissue explants cultured by the methods described herein are exposed to candidate agents. Agents of interest include pharmaceutical agents, e.g. small molecules, antibodies, peptides, etc., and genetic agents, e.g. antisense, RNAi, expressible coding sequences, and the like, e.g. expressible coding sequences for candidate tumor suppressors, candidate oncogenes, and the like. In some embodiments, the effect on stem cells is determined. In other embodiments the effect of transformation or growth of tumor cells is determined, for example where agents may include, without limitation, chemotherapy, monoclonal antibodies or other protein-based agents, radiation/radiation sensitizers, cDNA, siRNA, shRNA, small molecules, and the like. Agents active on tissue-specific stem cells are detected by change in growth of the tissue explants and by the presence of multilineage differentiation markers indicative of the tissue-specific stem cell. In addition, active agents are detected by analyzing tissue explants for long-term reconstitutive activity. Methods are also provided for using the explant culture to screen for agents that modulate tissue function. In some embodiments, the methods find use in identifying new agents for the treatment of disease. In some embodiments, the methods find use in determining effective delivery of already existing agents.

In some embodiments, the effect of a test compound is determined by conducting a first assay, contacting the tissue explant with a compound of interest, waiting for a sufficient period of time, conducting a second assay on the tissue explant, and comparing the results of the first assay and the second assay, to determine the effect of the compound. Examples of assays include, but are not limited to, drug dissolution, absorption, effect on a tissue (e.g., toxicity, genetic modification, change in protein or gene expression, change in tissue histology/morphology), drug degradation, and hormone secretion. Examples of assays analyzing cytotoxicity include, but are not limited to, Live/Dead assays, alamarBlue®, and RayBio® Bioluminescence Cytotoxicity Assay Kit. In some embodiments, more than one assay is conducted simultaneously.

The agents are added in solution or readily soluble form, to the culture medium. The agents may be added in a flow-through system, as a stream, intermittent, continuous, or alternatively adding a bolus of the compound, singly or incrementally, to an otherwise static solution. In a flow-through system, two fluids are used, where one is a physiologically neutral solution, and the other is the same solution with the compound of interest added. The first fluid is passed over the cells, followed by the second. In a single solution method, a bolus of the test compound is added to the volume of media surrounding the tissue explant. In some embodiments, the compound of interest is injected directly into the tissue explant.

High-Throughput Screening

In some aspects of the disclosure, methods and culture systems are provided for screening candidate agents in a high-throughput format. By "high-throughput" or "HT", it is meant the screening of large numbers of candidate agents or candidate cells simultaneously for an activity of interest. By large numbers, it is meant screening 20 or more candidates at a time, e.g. 40 or more candidates, e.g. 100 or more candidates, 200 or more candidates, 500 or more candidates, or 1000 candidates or more.

In some embodiments, the high throughput screen will be formatted based upon the numbers of wells of the tissue culture plates used, e.g. a 24-well format, in which 24 candidate agents (or less, plus controls) are assayed; a 48-well format, in which 48 candidate agents (or less, plus controls) are assayed; a 96-well format, in which 96 candidate agents (or less, plus controls) are assayed; a 384-well format, in which 384 candidate agents (or less, plus controls) are assayed; a 1536-well format, in which 1536 candidate agents (or less, plus controls) are assayed; or a 3456-well format, in which 3456 candidate agents (or less, plus controls) are assayed.

In some embodiments, the disclosure provides methods for high-throughput screening for analyzing absorption of drug formulations. In some embodiments, the tissue explant is contacted with a substrate, wherein the substrate comprises a plurality of microwells, wherein the tissue explant is contacted with a formulation library comprising a compound of interest and an excipient, wherein absorption of the compound of interest is determined, and wherein results of absorption are compared to identify a formulation for drug absorption.

In some embodiments, the formulation library is a library of GRAS-based excipients that are either known absorption enhancers or have an unknown effect on intestinal absorption.

Compounds of Interest

Compounds of interest are biologically active agents that encompass numerous chemical classes, organic molecules, which may include organometallic molecules, inorganic molecules, genetic sequences, etc. One aspect of the disclosure is to evaluate the absorption of candidate drugs and identify optimum formulations for absorption. Another aspect of the disclosure is to analyze the local effect of an active pharmaceutical ingredient (API) on the tissue. For example, the effect can include, but is not limited to, local tissue toxicity, genetic modification of tissue, temporary change of tissue permeability, drug transporter/metabolizing enzyme inhibition, modulation of mucus or microbiome, and modulation of hormone production and/or secretion. Another aspect of the disclosure is to evaluate the effect of combinations of APIs.

Compounds of interest comprise functional groups necessary for structural interaction with proteins, particularly hydrogen bonding, and typically include at least an amine, carbonyl, hydroxyl or carboxyl group, frequently at least two of the functional chemical groups. The compounds often comprise cyclical carbon or heterocyclic structures and/or aromatic or polyaromatic structures substituted with one or more of the above functional groups. Compounds of interest are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. In some embodiments, compounds of interest include chemotherapeutic agents, anti-inflammatory agents, hormones or hormone antagonists, ion channel modifiers, and neuroactive agents.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. In some embodiments, the library comprises approved and/or experimental drugs. In some embodiments, the library comprises approved and/or experimental drugs conjugated to biologically active or inactive molecules. In some embodiments, a drug library is commercially available.

In some embodiments, candidate agents can also be genetic agents, such as polynucleotides and analogs thereof, which are tested in the screening assays described herein by addition of the genetic agent to the tissue explant. The introduction of the genetic agent can result in an alteration of the total genetic composition of the cells within the tissue explant. Genetic agents such as DNA can result in an experimentally introduced change in the genome of a cell, generally through the integration of the sequence into a chromosome. Genetic changes can also be transient, where the exogenous sequence is not integrated but is maintained as episomal agents. Genetic agents, such as antisense oligonucleotides, can also affect the expression of proteins without changing the cell's genotype, by interfering with the transcription or translation of mRNA. Genetic agents, such as short interfering RNA (siRNA) or short hairpin (shRNA), can effect expression of proteins without changing the cell's genotype by mediated the degradation of the mRNA it binds to. The effect of a genetic agent is to increase or decrease expression of one or more gene products in the cell.

The tissue explant described herein is useful for predicting the absorption, toxicity and/or endocrine stimulation of a variety of agent types. In some embodiments, candidate agents are small molecules (e.g., doxycycline). In some embodiments, candidate agents are small molecule drugs. In some embodiments, candidate agents are biologics, including peptide drugs (e.g., oxytocin) and protein drugs (e.g., insulin). In some embodiments, candidate agents are antisense oligonucleotides.

In some embodiments, candidate agents are known drugs classified by the FDA's Biopharmaceutics Classification System (BCS), which takes into account three major factors that govern the rate and extent of drug absorption from immediate release (IR) solid oral dosage forms: dissolution, solubility and intestinal permeability. BCS Class I refers to high solubility and high permeability, BCS Class II refers to low solubility and high permeability. BCS Class II refers to high solubility and low permeability. BCS Class IV refers to low solubility and low permeability.

E. Modification of Tissue Explant

The tissue explant described herein may be experimentally modified. In some embodiments, the tissue explant is modified prior, or during the culture period. In some embodiments, the tissue explant is modified by exposure to viral or bacterial pathogens. In some embodiments, the tissue explant is modified by altering patterns of gene expression (e.g., by providing reprogramming factors). In some embodiments, the tissue explant is modified through genetic modification. In some embodiments, genetic modification includes, but is not limited to knocking down genes with, for example, interfering RNAs (shRNA, siRNA), and stable genetic modification with, for example, CRISPR/Cas9. The experimentally modified tissue explant is useful for investigation of the effects of drug transporters or drug metabolizing enzymes; the effects of therapeutics agents; for tumor therapy, for effects on differentiation, and the like.

In some embodiments, expression of drug transporters and/or drug metabolizing enzymes is modified. In some embodiments, expression of drug transporters and/or drug metabolizing enzymes is knocked down. In some embodiments, expression of at least one drug transporter is modified. In some embodiments, expression of at least one drug transporter is knocked down. In some embodiments, expression of at least one drug metabolizing enzyme is modified. In some embodiments, expression of at least one drug metabolizing enzyme is knocked down.

In some embodiments, the tissue explant is modified to generate a pathological condition. Examples of pathological conditions include, but are not limited to, inflammatory bowel diseases (IBD), colon cancer, mesenteric ischemia, congenital syndromes and trauma, which can produce functional loss or mandate physical resection of large sections of intestine extensive enough to compromise organ physiology. The ability to maintain tissue explants in culture is valuable for development of therapies for treating intestinal diseases and trauma induced intestinal failure.

Methods for modifying cells or tissue are known to one of skill in the art. For example, introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; siRNA or a shRNA, encode a dominant negative mutation, or dominant or constitutively active mutations of native sequences; altered regulatory sequences, etc. Instead of being expressed from a vector transfected or transduced into the tissue explant, the oligonucleotides, siRNA or shRNA can be directly transfected or transduced into the tissue explant.

In addition to sequences derived from the host cell species, other sequences of interest include, for example, genetic sequences of pathogens, for example coding regions of viral, bacterial and protozoan genes, particularly where the genes affect the function of human or other host cells. Sequences from other species may also be introduced, where there may or may not be a corresponding homologous sequence.

A large number of public resources are available as a source of genetic sequences. e.g. for human, other mammalian, and human pathogen sequences. A substantial portion of the human genome is sequenced, and can be accessed through public databases such as Genbank. Resources include the uni-gene set, as well as genomic sequences. For example, see Dunham et al. (1999) Nature 402, 489-495; or Deloukas et al. (1998) Science 282, 744-746.

cDNA clones corresponding to many human gene sequences are available from the IMAGE consortium. The international IMAGE Consortium laboratories develop and array cDNA clones for worldwide use. The clones are commercially available, for example from Genome Systems, Inc., St. Louis, Mo. Methods for cloning sequences by PCR based on DNA sequence information are also known in the art.

Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express a genetic coding sequence, Expression constructs may contain promoters derived from the genome of mammalian cells, e.g., metallothionein promoter, elongation factor promoter, actin promoter, etc., from mammalian viruses, e.g., the adenovirus late promoter; the vaccinia virus 7.5K promoter, SV40 late promoter, cytomegalovirus, etc.

In mammalian host cells, a number of viral-based expression systems may be utilized, e.g. retrovirus, lentivirus, adenovirus, herpesvirus, and the like. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (see Logan & Shenk, 1984, Proc. Natl. Acad. Sci. USA 81:3655-3659). Specific initiation signals may also be required for efficient translation of inserted gene product coding sequences. These signals include the ATG initiation codon and adjacent sequences. Standard systems for generating adenoviral vectors for expression on inserted sequences are available from commercial sources, for example the Adeno-X™ expression system from Clontech (Clontechniques, January 2000, p. 10-12).

In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

In some embodiments, methods are used that achieve a high efficiency of transfection, and therefore circumvent the need for using selectable markers. These may include physical modes of delivery including microneedles, microjets, iontophoresis, and ultrasound mediated siRNA delivery.

Oxytocin Formulation

In some aspects, the disclosure provides an oral formulation for oxytocin. Oxytocin is currently not available for oral administration due to low intestinal permeability. In some embodiments, polyethyleneimine (800 Da, end-capped; "PEI") formulation increases the intestinal absorption of oxytocin. In some embodiments, oxytocin is formulated using P. In some embodiments, oxytocin formulated with PEI has increased levels of plasma concentration compared to unformulated oxytocin.

As used herein, "oral formulation" refers to the means of a drug delivery system. An oral formulation is intended for swallowing by a subject.

"Effective amount" as applied to oxytocin means the amount of oxytocin generally sufficient to effect a desired change in the subject. "Effective amount" as applied to a non-active ingredient constituent of an oral formulation (e.g., PEI), refers to that amount of the non-active ingredient constituent which is sufficient to positively influence the release of oxytocin at a desired rate for a desired period of time.

In some aspects, the disclosure provides an oxytocin formulation comprising a therapeutically effective amount of oxytocin or functional analogue thereof, and PEI. In some embodiments, the effective concentration of oxytocin is 50 μg/mL. In some embodiments, the effective concentration of oxytocin is about 50 μg/mL. In some embodiments, the concentration of PEI is 1-100 μg. In some embodiments, the concentration of PEI is about 1 to about 100 μg. In some embodiments, the concentration of PEI is 1, 2, 3, 4, 5, 6, 7, 8, 9, 10, 15, 20, 25, 30, 35, 40, 45, 50, 55, 60, 65, 70, 75, 80, 85, 90, 95 or 100 μg.

Kits

In some aspects, the disclosure provides a kit comprising at least a tissue explant described herein. A kit can include a tissue explant described herein, and optionally a substrate, and instructions for use. The kits may comprise, in a suitable container, a tissue explant described herein, and optionally a substrate, and various buffers, reagents, enzymes and other standard ingredients well known in the art. In some embodiments, the kit comprises a tissue explant described herein, a substrate, and one or more formulations. In some embodiments, the formulation is a GRAS (Generally Recognized as Safe)-based excipient. In some embodiments, the kit comprises a library of formulations. In some embodiments, the substrate comprises plates for interfacing with the tissue explant, and cover films to seal one of the plates.

In some embodiments, the kit comprises a tissue explant described herein and a substrate comprising plates for interfacing with the tissue explant and cover films to seal one of the plates, wherein the substrate is compatible with a robotic arm. Such containers may include injection or blow-molded plastic containers into which the desired components are retained. Containers and/or kits can include labeling with instructions for use and/or warnings.

EXAMPLES

Materials and Methods:

Tissue Dissection and Cultivation

Small intestinal tissue was isolated from freshly procured intact gastrointestinal tract from pigs from selected local slaughter houses. After dissecting the tissue longitudinally, it was immersed in a series of saline solutions supplemented with 5% Antibiotic-Antimycotic solution (Cat. nb.15240062, Thermo Fisher Scientific) under sterile conditions. The tissue was then either mounted on the intestinal tissue explant device or kept in cell strainers (Falcon™ Cell Strainers, Mesh size: 100 um, Thermo Fisher Scientific) depending on the experiment and cultured in serum-free cell culture media at 37° C. incubation in an airtight container. For cultivation the following media and supplements were used: Dulbecco's Modified Eagle Medium (DMEM) high glucose (Life Technologies, cat. no. 11965084), DMEM, high glucose, HEPES (Life Technologies, cat. no. 12430054), DMEM, high glucose, no glutamine (Life Technologies, cat. no. 11960044), DMEM, high glucose, pyruvate, no glutamine (Life Technologies, cat. no. 10313021), Advanced DMEM/F-12 (Life Technologies, cat. no. 12634028), MEM Non-Essential Amino Acids Solution (Life Technologies, cat. no. 11140050), EGF Recombinant Human Protein (Life Technologies, cat. no. PHG0311), Fetal Bovine Serum, certified, US origin (Life Technologies, cat. no. 16000044). For biological characterization, intestinal crypt and villi were isolated based on a previously published protocol (Sato, T. & Clevers, H., *Methods Mol. Biol. Vol.* 945: 319-328, 2013).

Reagents

Human oxytocin (synthetic, O3251-5000IU, Sigma), human insulin (recombinant, Cat. no. I2643-25MG, Sigma), teicoplanin (recombinant, Cat. no. T0578, Sigma), Carbetocin acetate (synthetic, SML0748, Sigma) were labeled using A-20000 Alexa Fluor®488 NHS Ester (Succinimidyl Ester) labeling kit prior to usage. Label IT® RNAi Delivery Control Cy®3 was purchased from Mirus Bio. Additionally, the following model drugs were all purchased from Sigma:

Antipyrine, Beta Carotene, Danazol, Verapamil, Ivermectin, Metropolol, Naproxen, Oseltamivir phosphate, Memantine, Entecavir monohydrate, Emtricitabine, Ergotamine D-tartrate, Labetalol, Ketoprofen, Desipramine, Moxifloxacin, Carbamazepine, Atorvastatin, Domperidone, Piroxicam, Ibuprofen, Theophylline, Propranolol, Mesalamine, Caffeine, Phenytoin, Valacyclovir, Coumarin, Doxycycline, Metformin, Fluvastatin, Terbutaline, Warfarin, Indomethacin, Acyclovir, Chlorpheniramine, Saquinavir, Rosuvastatin, Quinine, Quinidine, Furosemide, Ranitidine, Chlortetracycline, Dihydroergotamine-tartrate salt, Amiloride, Omeprazole, Atenolol, Famotidine, Curcumin, FITC Dextran 4 kDa, FITC Dextran 20 kDa, FITC Dextran 70 kDa, and Fluorescein. The following chemicals that were tested as formulation excipients were all purchased from Sigma: δ-decalactone, 2-Phospho-L-Ascrobic Acid Trisodium Salt, 4 Arm PEG, 8 arm PEG, 4-(dimethylamino)pyridine, 6-O-Palmitoyl-L-ascorbic acid, Acesulfame K, Adipic Acid, Agar, Agarose, Albumin (Bovine Serum), Alginic Acid Sodium Salt (Brown Algae), Alginic Acid Sodium Salt (Kelp), Alpha cyclodextrin, Bacitracin, B-Alanine, B-Cyclodextrin, BD PuraMatrix Peptide Hydrogel, Bentonite, Caffeine, Carbopol 934, Carboxymethylcellulose, Carnuba Wax No. 1 yellow, Castor Oil, Cellulose acetate, Cellulose Acetate Phalate, Cellulose acetate propionate, Chitin (from shrimp shells), Chitosan, Chitosan, medium molecular weight, Cholesterol, Citric Acid, Corn Oil, Cottonseed Oil, Cysteamine, D (+)-Mannose, D(−) Fructose, D(+) Glucose, D(+) Trehalose Dihydrate, Dextran, Dextrose, D-Lacititol, D-Leucine, DL-Tartaric Acid, D-Mannitol, D-Methionine, D-Tryptophan, Dynasan 118 Microfine, Edetate Dissodium, Ethylenedinitrilol-tetracetic acid disodium salt, L(+) Arabinose, Laponite, L-Arginine, L-Ascorbic Acid, L-Cysteine Hydrochloride Monohydrate, Lecithin, L-Histidine, Locust bean gum from *Ceratonia siliqua* seeds, L-Phenylaline, L-Proline, L-Threonine, Meglomine, Miglyol 812, Mineral Oil, Mowiol 10-98, Mowiol 18-88, Mowiol 4-98, Mowiol 56-98, Mowiol 8-88, Mucin (Porcine Stomach), Neocuproine, Parrafin Wax, Peanut Oil, PEG-block-PEG-Block-PEG, Pepsin from porcine gastric mucosa, Pluronic F-127, Pluronic F-68, Pluronic P85, Poly (dimethylsiloxane), bis(3-aminopropyl) terminated, Poly (DL-lactide-co-glycolide), Poly (L-lactide co-caprolactone co-glycolide), Poly (propylene glycol) Diglycidyl Ether, Poly(dimethylsiloxane)-graft polyacrylates, Poly(ethylene glycol) bis (amine), Poly(ethylene-co-glycidyl methacrylate), Poly(ethylene-co-vinyl-acetate), Poly(Lactide-co-Glycolide) acid (PLGA), Poly(methyl methacrylate-co-methacrylic acid), Poly(propylene glycol) diglycidyl ether, Poly(tert-butyl acrylate-co-ethyl acrylate-co-methacrylic acid), Poly(vinyl acetate), Poly(vinyl alcohol), Poly(vinyl alcohol), Poly[dimethylsiloxane-co-[3-[2-(2-hydroxyethoxy)ethoxy]-propyl]methylsiloxane], Poly [dimethylsiloxane-co-methyl (3-hydroxypropyl) siloxane] graft-poly(ethylenegylcol) methyl ether, Polyacrylic acid, Polyacrylic acid, Polyaniline, Polycaprolactone (PCL), Polycaprolactone, Polycaprolactone Triol, Polyethylene Glycol 3350 Da, Polyethylene Glycol 400 Da, Polyethylene Glycol methylether, Polyethylene Gylcol 10 kDa, Polyethylene Gylcol 35 kDa, Polyethylene Gylcol 500 kDa, Polyethylene Gylcol 800 Da, Polyethyleneimine, Polyoxyethylene (20 kDa), Sorbitan Monooleate (Tween 80), Polysorbate 80, Polystrene Beads (200 nm), Polystrene Thiol Terminated, Polyvinyl Chloride-vinyl acetate, Polyvinylpyrrolidone, Polyvinylpyrrolidone K90, Propyl Gallate, Riboflavin, Riboflavin 5'-monophosphate sodium salt, SDS, Sebacic Acid, Sesame Oil, Sigma 7-9 (Tris base), Silica gel, Sodium Glycholate, Sodium Glycochenodeoxycholate, Sodium glycocholate hydrate, Sodium Hyaluronate, Sodium taurocholate hydrate, Soluplus, Soybean Oil, Span 80, Starch, soluble Sucrose, Sucrose Ultra (Fluka), Synperonic F108, Talc, Tauchloric Acid, Taurochenodeoxycholate, Taurodeoxycholate, Tetraglycol, Thioflavin T, Tragacanth, Triacetin, Tristearin, TritonX100, Tween 28-LQ-(AP), Tween20, Uridine, Vanillin, Vegetable Oil, Vitamin B12, Xantham gum from *Xanthomonas Campestris*, Xylitol, y-decalactone, Zonyl FSO-100 fluorosurfactant, α-Tocopherol, ε-caprolactam, ε-caprolactone, ω-pentadecalactone, Gelatin, Gelatin from bovine skin, Type B, Gelatin from cold water fish skin, Gelatin from porcine skin, type A, Glycerin, Glycine, Glycocholic Acid, Guar, Heparin sodium salt from porcine intestinal mucosa, Hydroxyapatide Nanoparticles (200 nm), Hydroxypropylmethylcellulose phalate, Influenza Hemagglutinin (HA) Peptide, Iron (III) Oxide, Koliphor® EL, Kollicoat® SR 30D, Kollidon® 25, Kollidon® VA 64, Kollidon® 12PF, Kollidon® P188, Kollidon® SR, Kollidon® V67, Kollidon® P407, Kollidon® RH40, EUDRAGIT® E PO, EUDRAGIT® E100, EUDRAGIT® NM 30D, EUDRAGIT® RL PO, EUDRAGIT® S100, EUDRAGIT® L 100-55, EUDRAGIT® RS PO. For immunolabelling, the following primary antibodies were used in 1:200 dilutions: CDX2 (Rabbit, Cell Signaling), E-Cadherin (Mouse, Cell Signaling), Claudin-1 Rabbit Cell Signaling, Vimentin (Rabbit, Cell Signaling), FABP1 (Rabbit, Cell Signaling), GLP-1 (Goat, Santa Cruz), Lgr5/GPR49 (Rabbit, Thermo Fisher), Wnt3a (Rabbit, Abcam), Villin (Rabbit, Thermo Fisher), MUC2 (Rabbit, Thermo Fisher), Nestin (Rabbit Thermo Fisher), MDR-1 (Rabbit, Novus), CYP3A4 (Rabbit, Cell Signaling), R-spondinl (Mouse, R&D Systems), Chromogranin A (Mouse, Abcam), Lysozyme (Rabbit, Abcam), HLA DR+HLA DP (Mouse, Abcam), OLFM4 (Rabbit, Abcam), Keratin 20 (Rabbit, Cell Signaling), GFAP (Chicken, Abcam). Additionally, Wheat Germ Agglutinin, Alexa Fluor®594 Conjugate, L12492, LysoTracker® Deep Red and R37112 ActinRed™ 555 ReadyProbes® Reagent DAPI (4',6-Diamidino-2-Phenylindole, Dihydrochloride) were all purchased from Life Technologies.

Pharmacokinetic Analysis in Porcine Model

All animal procedures were conducted in accordance with protocols approved by the Massachusetts Institute of Technology Committee on Animal Care. For tissue experiments, fresh tissue was obtained from local abattoirs within 20 minutes of euthanization.

Scanning Electron Microscopy (SEM) Analysis

Tissue explants were fixed in 4% (v/w) formalin in PBS for 2 days at 4° C. After that, samples were washed five times with deionized water and then dehydrated through a graded ethanol (Sigma, ACS reagent 99.5%) series two times for each concentration (20, 30, 40, 50 70, 80, 90, 100, 100, 100% (v/v)) for 2 minutes in each solution. After dehydration, the samples were immersed in a Hexamethyldisilazane (Sigma) solution overnight. Due to the volatile nature of hexamethyldisilazane, the solution evaporates overnight resulting in dry tissue pieces. The morphology of the fabricated surfaces was observed using a JEOL 5600LV SEM. Before visualization under SEM, all samples were sputter-coated with carbon using the Hummer 6.2 Sputter Coating System. Samples were cut to be under 0.5 $cm^2$ in area and fixed to the aluminum stubs by a double-sided adhesive carbon conductive tape.

Immunohistochemical Staining

Isolated villi and crypts were fixed with 4% (v/w) formalin in PBS for 30 minutes at room temperature, washed with PBS, permeabilised with 0.25% (v/v) Triton-X-100/PBS for 2 minutes, washed with PBS and then blocked with 4%

(w/v) bovine serum albumin in PBS for 1 hour. Primary and secondary antibodies were incubated in blocking buffer for 2 hours at room temperature or at 4° C. overnight. The stained cells were then mounted on a cover slide using ProLong® Diamond Antifade Mountant (Thermo Fisher Scientific).

Tissue explants were fixed in 4% (v/w) formalin in PBS for 2 days at 4 C. Then dehydration and paraffin embedding was performed followed by tissue sectioning. For the resulting paraffin embedded tissue slides dewaxing and antigen retrieval was conducted according to standard protocols followed by staining procedure.

Cryo-sections of tissue explants were generated by snap freezing tissue in liquid nitrogen embedded in an optimum cutting temperature (O.C.T.) formulation (Tissue-Tek® O.C.T. Compound, Sakura® Finetek). Tissue sections were generated by using a Cryostat. The resulting tissue slides were fixed with 4% (v/w) formalin in PBS for 30 minutes at room temperature, washed with PBS, washed with PBS and then blocked with 4% (w/v) bovine serum albumin in PBS for 1 hour followed by using tissue dyes according to manufacturer protocols.

Microscopy Analysis

Light microscopy analysis of histology slides was conducted using an EVOS FL Cell Imaging System with 10× or 20× air objectives. Fluorescent samples were analyzed using a Nikon AiR Ultra-Fast Spectral Scanning Confocal Microscope in a Galvano scanner using a 20× air or 60× oil immersion objective. Resulting raw images were analyzed with NIS-Elements C software and ImageJ.

Intestinal Tissue Explant Perfusion Experiments

To assemble the intestinal tissue explant system, freshly isolated intestinal tissue from the jejunum was prepared according to the described tissue dissection procedure and mounted on the manufactured interface design with a generic 96 well plate as a receiver plate (Corning® 96 well plates, clear bottom, Corning) or a UV transparent plate (Corning® 96-well UV Plates, Corning). The jejunum was identified as the region of the small intestine approximately 50 cm after the pylorus. The difference between the jejunum and ileum was determined based on anatomical location, the structural differences of the tissue, differences in blood supply, and fat deposition as well as the presence of lymphoid tissue. For the system in 384-well format, a 384 microplate with glass bottom (Greiner Sensoplate™ glass bottom multiwall plates, Sigma) were used. The tissue was then cultured in this system according to the described cultivation protocol for specific ex vivo cultivation time periods. Intestinal perfusion experiments using the system were conducted only once after 24 hours of ex vivo cultivation unless otherwise noted.

For perfusion experiments the following set up was used: Formulation samples were prepared using a liquid handling station (Evo 150 liquid handling deck, Tecan), an automated dispenser (EL406 Combination Washer Dispenser, BioTek Instruments) was used to fill receiver 96 well plates, a microplate reader (Infinite® M1000 PRO, Tecan) was then used for spectrophotometric analysis. Specifically, formulation samples were prepared following a protocol to mix the pre-pared excipient plate 10 times, pipette the appropriate amount of excipient and dispense into a 96-well plate with the appropriate amount of compound already it in. The excipient/compound formulations were then mixed 60 times and then the appropriate amount was pipetted and dispensed onto the tissue explant. All experiments, including sample incubation, were performed at room temperature.

The apparent Permeability ($P_{app}$) values were calculated using the following equation:

$$P_{app} = \frac{V}{A * C_0} * \frac{\Delta C_R}{\Delta t}$$

where V is the volume in the receive chamber, A is the tissue surface area, $C_0$ is the initial concentration in the donor chamber, and $\Delta C_R$ is the concentration increase in the receive chamber in the incubation time $\Delta t$.

Statistical Analysis

Correlation of human absorption compared to $P_{app}$ of tissue explants or $P_{app}$ of Caco-2 was performed by a two-tailed non-parametric Spearman correlation function. Oxytocin pharmacokinetic in vivo data was analyzed by one-way ANOVA followed by a Tukey and Bonferroni post hoc analysis. For formulation screening analysis, the two components in excipient mixes were treated as either features or individuals and clustered independently using ascendant hierarchical clustering based on Euclidian distances, optionally preceded by the k-means algorithm depending on the matrix's size. The data matrix's rows and columns were then permuted according to corresponding clusterings to bring similar columns closer to each other and similar lines closer to each other. This data was then displayed in a color coded heat map reflecting data in the permuted matrix.

Example 1: Ex Vivo Cultivation System for Intestinal Tissue

Figure 1B:
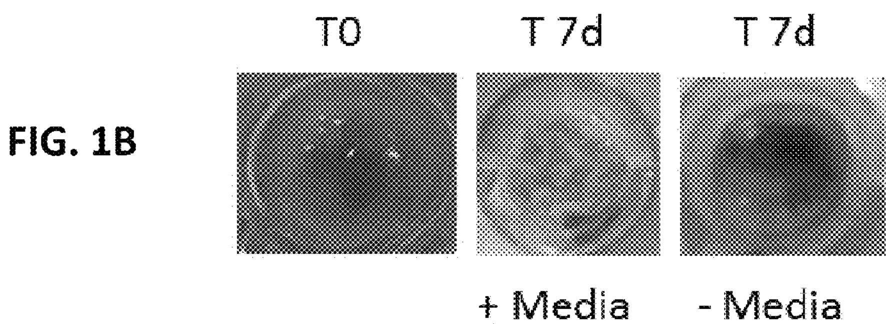
FIG. 1B provides images of the luminal side of small intestinal tissue explants with media or without media cultivation 7 days ex vivo.
Figure 1C:
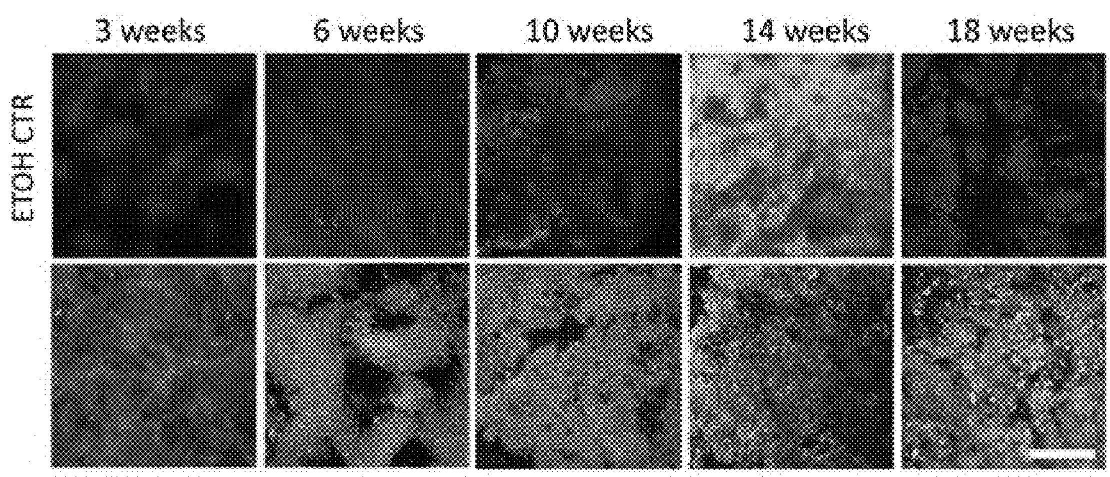
FIG. 1C provides images of LiveDead analysis of small intestinal tissue explants cultured with (top) or without (bottom) an intact stroma layer. Scale bar=200 µm.
Figure 1C:
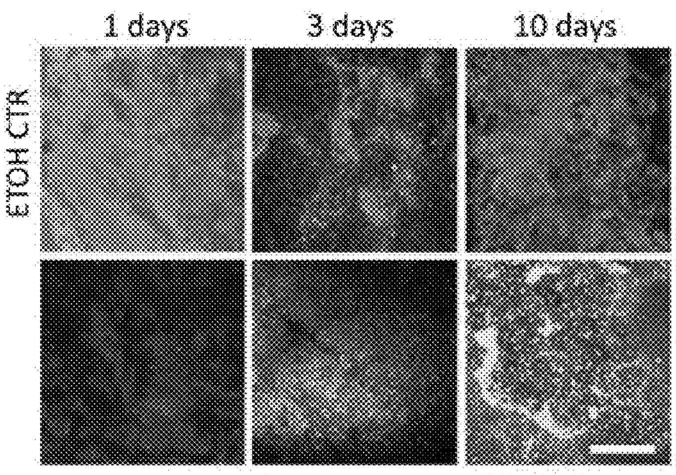
Figure 1D:
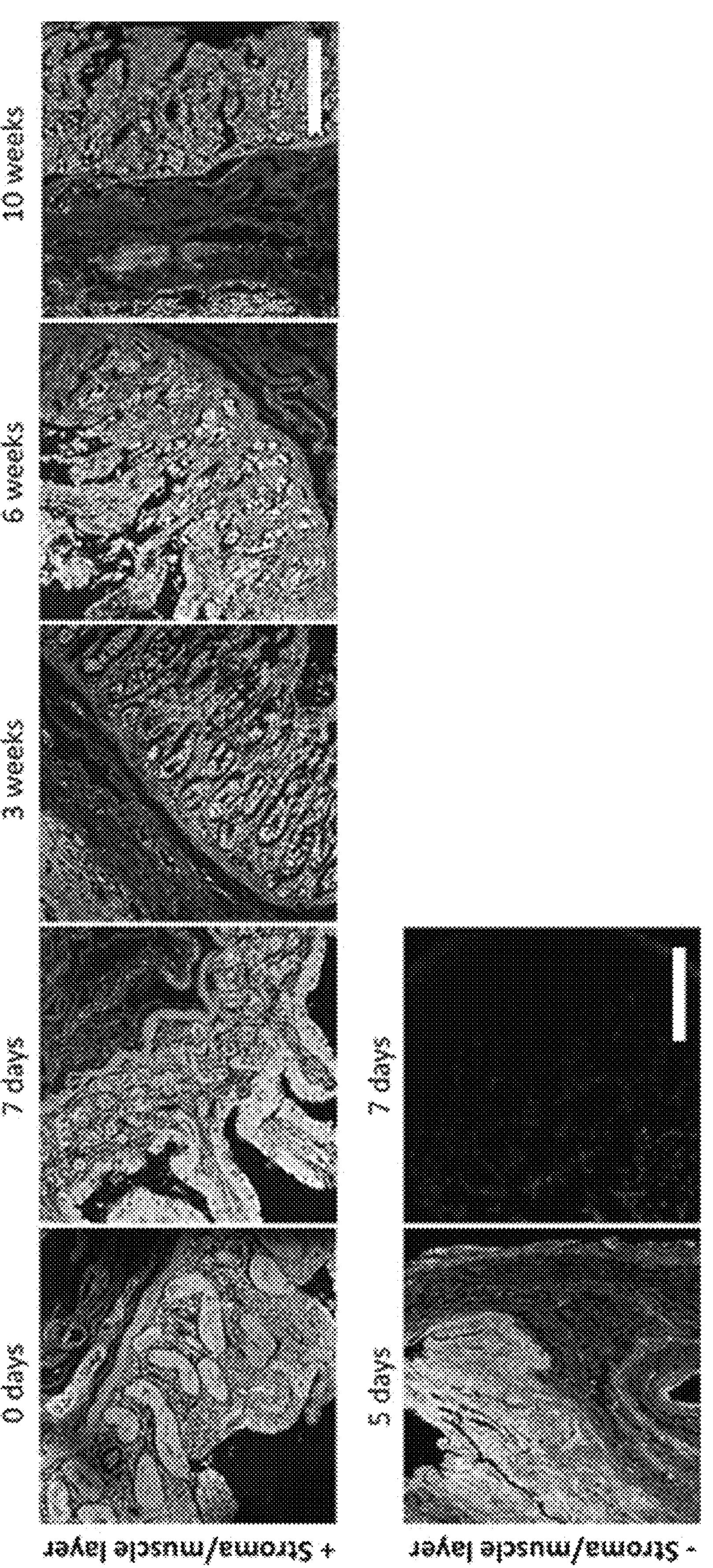
FIG. 1D provides images of confocal analysis of sections of small intestinal tissue explants cultured for 0 days (fresh tissue), 7 days, 3 weeks, 6 weeks, 10 weeks with stroma layer (top) or for 5 or 7 days with stroma layer removed (bottom). Sections were stained with Dapi (cell nucleus), Phalloidin (F-actin and plasma membrane), and LysoTracker (lysozyme). Scale bar=200 µm.

To determine whether intestinal tissue could be cultivated in a manner that maintained viability and in vivo architecture, small intestinal tissue was isolated from freshly procured intact gastrointestinal tract from pigs. The viability of intestinal tissue explants was found to be dependent on specific media compositions (FIG. 1A). No difference in viability was observed between tissue cultured in DMEM F12 alone and DMEM F12 with FBS or EGF added. In addition, FIG. 1B shows pictures of the luminal side of the small intestinal tissue explants with or without media cultivation after 7 days, indicating the explants survived best with media. The stroma was found to be essential in maintaining the cell survival of the intestinal epithelium in ex vivo cultivation (FIG. 1C). Confocal analysis of sectioned intestinal tissue explants that were stained with Dapi (blue, cell nucleus), Phalloidin (green, F-actin, Wheat Germ Agglutinin (Plasma membrane, red) and LysoTracker® (lysozyme, purple), showed intact cells for up to 10 weeks while the tissue morphology appeared to change after 2-3 weeks (FIG. 1D). Moreover, when the stromal layer was removed prior to ex vivo explant cultivation, no intact cells were detected after 5 days under identical cultivation conditions (FIG. 1D).

Figures 1E, 1F:
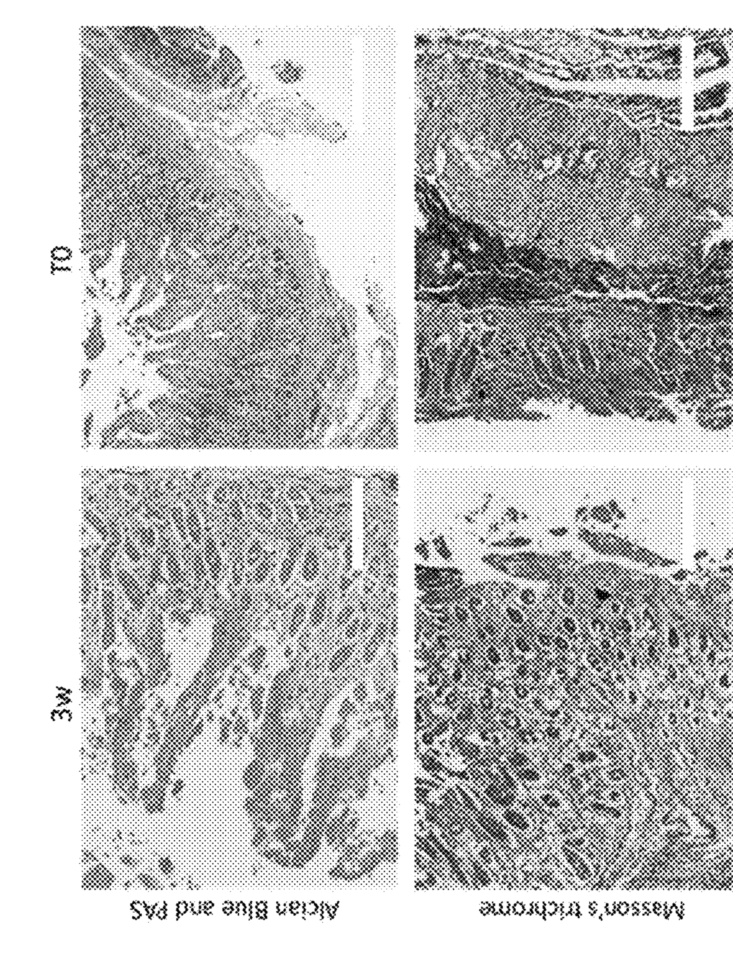
FIG. 1E provides images of scanning electron microscopy (SEM) of intestinal tissue explants cultured for either 0 days (fresh tissue), 2 days, 7 days, 3 weeks or 4 weeks ex vivo. Scale bar=200 µm.
FIG. 1F provides images of light microscopy analysis of sections of small intestinal tissue explants cultured for 3 weeks ex vivo (left) or freshly isolated (right; "TO") followed by Periodic acid-Schiff (PAS)/Alcian blue stain (top) or Masson's trichrome (bottom). Scale bar=200 µm.

In addition, the villi-crypt topography of intestinal tissue explants cultured ex vivo was analyzed by scanning electron microscopy (SEM) to determine whether villi structures remained intact. FIG. 1E shows the villi structures were indeed intact.

Figure 1G:
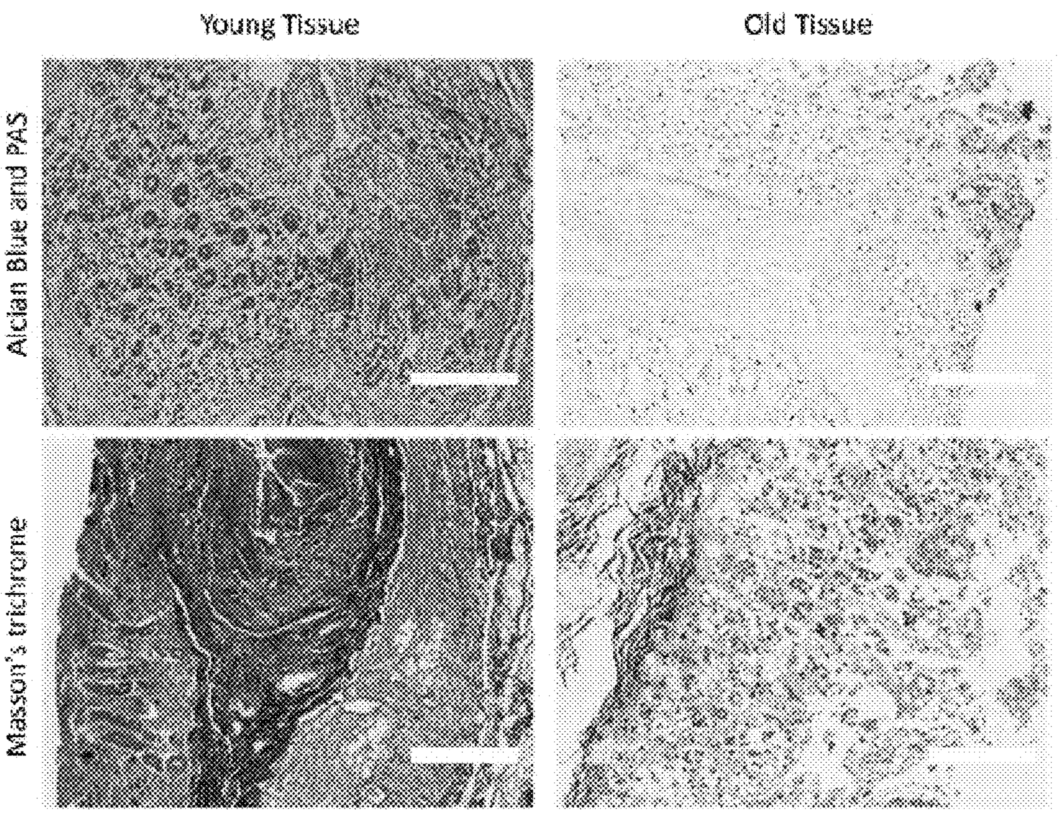
FIG. 1G provides images of light microscopy analysis of sections of small intestinal tissue explants isolated from young (~3 weeks old; left) or old (~3 months old; right) animals, cultured for 3 weeks ex vivo and stained by Periodic acid-Schiff (PAS)/Alcian blue stain (top) or Masson's trichrome (bottom). Scale bar=200 µm.

Histological analysis of tissue cultured for 3 weeks or longer revealed a change in the tissue architecture compared to fresh tissue. These changes likely included degradation of the extracellular matrix and a change in the cell populations of the intestinal epithelium, as shown in FIG. 1F. In addition, histological analysis of tissue cultured from younger (~3 weeks old) or older (~3 months hold) animals was performed. FIG. 1G shows more intact tissue architecture in tissue isolated from younger animals.

To investigate changes in the intestinal epithelium induced by ex vivo cultivation, the expression level of a broad range of cell type markers and drug transporters in fresh tissue and tissue cultured for 7 days ex vivo was investigated.

Gene expression was analyzed via rtPCR. The protein level of cell markers where antibodies were available was investigated by Western Blot analysis. Specifically, tissue was cut in pieces around 30 mg, snapped frozen in liquid nitrogen immediately afterwards and stored at −80° C. For tissue lysis, frozen tissue was washed with 1 volume of chilled PBS, followed by 2 volumes of freshly prepared RIPA Lysis and Extraction Buffer (Cell Signal) with protease inhibitors (Halt™ Protease Inhibitor Cocktail, ThermoFisher). Tissue was lysed with a hand motor for 3-5 cycles of 30 seconds mixing followed by 30 seconds of cooling on ice until tissue is completely homogenized. The lysate was centrifuged at 1200 rpm for 30 minutes at 4° C. and the resulting supernatant transferred into a new vial. The total protein concentration of the lysate was then analyzed by a BCA assay (Pierce™ BCA Protein Assay Kit, ThermoFisher) according to the manufacturer protocol. For SDS-PAGE, each set of tissue protein (~500 μg in RIPA buffer with protease inhibitor, pH 7.5) was mixed in concentrated (2×) Laemmli sample buffer (Bio-Rad) that contained β-mercaptoethanol. The samples were heated for 95° C. for 5 minutes and then run in 12% polyacrylamide gel containing 3.5 mM SDS at 120 volts for 90-120 minutes in SDS-Tris-Glycine buffer, pH 8.0. Proteins were transferred onto methanol activated PVDF membrane under 200 milliamps for 1-3 hours. After 5% BSA blocking, the membrane was incubated with primary antibody (1:200 as the working concentration) at 4° C. overnight, followed by incubation with anti-mouse (1:3000, Abcam) or anti-rabbit (1:2000, Abcam) secondary antibody at room temperature for 3 hours. The target protein was detected with a Bio-Rad imager according to manufacturer protocol.

Figures 1H, 1I:
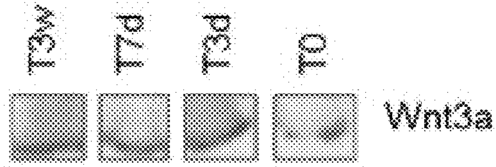
FIG. 1H provides representative images showing protein expression as analyzed by Western Blot analysis (left) and gene expression as analyzed by rtPCR (right) of small intestinal tissue explants cultured for 0 days (fresh) or 7 days ex vivo.
FIG. 1I provides representative images for Western Blot analysis for Wnt3a of protein lysates from small intestinal tissue explants cultured for 0 (fresh), 3, or 7 days, or 3 weeks ex vivo.
Figure 1J:
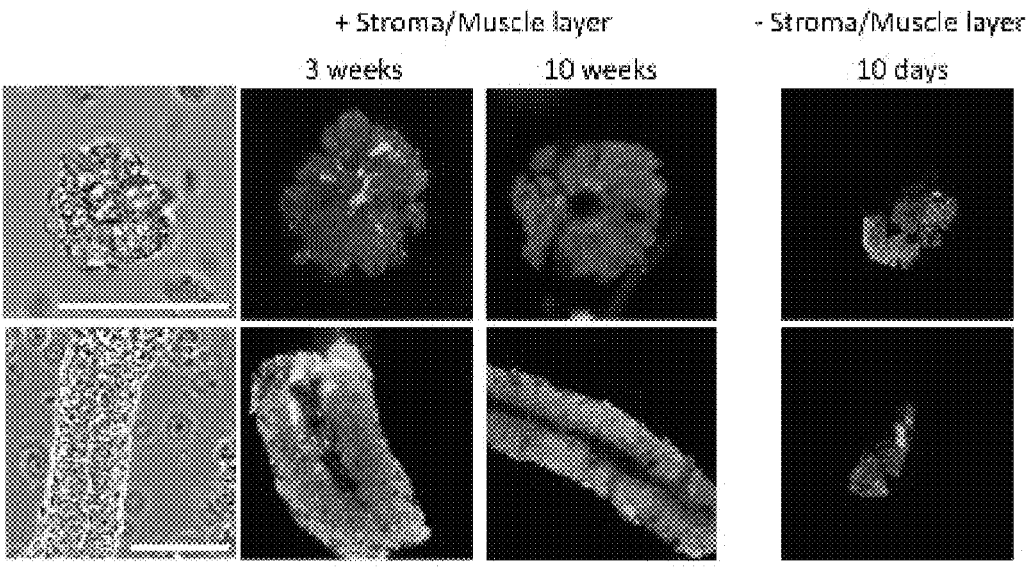
FIG. 1J provides images of confocal microscopy analysis of intestinal villi and crypts isolated from fresh intestinal tissue or intestinal tissue explants cultured for 3 or 10 weeks with stroma layer intact or 10 days without stroma layer. Scale bar=500 µm.

Similar gene and protein expression of the ex vivo culture compared to freshly harvested tissue was observed for all the markers analyzed (FIG. 1H). The presence of caudal type homeobox 2 (CDX-2), Keratin 20 (KRT20) as well as Fatty Acid Binding Protein 1 (FABP-1) as well as cell-cell adhesion markers of the intestinal epithelium (ZO-2 and E-Cadherin as well as various Claudins) demonstrates the intactness of the differentiated intestinal epithelium. The presence of Leucine-rich repeat-containing G-protein coupled receptor 5 (LGFR5) and Olfactomedin 4 (OLFM4) indicated intestinal stem cells were in the tissue explant. The presence of Claudin-1 and Glucagon-like peptide-1 (GLP-1) indicated endocrine cells were in the tissue explant. The presence of Vimentin indicated microfold cells (M cells) were in the tissue explant. The presence of mucin 2 (MUC-2) indicated goblet cells were in the tissue explant. The presence of lysozyme 1 indicated Paneth cells were in the tissue explant. The presence of nestin and synaptophysin (SYP) indicated neuronal cells were in the tissue explant. Importantly, no clear change in the protein concentration of various intestinal drug transporters was observed (i.e., ABC drug efflux transporter MDR-1, canalicular multispecific organic anion transporter 2 (ABCC3), multidrug resistance-associated protein2 (MRP-2), peptide transporter 1 (PEPT-1), breast cancer resistance protein (BCRP), organic cation transporter 1 (OCT-1), organic solute transporter subunit alpha (OST-α) and monocarboxylate transporter (MCT-1)). Interestingly, ex vivo cultured tissue maintained a constant level of secreted Wnt3a and R-Spondin-1 according to Western Blot analysis (FIGS. 1H and 1I), with Wnt3a showing secretion of up to 3 weeks (FIG. 1I). Wnt3a and R-Spondin-1 are a soluble ligands of the canonical Wnt/β-Catenin pathway and reported to play an important role in the maintenance of intestinal stem cell function and viability. Furthermore, intact villi and crypts were isolated from the intestinal epithelium after long term ex vivo culture but only if the stroma layer was not removed (FIG. 1J).

Moreover, sectioned intestinal tissue explants were analyzed by immunohistochemistry (data not shown). The vimentin-mesenchymal cells in the lamina propria were observed by vimentin staining in both the freshly isolated and 7 days ex vivo cultured tissue. Similar results were found in CDX-2 staining, with a characteristic accumulation of CDX-2 signal in the nucleus of differentiated intestinal epithelium. Other mature intestinal epithelium markers (FABP-1 and KRT20) were found to be specific to the intestinal epithelium but showed various signal intensities between freshly excised and ex vivo cultured tissue. Importantly, E-cadherin staining revealed intact cell-cell adhesions in tissue explants after 7 days ex vivo culture with no visible difference compared to freshly isolated tissue. Wnt3a was also found to be present in the intestinal crypts, and a similar amount of goblet cells was observed in ex vivo cultured tissue compared to fresh tissue.

Figure 1K:
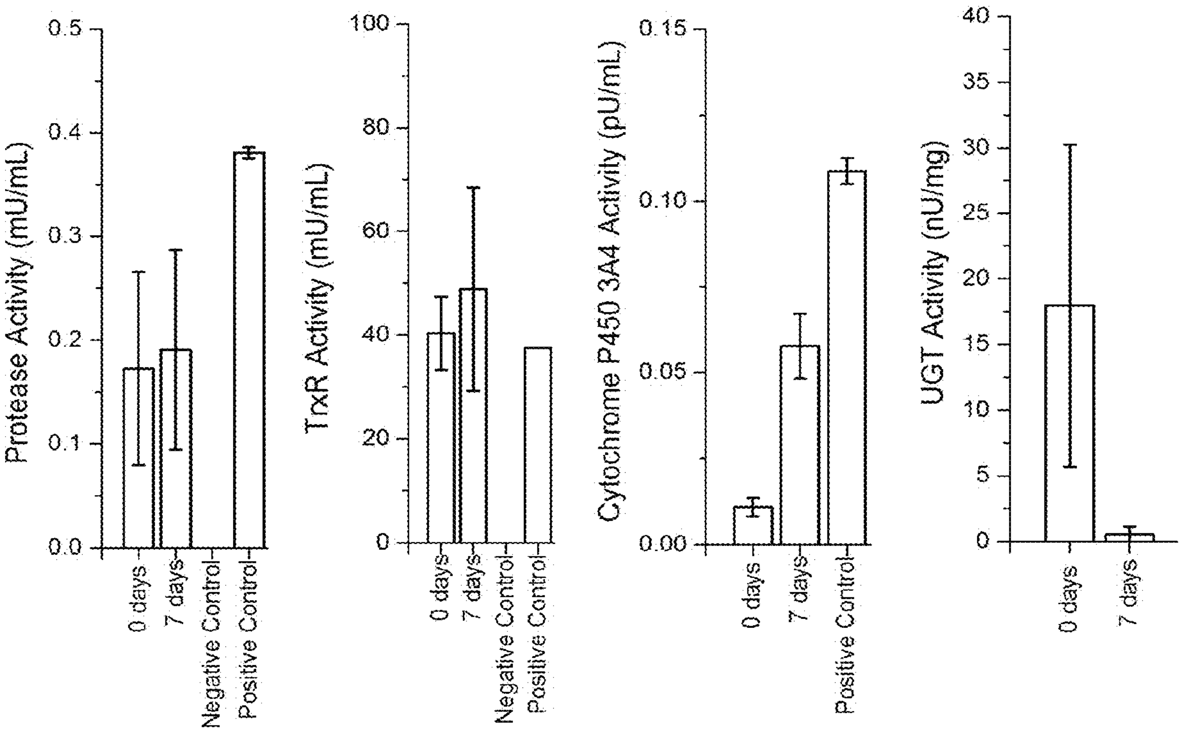
FIG. 1K provides bar graphs showing protease activity (left), thioreductase activity (second to left), cytochrome P450 activity (second to right) and UGT activity (right) of small intestinal tissue explants cultured for 0 days (fresh) or 7 days ex vivo. Results represent 3 independent experiments (n=3). Error bars show standard deviation.

Bioactivity analysis of thioredoxin reductase activity, which is a ubiquitous enzyme involved in many cellular processes such as cell growth, and protection against oxidation stress, was measured using the Thioredoxin Reductase Activity Assay Kit (Cat. no. 68AT-ThioRed-S100, Ray Biotech). As shown in FIG. 1K, there were no significant differences between fresh tissue lysates or tissue cultured ex vivo for up to 7 days. Protease activity was also investigated using a Protease Activity Assay Kit (Cat. no. 68AT-Protease-S100, RayBiotech). No significant change between fresh tissue and tissue cultured ex vivo for 7 days was observed (FIG. 1K). Furthermore, the activity of the metabolizing enzymes chytochrome P450 3A4 (CYP3A4) and uridine 5'-diphospho glucuronosyltransferase (UGT) was confirmed (FIG. 1K). Interestingly, the activity appeared to fluctuate between freshly excised tissue and tissue explants cultured for 7 days ex vivo.

These results indicated intestinal tissue explants could be maintained ex vivo long term and retained the tissue architecture and specific cell types within the epithelium and mucosa for approximately 2-3 weeks. Moreover, the ex vivo viability of the intestinal tissue explant was found to be dependent on having the underlying stroma intact, cultivation conditions and optimal medium composition.

Example 2: Intestinal Tissue Explant Platform Development

Next, the use of the intestinal tissue explant from Example 1 in a high-throughput platform was investigated. An interface platform for intestinal tissue explant cultivation that enabled high-throughput intestinal drug perfusion measurements combined with long-term tissue cultivation capability was designed. Specifically, a broad range of different designs and materials for potential interfacing systems was systematically assessed. As shown in FIG. 2A, a system that enables low sample variability, tissue viability maintenance, rapid assembly and compatibility with robotic handling was developed. The design consisted of an upper device that compartmentalized the intestinal tissue in a 96 multi-well plate format. The tissue formed the bottom of the multi-well plate and was sealed off around each of the 96 wells by using an additional device underneath the tissue. The system was enclosed by a case that enabled adjustable pressure to maintain the system in position for robotic handling.

More specifically, the interface apparatus consisted of a standard 96 well plate, a thin middle plate, and an upper load plate. The intestinal tissue was placed over the through holes in the middle plate. The upper load plate was placed onto the tissue, which compressed the tissue onto the middle plate and around the through holes. Based on the pressure maintained by the upper plate, a seal was created. Several methods of fabrication were used in the prototyping phases. Equipment used included a 3D printer (Stratasys Objet30 Pro), water jet (OMAX MicroMax), and laser cutter (Universal VLS6.60). For the upper load plate, varying diameter posts from 3 mm to 5 mm were printed for the 96 well format using a 3D printer. Supplementary weights were added during testing to compensate for the 3D printer polymer's light weight. The final devices were manufactured using aluminum alloy with 4 mm posts. The aluminum plate was provided by Proto Labs Inc., through direct metal laser sintering (DMLS). The tissue placed on the middle plate was slightly recessed into each well by forces from the upper plate. The thickness, rigidity, and diameter of the through holes of the middle plate were explored to optimize this condition. Several materials were used including aluminum and acrylic because of their rigidity and machinability. The aluminum plates were water jet cut whereas the acrylic sheets were laser cut. Plate thicknesses between 1 mm and 2 mm were explored and 1 mm was chosen. The diameter of the middle plate was designed to be larger than the diameter of the upper load plate so the tissue could rest in between the upper and middle plate. Several diameters ranging from 6.5 mm to 8 mm were explored and the 6 mm diameter was chosen.

Development of the interface between upper and lower segments of the device included identification of optimal geometries of the upper segment and pressure on the tissue to minimize well-to-well leakage. FIG. 2B shows the 6 mm diameter resulted in the least leakage. To understand the effect pressure had on the area of interaction with the drug, fine element analysis of the device revealed a non-uniform strain distribution in the tissue. The finite element package COMSOL Multiphysics/Structural (COMSOL 5.2, Stockholm, Sweden) was used. Due to the symmetry of the system, a single well system with periodic boundary conditions on the tissue was modeled. The tissue behavior was captured using an isotropic near incompressible hyperelastic (neo-Hookean) model with shear modulus of $\mu$=3160 Pa, and $\kappa/\mu$=50, where $\kappa$ is the bulk modulus of the tissue. Since the plates were much stiffer than the tissue, bother upper and lower plates were considered as rigid. The tissue was modeled by a refined mesh of linear hexagonal elements. The contact between the tissue and the plates was modeled using a penalty technique. The results indicated that the tissue area located within each well was clearly less mechanically affected compared to the tissue surrounding the well plates (see FIG. 2C).

Moreover, a magnet based interface system was designed to seal wells by magnetic compression. The weight, dimension and shape of the plates were specifically designed to fully interface with a robotic screening platform, as described herein. Perfusion analysis of FITC with or without dextran (4 kDa) using this interface was measured over time. In addition, FITC perfusion variability over multiple experiments, along with well-to-well leakage of FITC over 6 hours, as function of different magnet strength used, was analyzed. FIG. 2D shows the magnet based interface system provided reproducibility and is suitable for the methods described herein.

Next, the signal variability between intestinal tissue with or without the outer muscle and serosa was investigated through analysis of the perfusion of fluorescein (FITC). After adding the drug, the concentration difference between the upper and lower plate was measured to calculate the rate of perfusion of the drug through the intestinal tissue over 1-2 hours. Signal variability was reduced when the outer muscle and serosa were removed during the tissue isolation procedure (FIG. 2E). The relative standard deviation (a) shows the variability across 480 samples analyzed was reduced upon removal of the outer muscle and serosa.

The perfusion and experimental variability was also investigated. First, the perfusion of FITC with or without various molecular weights of Dextran through the intestinal tissue under a range of pressure was analyzed. As shown in FIG. 2F, the sample variability as measured by the relative standard deviation is lowest with a force of 5N applied across the whole tissue plate. Next, perfusion experiments were conducted with model compounds (FITC, Dextran, Oxytocin and Insulin) across a range of molecular weight and with intestinal tissue from different animals, different regions within the jejunum of the small intestine, as well as different incubation times. 500 individual measurements from 6 different animal batches in one data set resulted in a relative standard deviation (a) of around 20% for all the different model drugs (FIG. 2G). Perfusion of siRNA was also investigated and resulted in a relative standard deviation of around 25% (data not shown). Unexpectedly, reuse of the tissue multiple times for perfusion experiments over the time course of 7 days did not affect the perfusion results (FIG. 2H). Finally, perfusion time lapse analysis of FITC with or without Dextran was conducted. FIG. 2I shows 96 individual time lapses over 2 hours, indicating dynamic measurements can be made by serial sampling.

Furthermore, other tissues from the gastrointestinal tract, including stomach, duodenum and colon were tested in the system. FIG. 2J shows H&E staining of sections of these tissues, whereas FIG. 2K shows LiveDead analysis of these tissues cultured 1 week and 3 weeks ex vivo. These results indicated tissue from the stomach, duodenum and colon could be maintained in the system. FIG. 2L shows the perfusion of FITC and FITC-Dextran 4 kDa through each of the tissues over 2 hours, indicating these tissues could be used for perfusion studies. Although different permeability values were observed depending on the tissue used, these differences did not correlated between the different model drug used, indicating differences were not solely attributed to one specific factor, such as different surface areas.

Figure 2N:
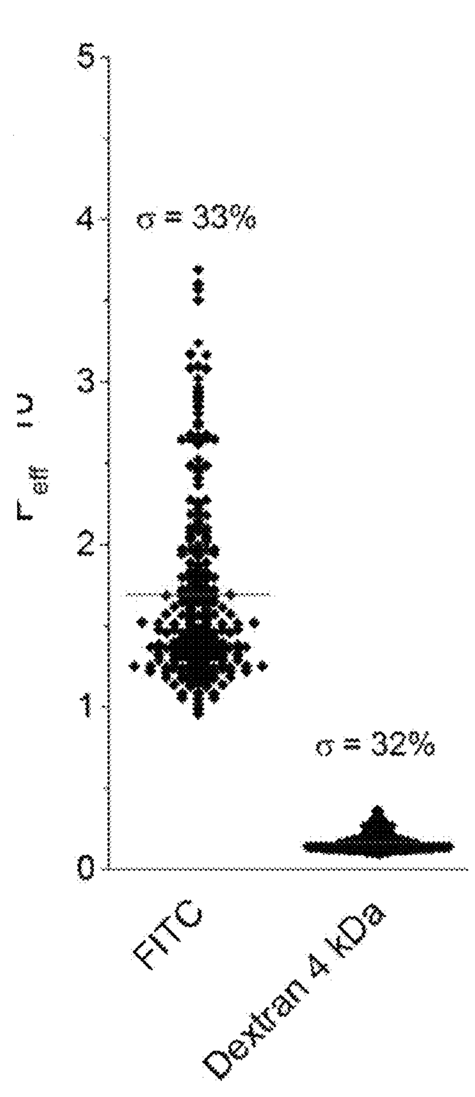
FIG. 2N is a graph depicting variability analysis of perfusion of fluorescein (FITC) and FITC-Dextran 4 kDa. Relative standard deviation (a) shows the variability across 500 samples each from 2 different animal batches.

In addition, the ability of the tissue to be used in a 384-well system was tested. The device manufactured included an upper load plate with 2 mm to 3 mm diameter posts and a 384 microplate with a glass bottom (Greiner Sensoplate™, Sigma; FIG. 2M). The perfusion of FITC and FITC-Dextran 4 kDa was measured over 2 hours. As shown in FIG. 2N, there was a relative standard deviation of around 30% when tested across 500 samples from 2 different animal batches, indicating the system could be increased to 384 wells.

Overall, these results indicated the intestinal tissue explants described herein were capable of being used in a high-throughput system.

Example 3: Intestinal Tissue Explant System Intestinal Absorption Validation

Figure 3A:
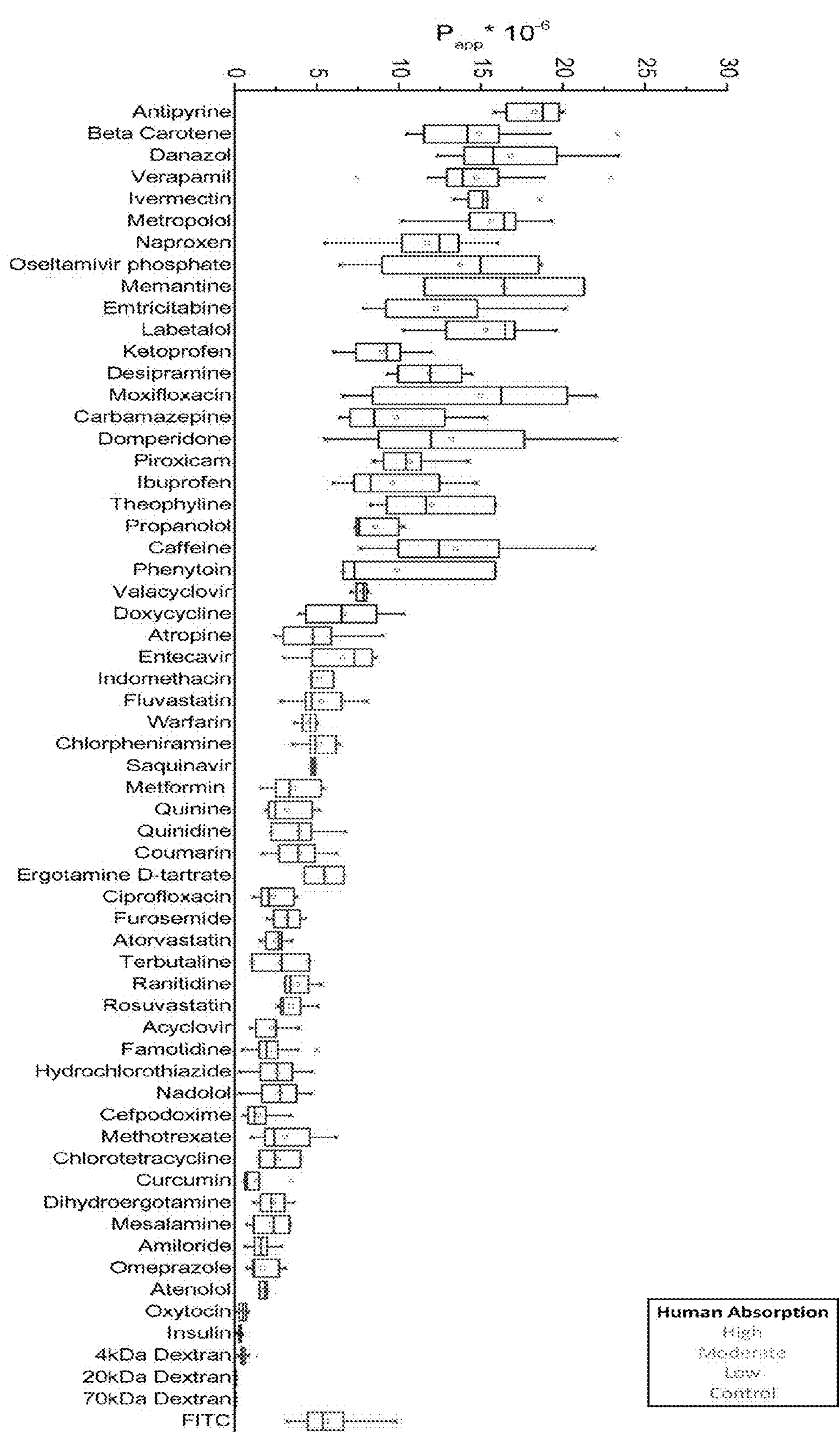
FIG. 3A is a box-plot graph showing perfusion analysis of around 60 model drugs from 6 independent experiments performed in duplicate.
Figure 3B:
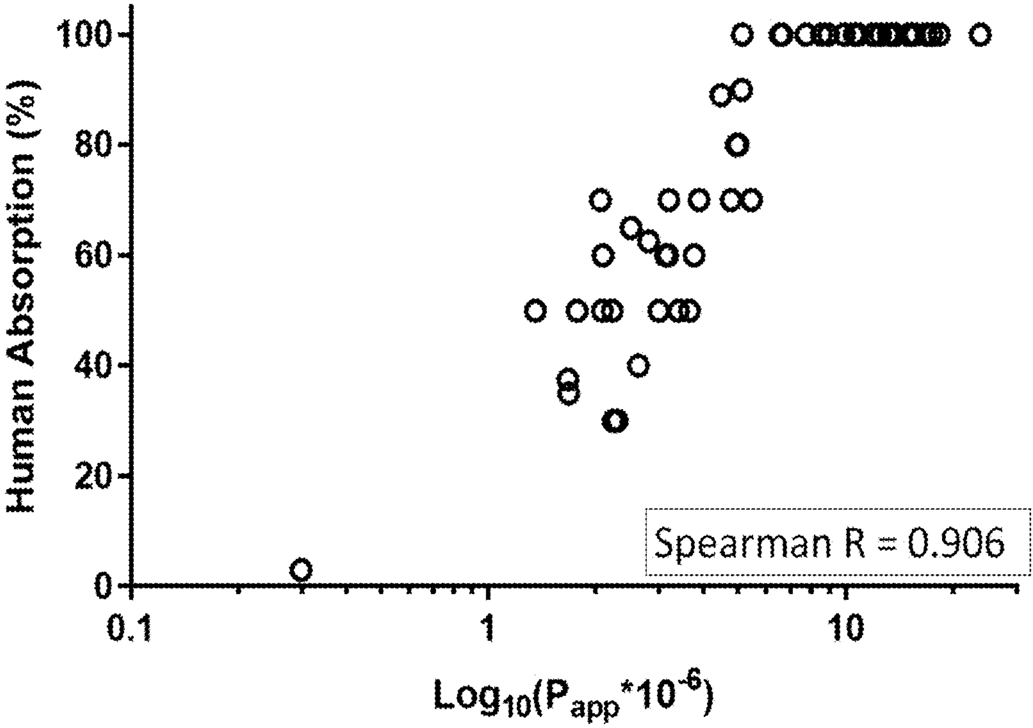
FIG. 3B is graph showing the correlation between perfusion values obtained from the intestinal tissue explant and human absorption reported in the literature.
Figure 3C:
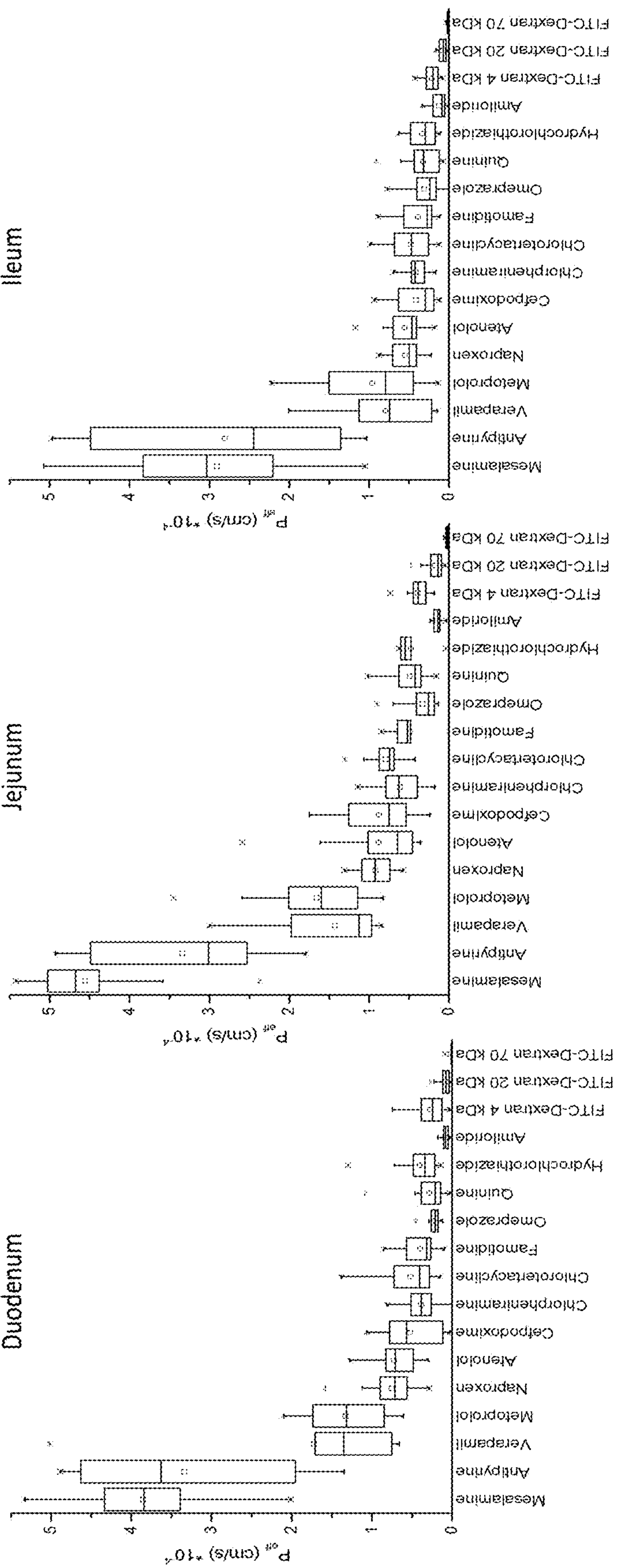
FIG. 3C provides box-plot graphs showing perfusion measurements of a panel of model drugs using different segments in the small intestine (duodenum, jejunum and ileum) over 3 independent experiments performed in quadruplicate (n=12).

The Food and Drug Administration (FDA), recommends using drugs approved for oral administration with human clinical pharmacokinetic data to validate the in vivo predictability of an in vitro intestinal perfusion system (Waiver of In Vivo Bioavailability and Bioequivalence Studies for Immediate-Release Sold Oral Dosage Forms Based on a Biopharmaceutics Classification System, *U.S. Dep. Heal. Hum. Serv. Food drug Adm. Cent. Drug Eval. Res.*, 2000). Therefore, to confirm the use of the intestinal tissue explant as a system for predicting intestinal absorption, the perfusion of 60 model drugs was analyzed. Specifically, drugs from the 4 Biopharmaceutical Classification System (BCS) classes (16 BCs class I, 13 BCS class II, 15 BCS class III, and 12 BCS class IV), along with 4 dextran-based control substances, were used. The intestinal perfusion data obtained from the intestinal tissue explant system was compared to human intestinal absorption based on previously published data. For quantitative detection of each model drug, a spectrophotometric detection method and calibration curve was established (data not shown). Data from 6 different animals was analyzed to determine batch-to-batch variability. FIG. 3A shows the results, wherein the box plot shows data of the 6 independent experiments performed in duplicate, and the approximate human in vivo intestinal absorption is shown as a percentage of total drug administered. The perfusion values obtained by the intestinal tissue explant system enabled the prediction of the approximate range of absorption for all model drugs tested. FIG. 3B shows the correlation between the average intestinal perfusion values and the reported human absorption data, providing a Spearman correlation coefficient of 0.906. Similar results were found using other parts of the small intestine (i.e., duodenum, jejunum and ileum) (FIG. 3C).

For comparison purposes, the in vivo predictability of the tissue explant system was compared to that of the Caco-2 transwell perfusion assay. A systematic literature analysis of Caco-2 transwell drug permeability was conducted for each drug used in the panel. The average Caco-2 permeability values compared to the human absorption data resulted in a Spearman correlation coefficient of 0.302 (data not shown). The possibility that the inherent genomic instability of the tumor derived Caco-2 cell line could increase variability in transport caused by variability in the expression level of drug transporters was investigated. The average coefficient of variation (CV) was found to be approximately two-fold higher in drugs actively absorbed compared to the passively absorbed drugs (data not shown). In contract, the CV across 6 independent animals in the tissue explant system was similar between active and passively absorbed drugs supporting the hypothesis that the genomically unstable background of the Caco-2 cells appears to increase the variability of actively transported drugs.

Figure 3D:
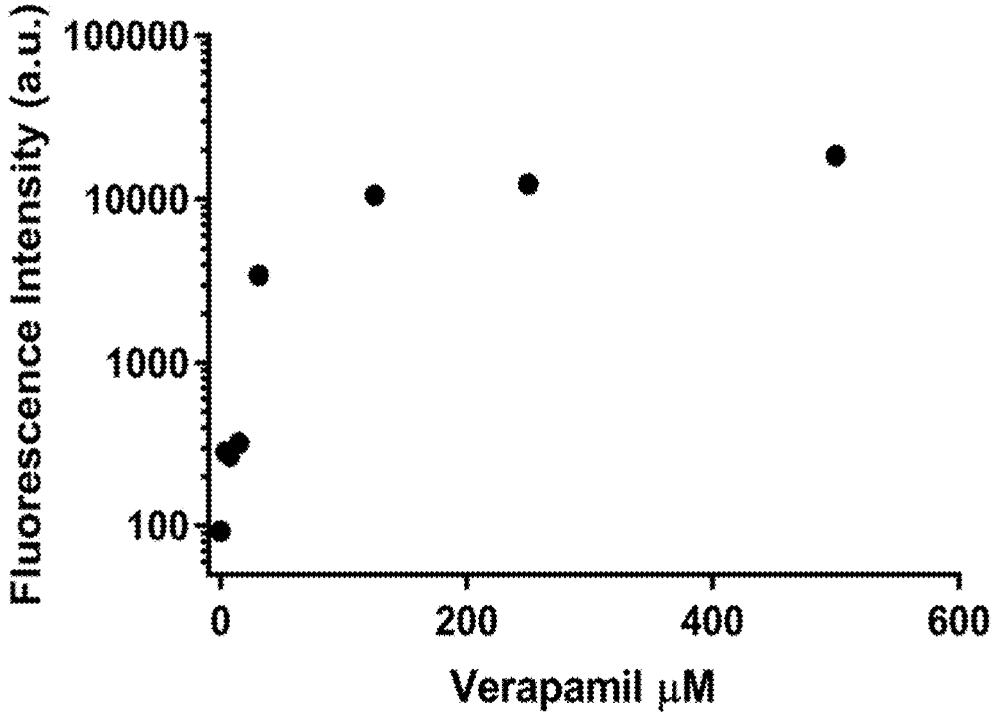
FIG. 3D is graph showing dose-dependent inhibition of intestinal absorption of a selective fluorescent substrate of MDR-1 in presence of various concentrations of the MDR-1 inhibitor verapamil.

Furthermore, the tissue explant was found to be useful for MDR-1 drug transporter inhibitor studies using a fluorescent MDR-1 specific substrate. The MDR-1 specific substrate fluoresces once it is absorbed by the tissue. Co-incubation of the substrate with various concentrations of a competitive inhibitor of the substrate, verapamil, resulted in a dose-dependent uptake that increased with increasing verapamil concentrations (FIG. 3D).

Figure 3E:
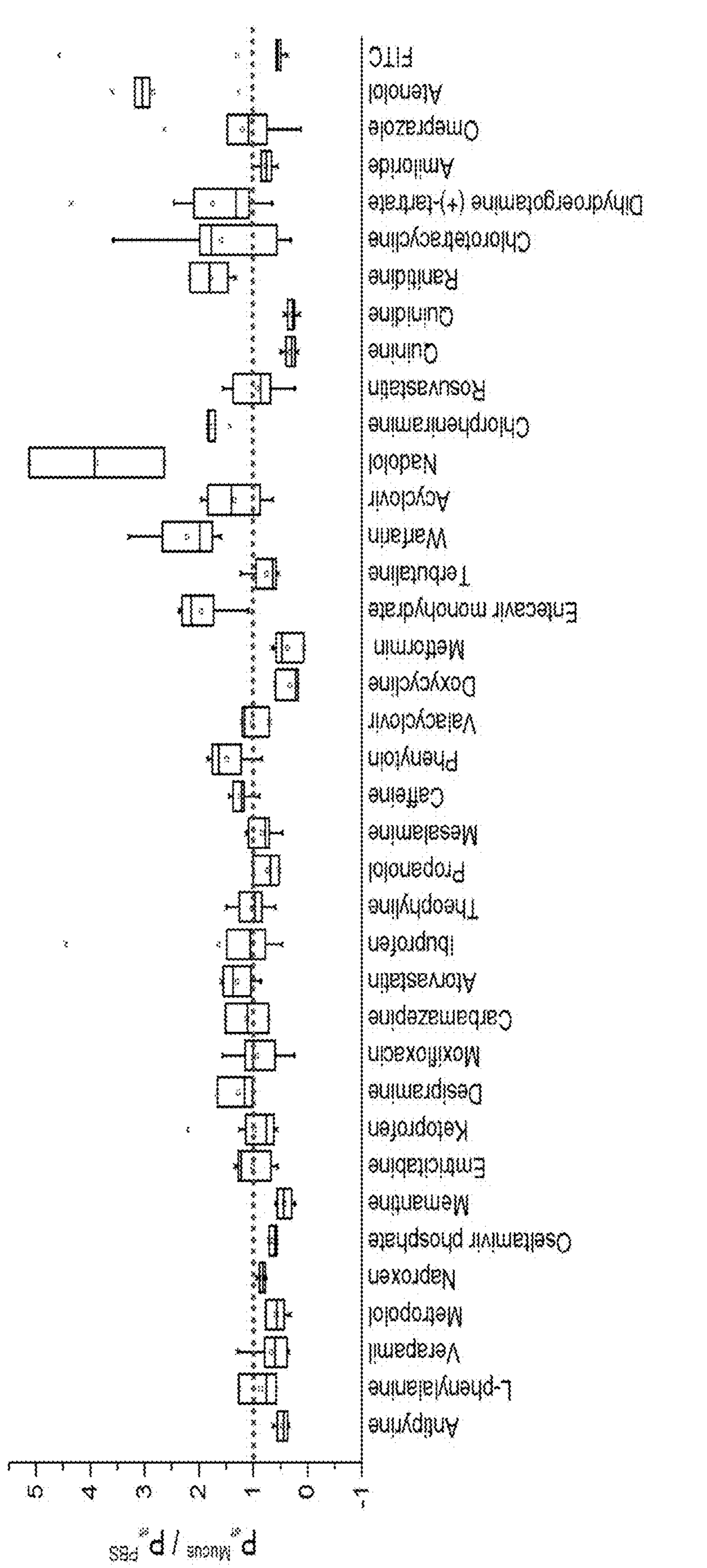
FIG. 3E is a box-plot graph showing perfusion analysis of model drugs in native intestinal fluid from 3 independent experiments performed in duplicate.

In addition, the use of the tissue explant in investigating drug-food interactions was explored. Drug-food interactions are known to play an important role in drug absorption. Specifically, the native intestinal fluid includes digested food, mucus and bacteria, and therefore impacts intestinal absorption. Unlike the Caco-2 transwell perfusion assay, the perfusion of model drugs through the intestinal tissue explant system was capable of being analyzed in the presence of native intestinal media. Native intestinal fluid was collected from the lumen of the jejunum of the same animal from which the tissue explant was isolated. The fluid was diluted with PBS at a 1:4 ratio and stored at −20° C. until needed. Model drugs were solubilized directly in the intestinal fluid, vortexed for 60 seconds, and then added to the tissue explant. As shown in FIG. 3E, the majority of the drugs showed either lower or higher drug absorption in native intestinal media, underlining the importance of analyzing drug absorption in the presence and absence of food.

Figure 4:
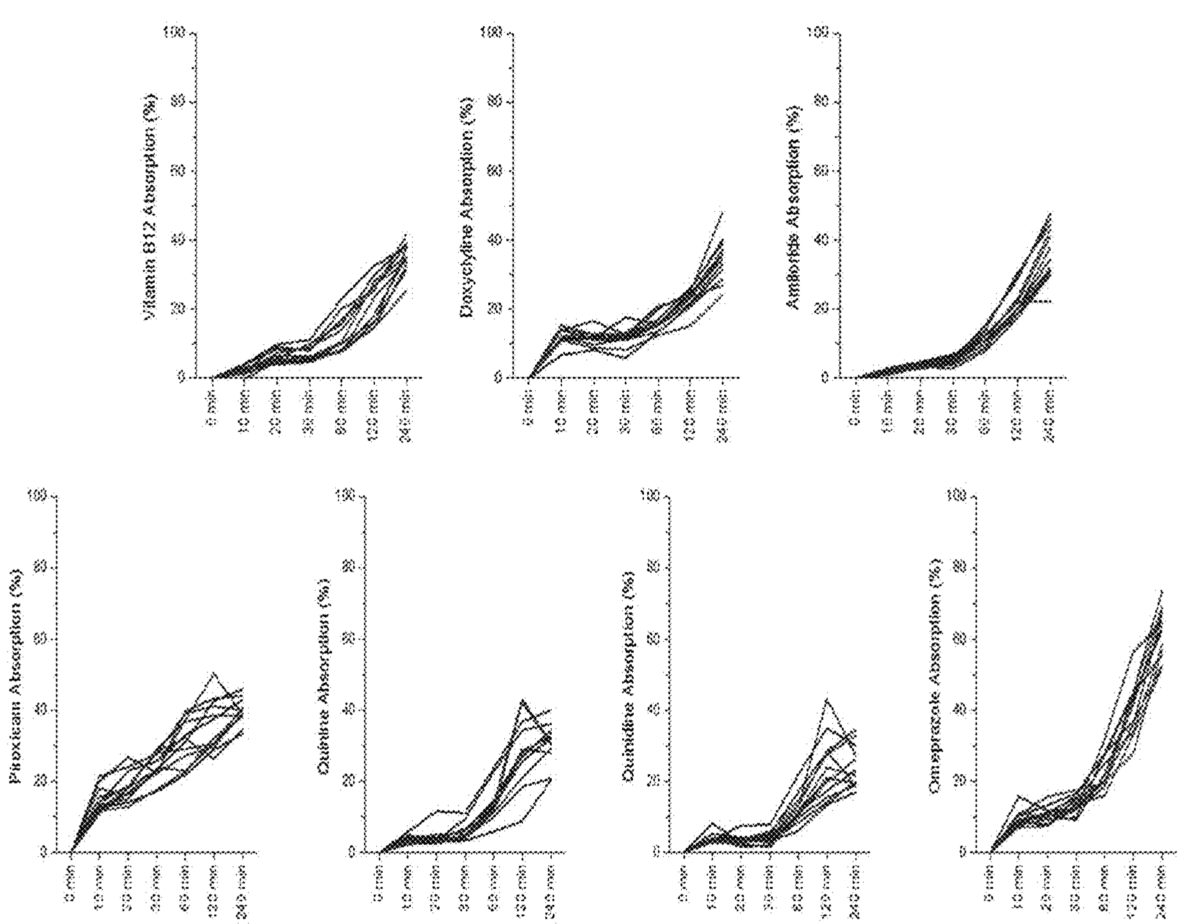
FIG. 4 provides graphs depicting perfusion time lapse analysis of various model drugs known to have slow, moderate or rapid intestinal absorption. Graphs show 12 individual time lapses over 4 hours.
Figure 4:
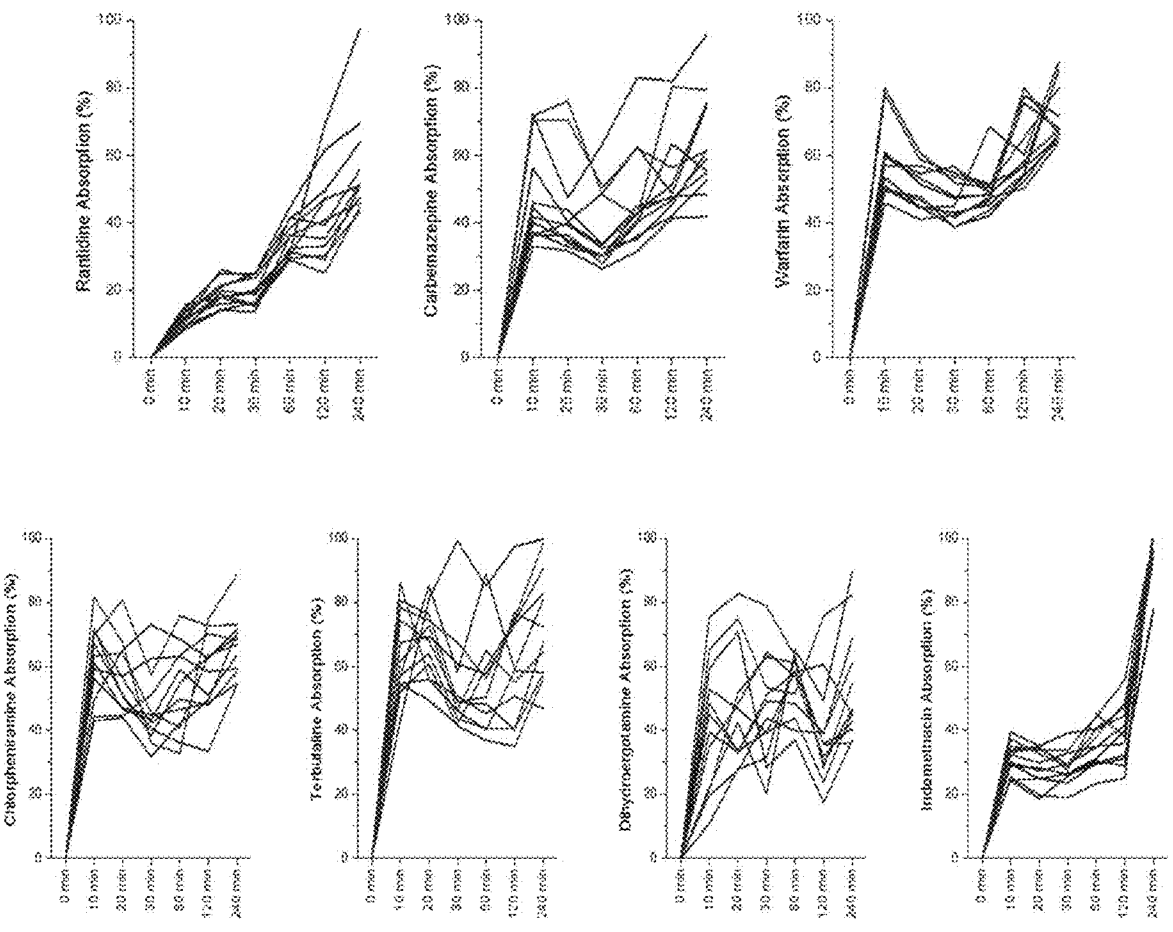
Figure 4:
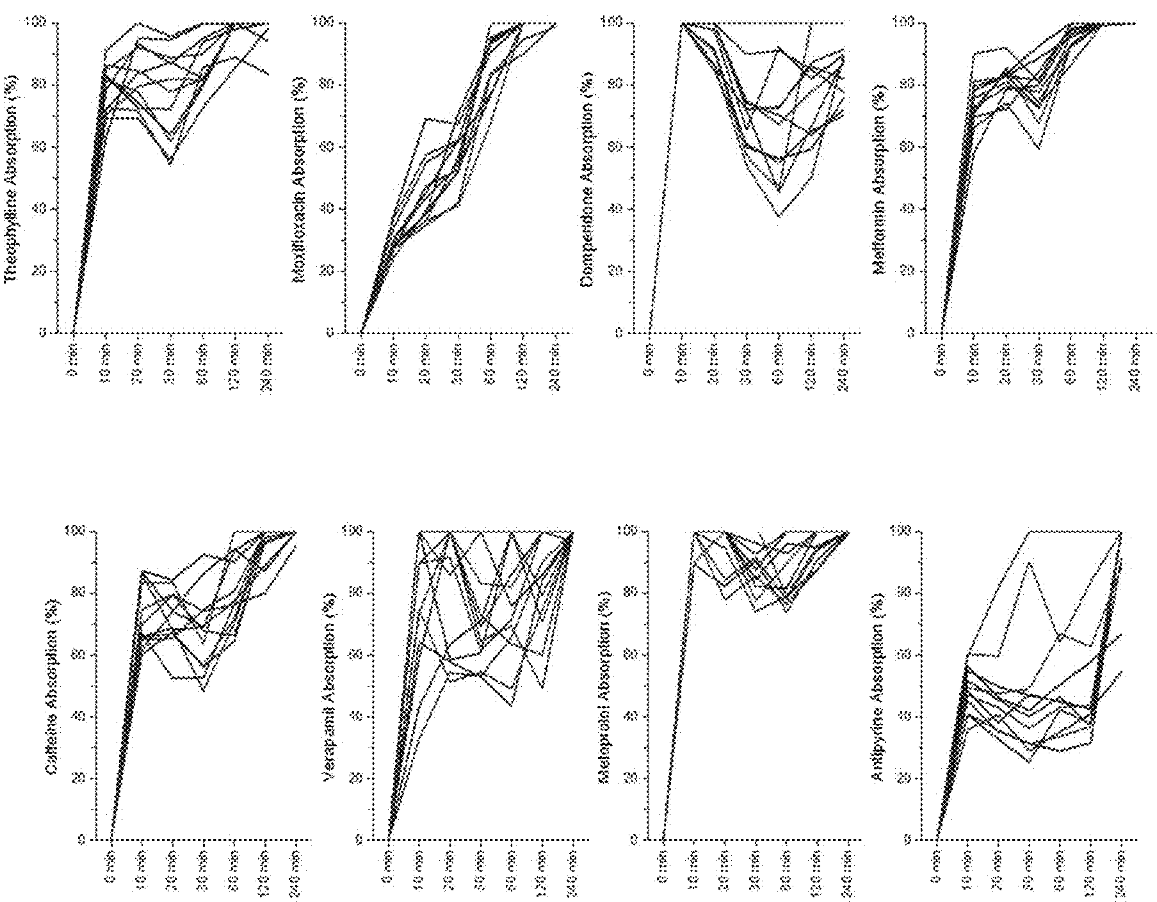

In addition to the overall amount of drug absorbed in the small intestine, the rate of absorption is another important factor. FDA prescription drug labels classify drugs as slow, moderate or rapid based on the peak plasma level in humans. A time-lapse perfusion analysis of model drugs in the intestinal tissue explant system was performed to establish absorption kinetics. FIG. 4 shows that time lapse analysis using the intestinal tissue explant system confirms a very clear absorption-over-time profile for slowly, moderately and rapidly absorbed drugs, and therefore the system can predict human in vivo absorption kinetics accurately.

For comparison purposes, computation analysis techniques to predict intestinal absorption of model drugs was used. Specifically, admetSAR, a model employed by drugbank.ca, and prediction based on Lipinski's "rule of five violations" (Lipinski, C. A., et al, Adv. Drug Deliv. Rev. Vol. 23: 3-25, 1997), were assessed. For the set of model drugs analyzed, neither method showed any correlation to human absorption data, suggesting very low predictive capabilities of these systems (data not shown).

Figure 5A:
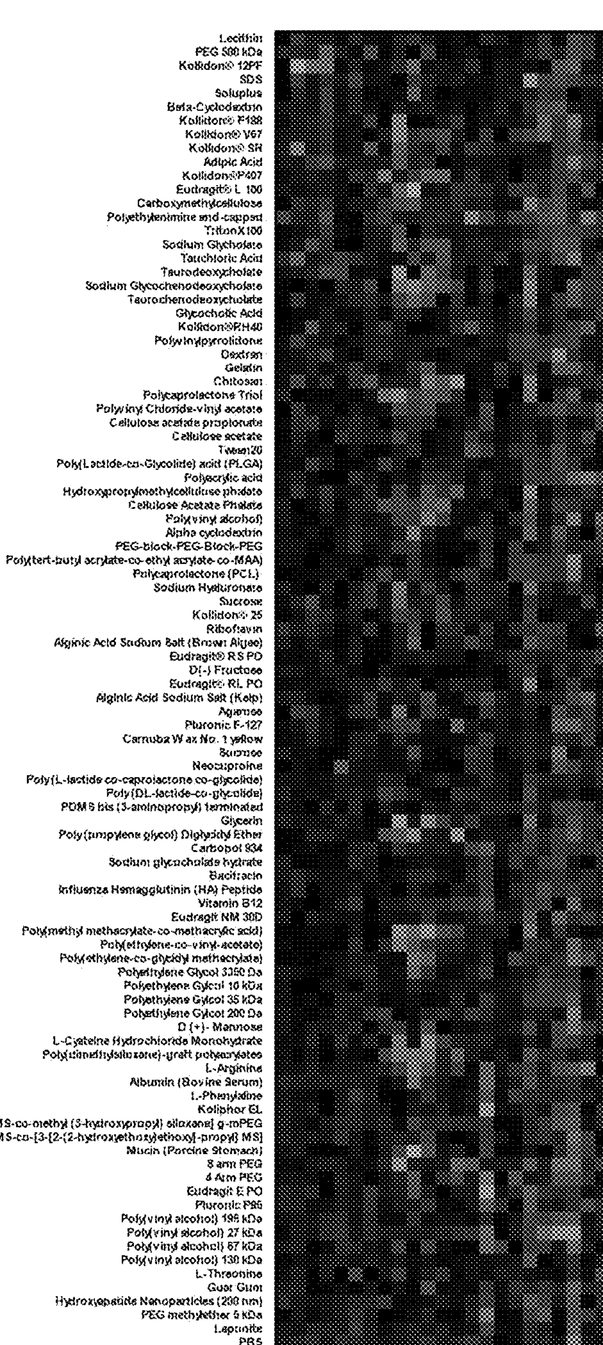
FIG. 5A provides a heatmap of the data obtained by perfusion screening of Alexa488-oxytocin formulated with 2976 formulations that are based combinations of 2 excipients. The color code indicates fold change compared to unformulated control (red=negative change, black=no change, green=3-fold increase, blue more than 3-fold increase).
Figure 5A:
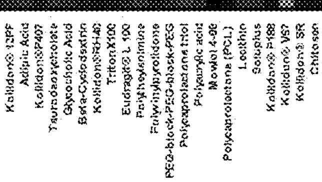
Figure 5A:
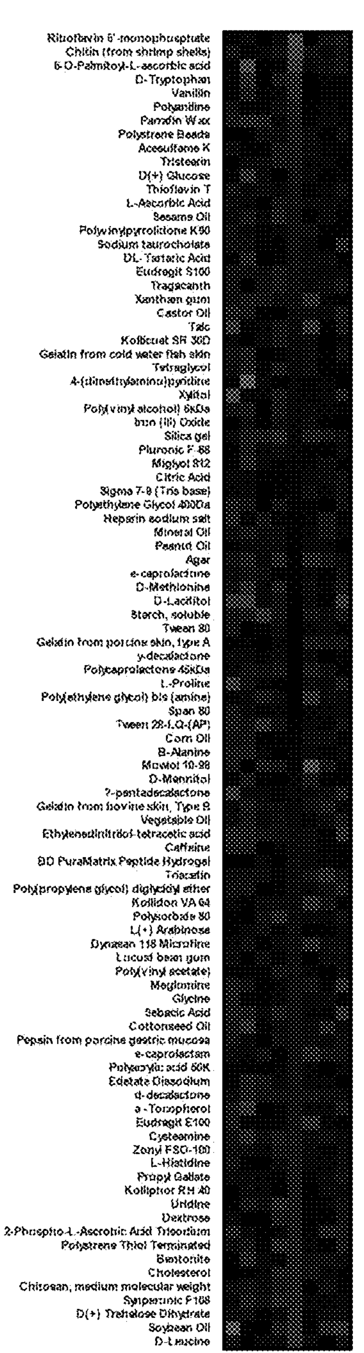
Figure 5B:
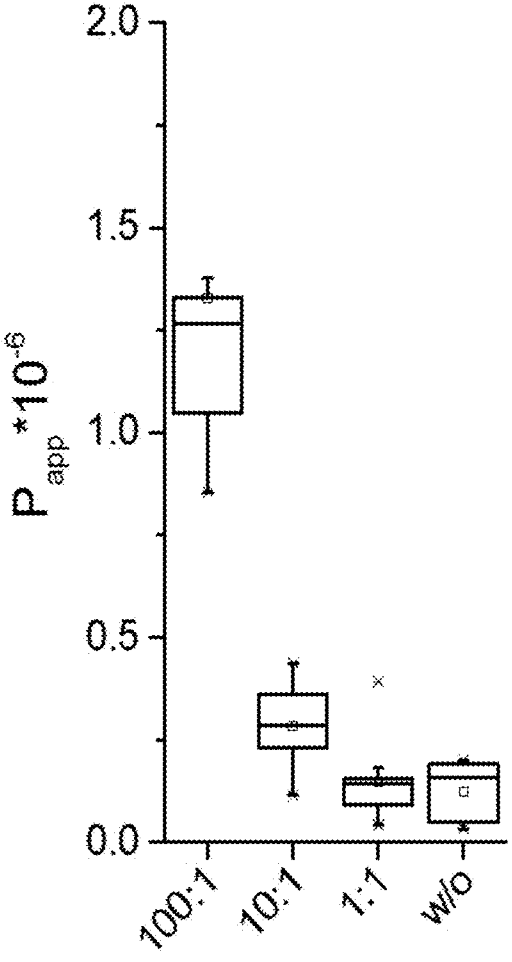
FIG. 5B is a box-plot graph depicting a dose-dependent validation experiment of Polyethyleneimine (PEI) used as an Oxytocin perfusion enhancer. Results show 3 independent experiments performed in duplicate.
Figure 5C:
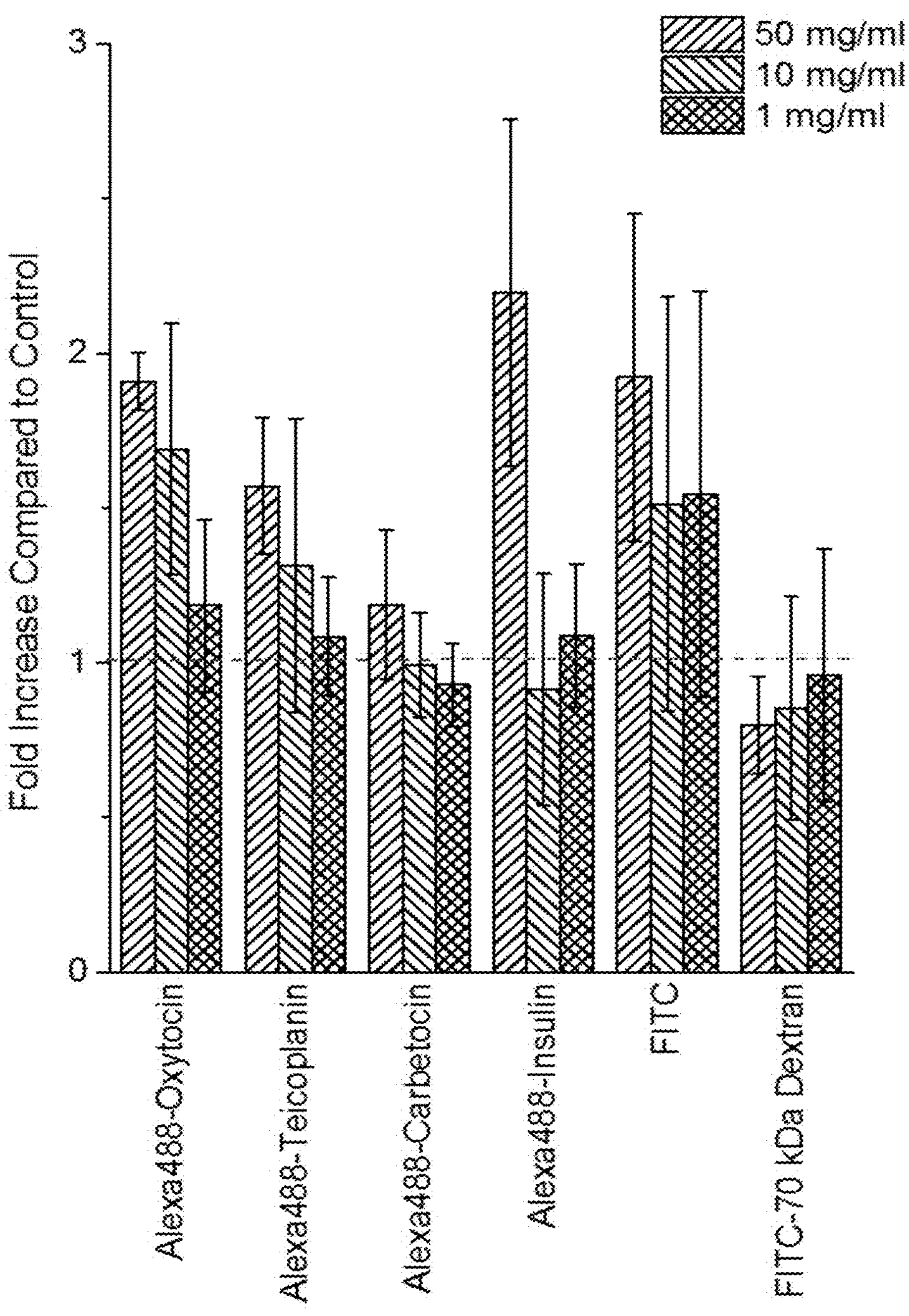
FIG. 5C is a bar graph depicting perfusion analysis of PEI formulations with various small or macromolecular model drugs. Results show 3 independent experiments performed in duplicate. Error bar shows standard deviation.
Figure 5D:
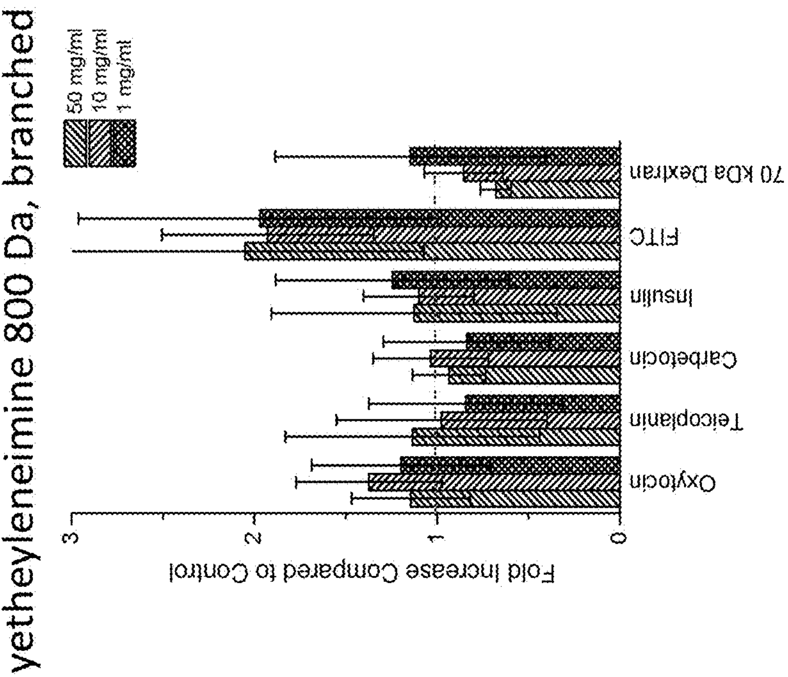
FIG. 5D provides bar graphs depicting perfusion analysis of PEI 25 kDa (left) and PEI 800 Da (right) with various small or macromolecular model drugs. Results show 3 independent experiments performed in duplicate.
Figure 5D:
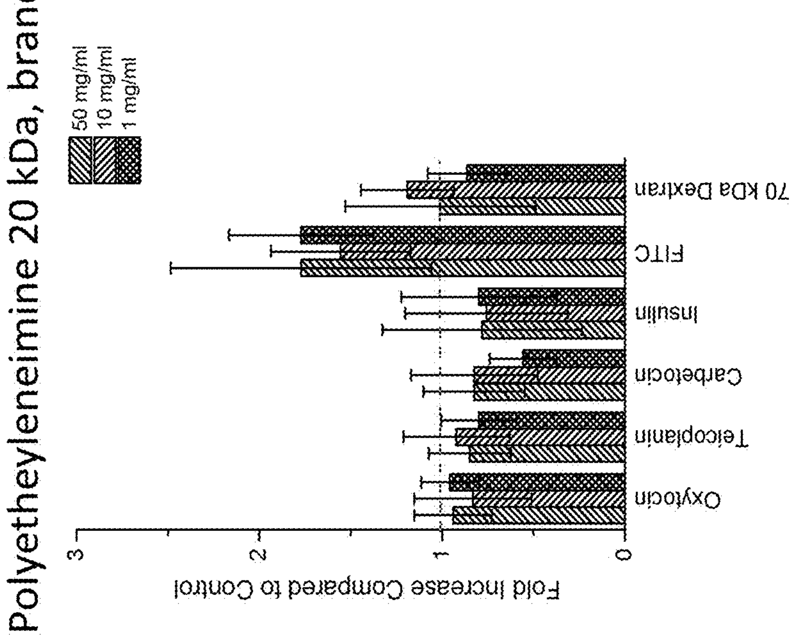
Figure 5D:

Example 4: Oxytocin Oral Formulation Development on the Intestinal Tissue Explant Platform Besides offering a higher in vivo predictability compared to the current state-of-the-art, the strength of the intestinal tissue explant system lies in its compatibility with high-throughput screens. To examine the potential of the tissue explant system for oral formulation development, a large-scale absorption screen was performed for the peptide drug oxytocin, which is currently not available for oral administration due to low intestinal permeability, with a library of GRAS (Generally Recognized as Safe)-based excipients that are either known absorption enhancers or have an unknown effect on intestinal absorption. 2976 co-excipient formulations in aqueous solution from diverse chemical groups were used with Alexa488 conjugated oxytocin. As shown in FIG. 5A, several formulations appeared to increase perfusion of oxytocin several fold. These formulations included hydrophilic polymers, surfactants and bile acid combinations. Additional screening and validation experiments were performed for initial screening hits (data not shown). Polyethyleneimine (800 Da, end-capped) consistently increased the intestinal perfusion of oxytocin several fold in a concentration-dependent manner (FIG. 5B). In addition, this formulation was tested with other model drugs, including Alexa488-teicoplainin, Alexa488-carbetocin and Alexa488-insulin, and appeared to increase the intestinal absorption to various degrees depending on the drug used (FIG. 5C). Other polyethyleneimine variants tested did not significantly enhance intestinal absorption of various drugs tested (FIG. 5D). Interestingly, limited increase in intestinal perfusion was observed for the oxytocin analogue carbetocin when formulated with polyethyleneimine (FIG. 5C). Furthermore, using a sub-panel of formulations, the correlation between fluorescence detection of Alexa488 conjugated oxytocin and ELISA detection of unlabeled oxytocin was investigated to address the concern that absorption measurements with fluorescently labelled oxytoxcin did not measure intact oxytocin and that a fluorescent label might affect oxytocin perfusion. The majority of formulations identified in the initial screen were confirmed by the ELISA analysis (data not shown).

Figure 5E:
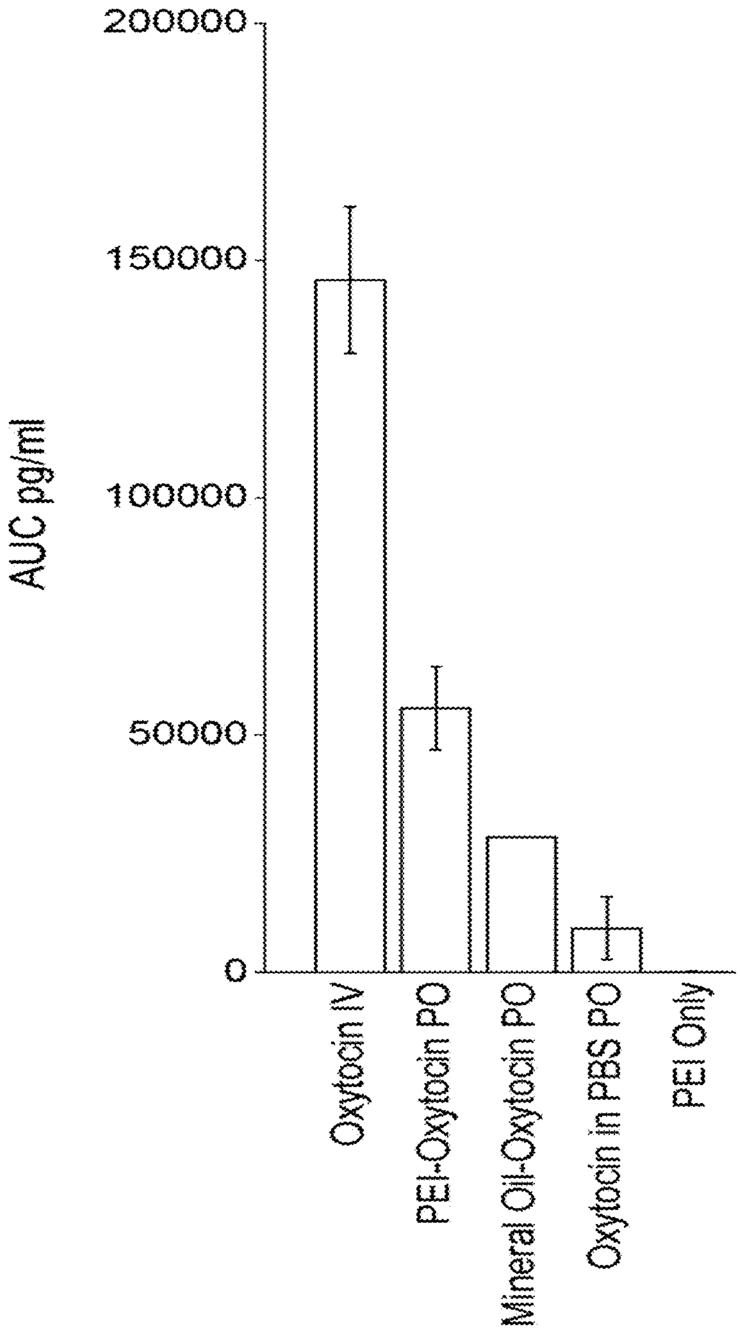
FIG. 5E is a bar graph showing accumulated plasma level concentration of PEI-Oxytocin, Mineral Oil-Oxytocin, Oxytocin only and PEI only in pigs over a time course of 2 hours. Results represent 4 experiments per condition.

Pharmacokinetic validation was performed in vivo. Female Yorkshire pigs between 45 and 50 kg in weight were used. Before every experiment, the animals were fasted overnight and on the day of the procedure, the morning feed was held. The animals were sedated with an intramuscular injection of Telazol (tileramine/zolazepam) 5 mg/kg, xylazine 2 mg/kg and atropine 0.04 mg/kg. The duodenum was accessed endoscopically and the formulation directly delivered to the duodenum. Serial blood sampling from the peripheral veins was performed for quantification of oxytocin. For oxytocin serum quantification, an Oxytocin ELISA kit (Cat. no. ab133050, Abcam) was used according to the manufacturer's protocol. The absolute bioavailability of oxytocin alone was found to be 0.64%, while oxytocin-PEI (800 Da, end-capped) and oxytocin-Mineral Oil (another hit from the screen) formulations resulted in average oral bioavailability of 3.8% and 2%, showing 6 and 3-fold enhancement respectively compared to the non-formulated oxytocin control (FIG. 5E). To investigate the mechanism of absorption enhancement and to analyze potential local effects of the formulation on the small intestine histologically, a surgical procedure coupled with custom-made devices was developed, that enabled controlled exposure of the formulation on a defined area of the intestinal tissue. E-cadherin stained sections of biopsy samples were used to analyze the disruption of cell-cell adhesions. Intestinal epithelium exposed to mixture of oxytocin-PEI (800 Da, end-capped) and oxytocin-Mineral Oil, showed no difference in cell-cell adhesion compared to non-formulated oxytocin and the non-treated control (data not shown).

An additional high-throughput screen was carried out with insulin, as a representative of a protein biologic, and a library of formulations, to identify enhancers of intestinal absorption (data not shown).

Overall, these results indicated the intestinal tissue explant system was useful for high-throughput screening and could accurately identify a formulation that enhances absorption.

Figure 6A:
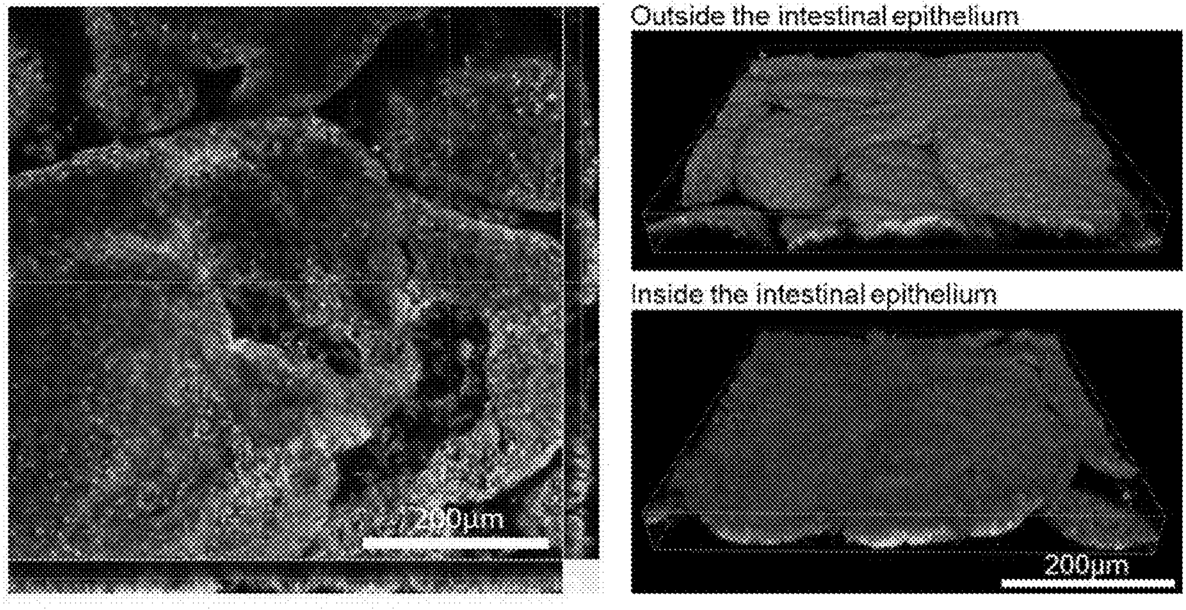
FIG. 6A provides images of confocal microscopy analysis of intestinal tissue explants transfected with cy3.3-siRNA using ultrasound. Scale bar=200 μm.
Figure 6B:
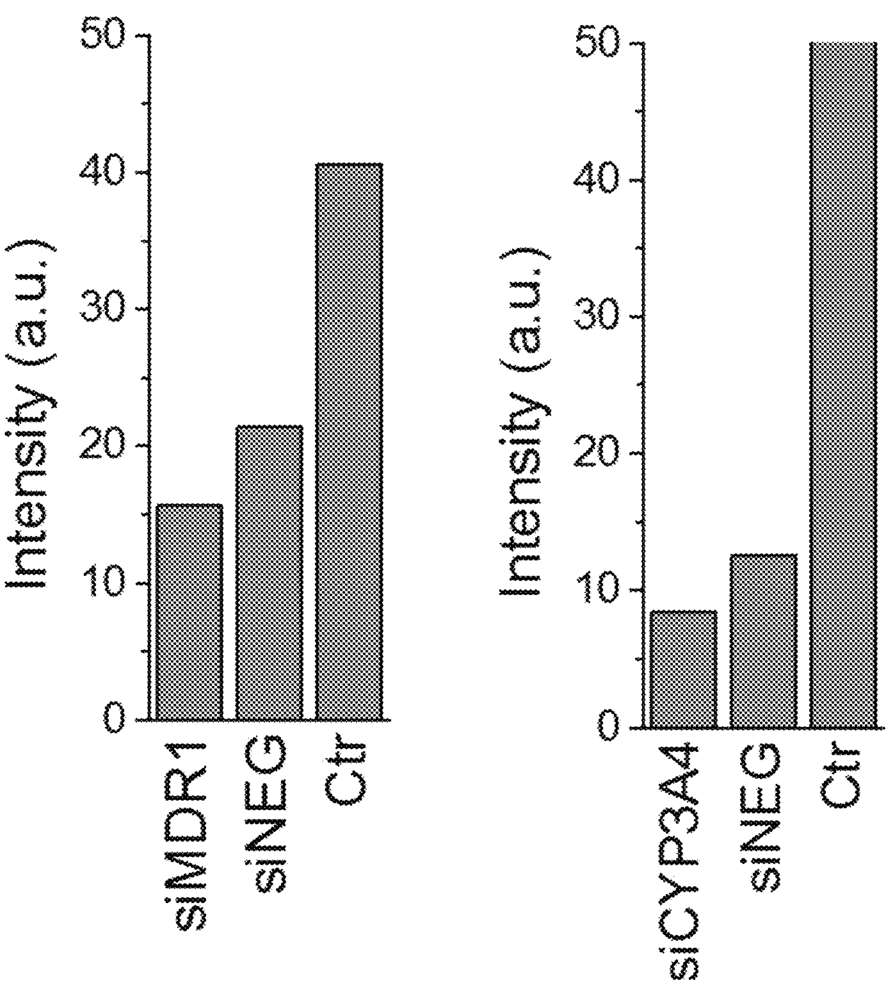
FIG. 6B provides graphs showing the quantification of Western blot analysis of lysates transfected with siABCB1 (MDR1) or siCYP3A4 compared to negative control siRNA (siRNA scrambled) and non-treated control after 48 hours incubation post transfection.
Figure 6C:
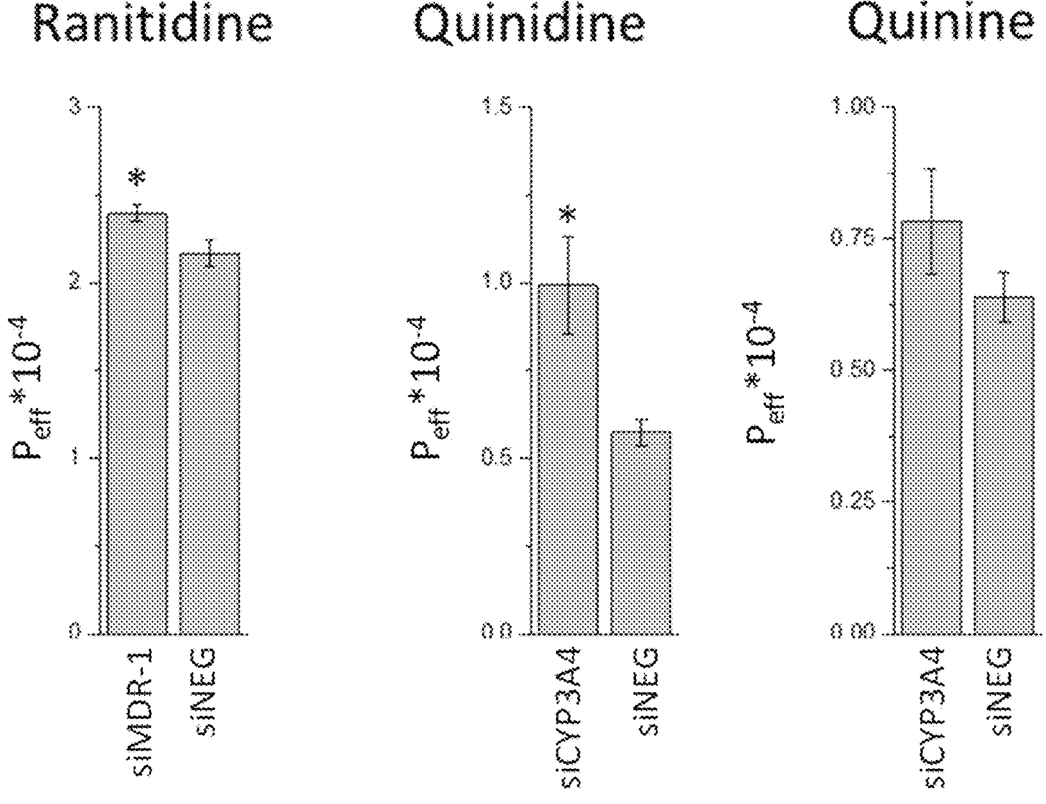
FIG. 6C provides bar graphs depicting perfusion analysis of Rantidine (CYP3A4 substrate) and Quinine and Quinidine (MDR-1 substrates) in intestinal tissue explants transfected with siCYP3A4 or siMDR-1. Results show 3 independent experiments performed in duplicate. Error bars show standard deviation.

Example 5: Nucleic Acid Delivery for Expression Modulation of the Intestinal Tissue Explant Platform Given the extended ex vivo viability of the intestinal tissue explant system, expression modulation using RNAi nucleic acids to study the effect of specific drug transporters or metabolizing enzymes for functional drug absorption studies was investigated. Ultrasound mediated siRNA delivery was found to be the most efficient transfection method (compared to Lipofectamine) as assessed by confocal microscopy-based analysis of fluorescently labeled siRNA (FIG. 6A). Specifically, siRNA was delivered to tissue explants using ultrasound by applying 5 second intervals for 1 minute for 40 kHz generated using a separate ultrasound generator (Sonics and Materials, Inc.) and a custom made 96 tip probe. The following siRNAs at concentrations of 1 μm in deionized water were used: Silencer® Select Pre-Designed siRNA (siRNA ID: s3846, Gene Symbol: CYP3A4), Silencer® Select Pre-Designed siRNA (siRNA ID: s10419, Gene Symbol: ABCB1), Silencer® Select Negative Control No. 1 siRNA. Knock-down of the efflux drug transporter MDR-1, as well as the metabolizing enzyme CYP3A4, were confirmed by western blot analysis and quantified as shown in FIG. 6B. Subsequent perfusion experiments with ranitidine and quinine, known substrates of MDR-1 and CYP3A4, respectively, resulted in a significant change of perfusion (FIG. 6C).

These results indicated the intestinal tissue explant system described herein was useful in studying the effect of drug transporters and metabolizing enzymes on drug absorption through the small intestine. In addition, these results confirmed the use of the intestinal tissue explant system in genetic engineering.

Example 6: Antisense Oligonucleotide Oral Formulation Development on the Intestinal Tissue Explant Platform As described in Examples 3 and 4, the tissue explant described herein was found to predict in vivo intestinal absorption and be useful in a high-throughput capacity for analyzing formulations of protein or peptide drugs to enhance such intestinal absorption. To further investigate the usefulness of the tissue explant, enhancement of absorption of antisense oligonucleotides was investigated.

Figure 7A:
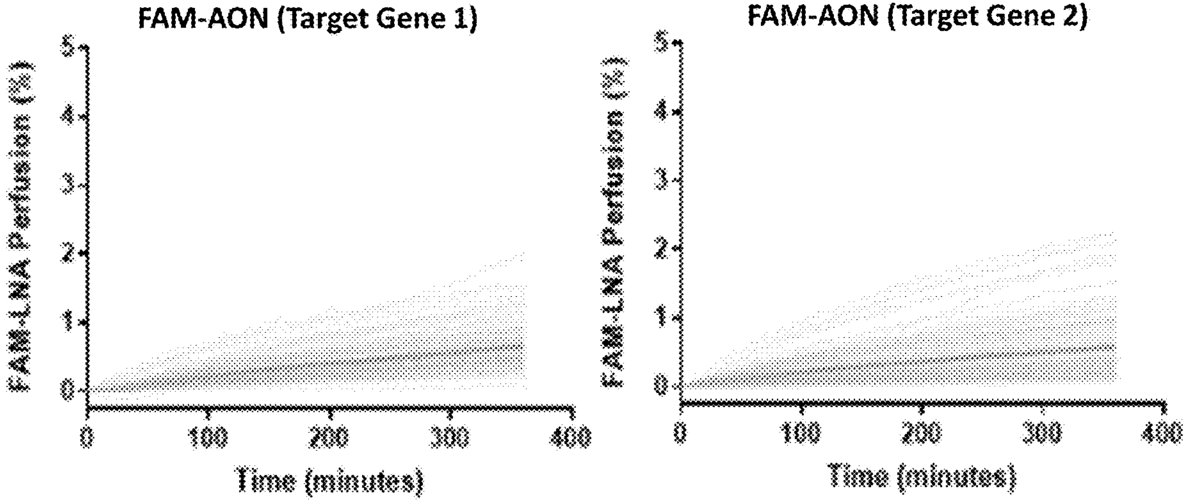
FIG. 7A provides graphs showing perfusion kinetics of FAM-labelled antisense oligonucleotides against two different target genes (Target Gene 1 & Target Gene 2) in small intestinal tissue explants over 6 hours with 500 samples each.

Oligonucleotides show low stability in the enzyme-rich GI tract, are unable to pass the mucus layer, and show very poor GI absorption (Ensigna, L. et al. Adv Drug Deliv Rev. Vol: 64(6): 557-570, 2012; Thomsen, T B et al. Nanoscale, Vol. 6(21): 12547-12554, 2014). Fluorescently conjugated antisense oligonucleotides (AONs) were used to detect accumulation and perfusion through the tissue explant. Specifically, automated high-throughput kinetic perfusion analysis with the tissue explant was found to be highly reproducible as assessed by measurements of 6-carboxyfluorescien (FAM) labelled AONs over different animal batches and part of the jejunum (FIG. 7A).

Figure 7B:
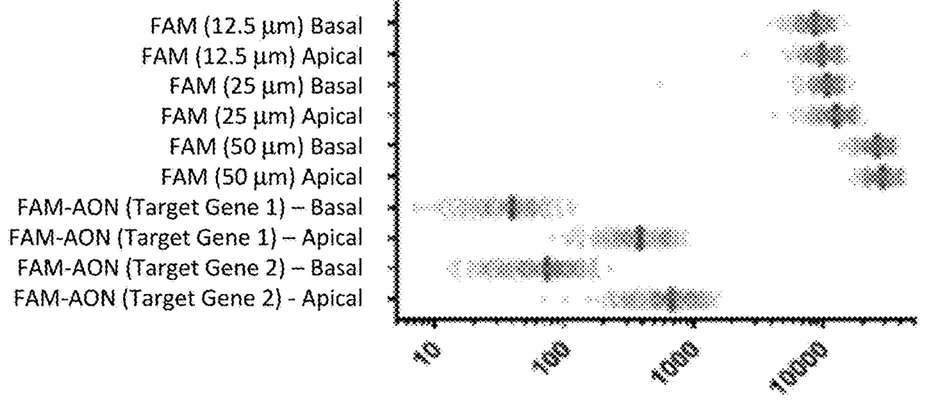
FIG. 7B shows variability analysis of FAM fluorescence signal of basal and apical small intestinal tissue incubated with antisense oligonucleotides against two different target genes (Target Gene 1 & Target Gene 2) as well as FAM only in various concentrations (n=192-288).

A high-throughput spectrophotometric based read-out method to measure FAM-AON tissue was developed and validated by confocal microscopy-based signal detection (data not shown). Automated high-throughput oligonucleotide apical and basal tissue accumulation measurements of FAM label only and FAM-AON across multiple animal batches and various segments of the jejunum demonstrated low variability and high reproducibility (FIG. 7B).

Figure 7C:
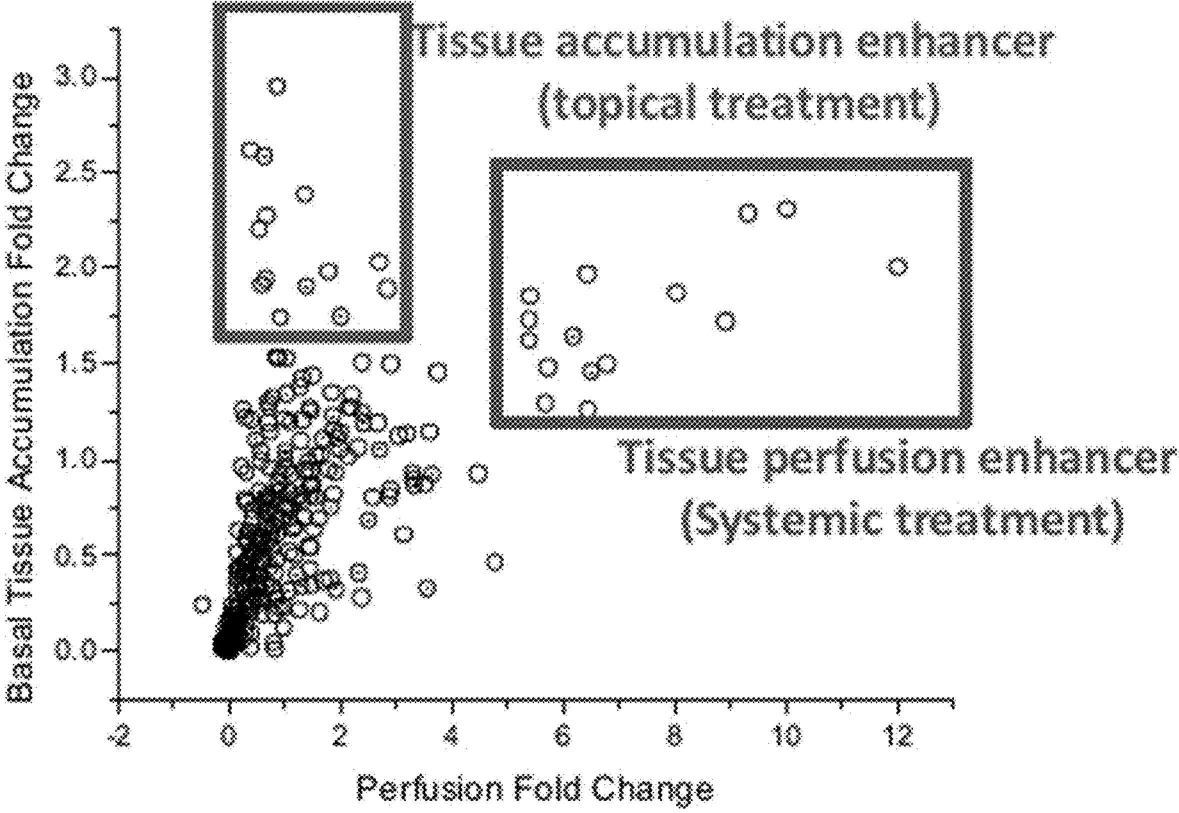
FIG. 7C is a graph showing results from a screening of co-formulations with FAM conjugated antisense oligonucleotides in small intestinal tissue explants, comparing basal tissue accumulation fold change and perfusion fold change to identify tissue accumulation enhancers and tissue perfusion enhancers.

Upon establishment of the assay, screening experiments were performed using formulations of FAM labelled AONs against two target genes. Intestinal perfusion and tissue absorption were measured simultaneously in real time. A custom designed diverse chemical compound library was utilized, which represented a wide range of chemical properties to identify compound that modulate local intestinal tissue uptake for topical treatment (defined as "intestinal absorption), or permeation through the intestinal tissue into systematic circulation (defined as "intestinal perfusion). FIG. 7C provides a graph showing tissue accumulation enhancers relative to tissue perfusion enhancers.

Moreover, a 4D confocal imagine technique to enable evaluation of the 3D displacement of fluorescently labelled AON in native intestinal mucus over time was developed to measure the diffusion within the mucus. Detection of FAM-AON homogenously distributed in freshly harvested native porcine intestinal mucus was established. Addition of FAM- AON solution on top of the mucus layer followed by 4D confocal imaging showed clear signal displacement over time (data not shown). Various formulations were investigated for changes in mucus diffusion, and those that resulted in multiple fold increases in diffusion were found to correlate with an increased ratio of permeability and absorption of intestinal tissue with mucus layer intact over intestinal tissue with the mucus layer washed away (data not shown).

Figure 7D:
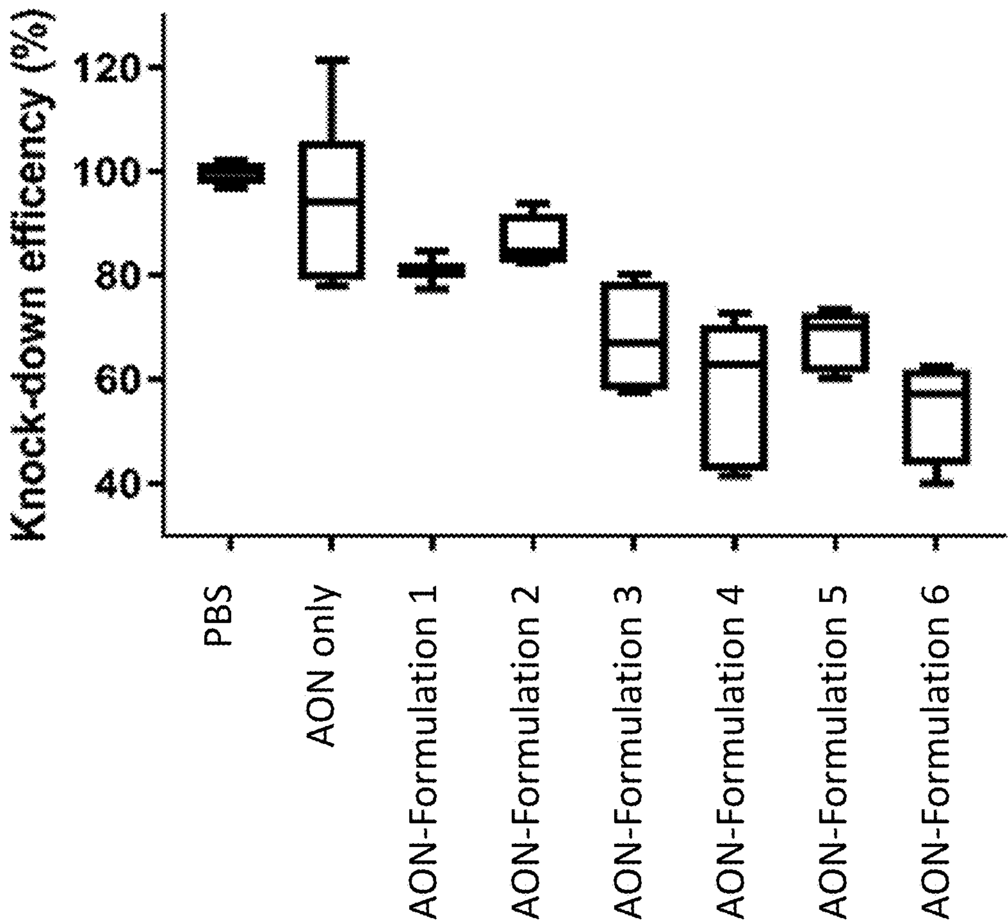
FIG. 7D is a box-plot graph showing percentage of knock-down efficiency of an antisense oligonucleotide against a target gene (Target Gene 1) in small intestinal tissue explants, wherein the antisense oligonucleotide was formulated in 6 different formulations.

Upon validation analysis of the formulations, a set was selected for non-labelled AONs and tested for topical gastrointestinal therapeutic efficacy following GI delivery in Yorkshire pigs. Biopsy samples from the area treated were analyzed histologically by ISH staining to investigate uptake of intact AON as well as by rtPCT to confirm efficacy. FIG. 7D shows efficacy of formulated AON, while non-formulated AON had no effect compared to non-treated control.

These results indicated the intestinal tissue explant was useful for high-throughput screening for antisense oligonucleotides and could accurately identify formulations that enhance knock-down efficacy as well as tissue accumulation and/or tissue perfusion.

Example 7: Absorption-Dissolution Assay on the Intestinal Tissue Explant Platform Next, the intestinal tissue explant was investigated for its use in simultaneously assessing the dissolution and absorption of a compound of interest. The effectiveness of a compound in a dosage form relies on the drug dissolving in the fluids of the gastrointestinal tract prior to absorption into the systemic circulation. Dissolution is a standardized method for measuring the rate of drug release from a dosage form. 70% of drugs currently in development are classified as BCS class II (low solubility/high permeability). A problem with focusing on formulations that enhance solubility, is that it may affect permeability. Accordingly, simultaneously analyzing the effects of a formulation on dissolution and absorption is ideal.

Figure 8:
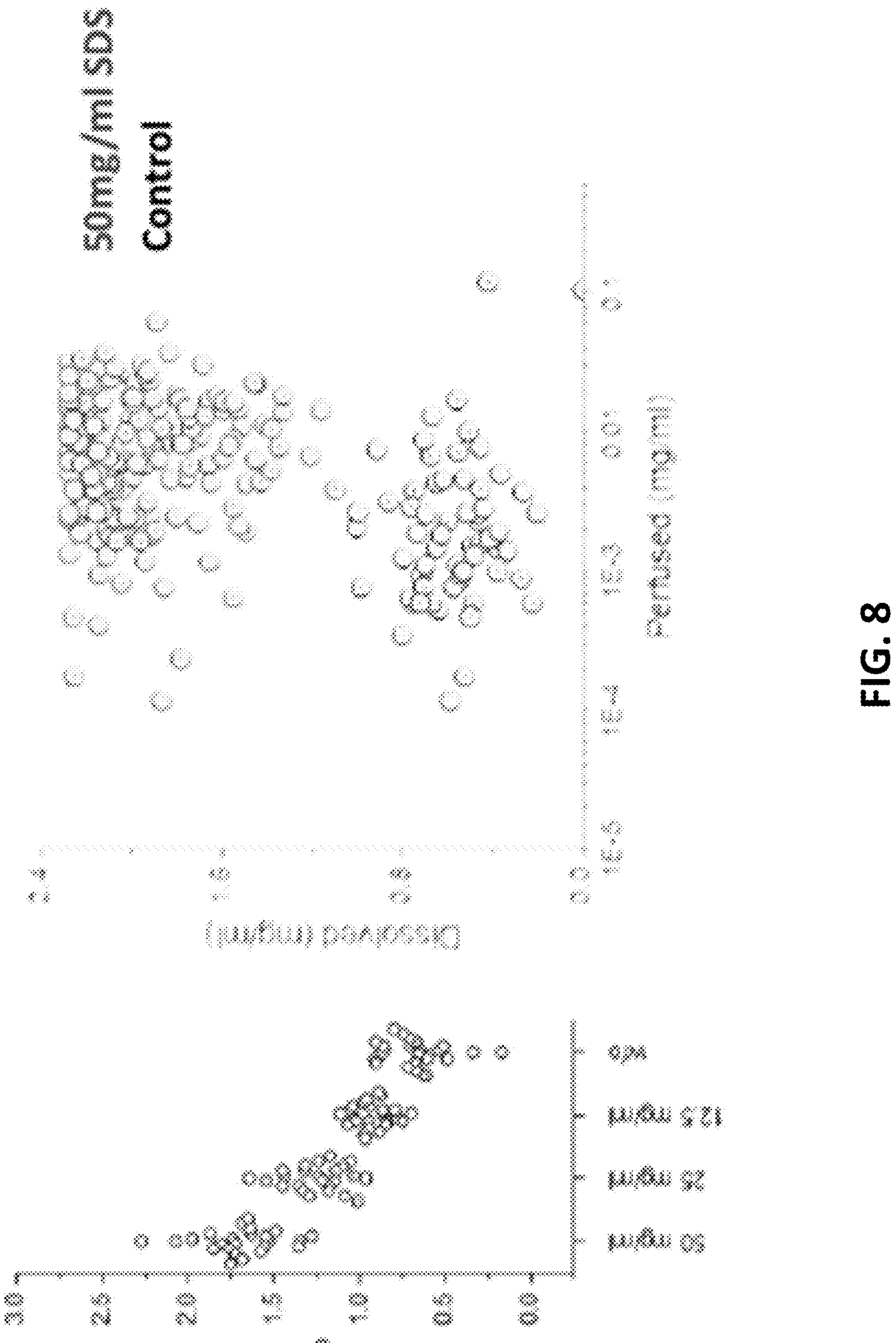
FIG. 8 provides graphs showing dissolution data of indomethacin formulated in SDS at various concentrations (left), and comparison of dissolution and absorption values obtained from intestinal tissue explants treated with indomethacin formulated in SDS or non-formulated.

To investigate the use of the intestinal tissue explant in simultaneously assessing dissolution and absorption the following method was utilized: (1) combination of drug+solvent to form a solution of soluble drug in high concentration; (2) evaporation of the solution to form a drug power; (3) combination of the drug power with an excipient library in aqueous buffer solution or native gastrointestinal fluids; (4) separation of solubilized and non-solubilized drug by centrifugation; (5) spectrophotometric detection of drug concentration in supernatant to obtain dissolution data; (6) contacting the intestinal tissue explant with the supernatant; and (6) spectrophotometric detection of perfused drug concentration (i.e., absorption assay described in Examples 2 and 3). The validation of this method was carried out with indomethacin with SDS. FIG. 8 provides both dissolution data (left) and comparison of dissolution and absorption data (right). Formulations that enhance both dissolution and absorption can be identified.

Figure 9:
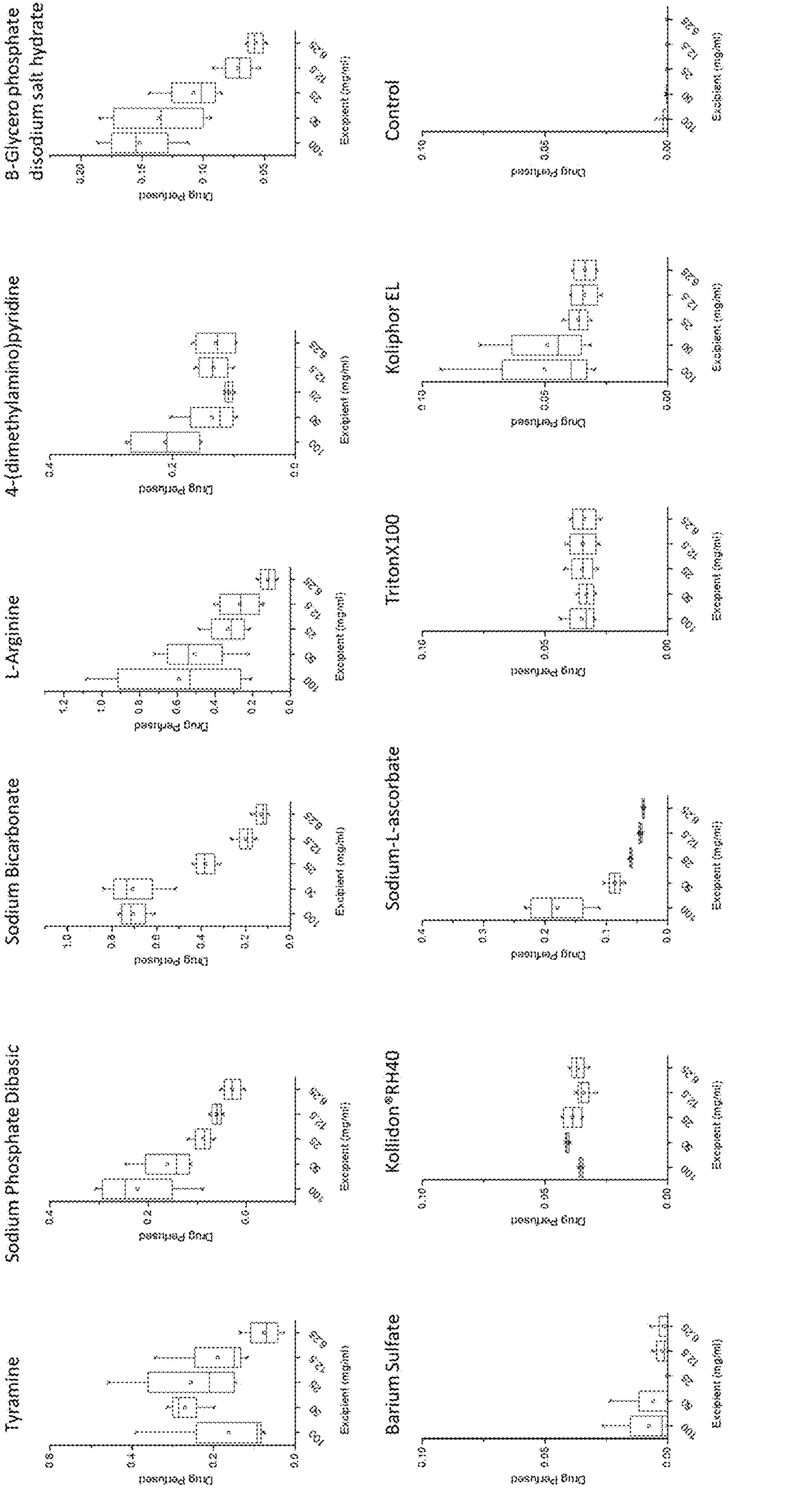
FIG. 9 provides graphs showing perfusion of meloxicam formulated in the indicated formulations in intestinal tissue explants in the presence of intestinal fluid, wherein concentration of meloxicam was fixed.
Figure 10:
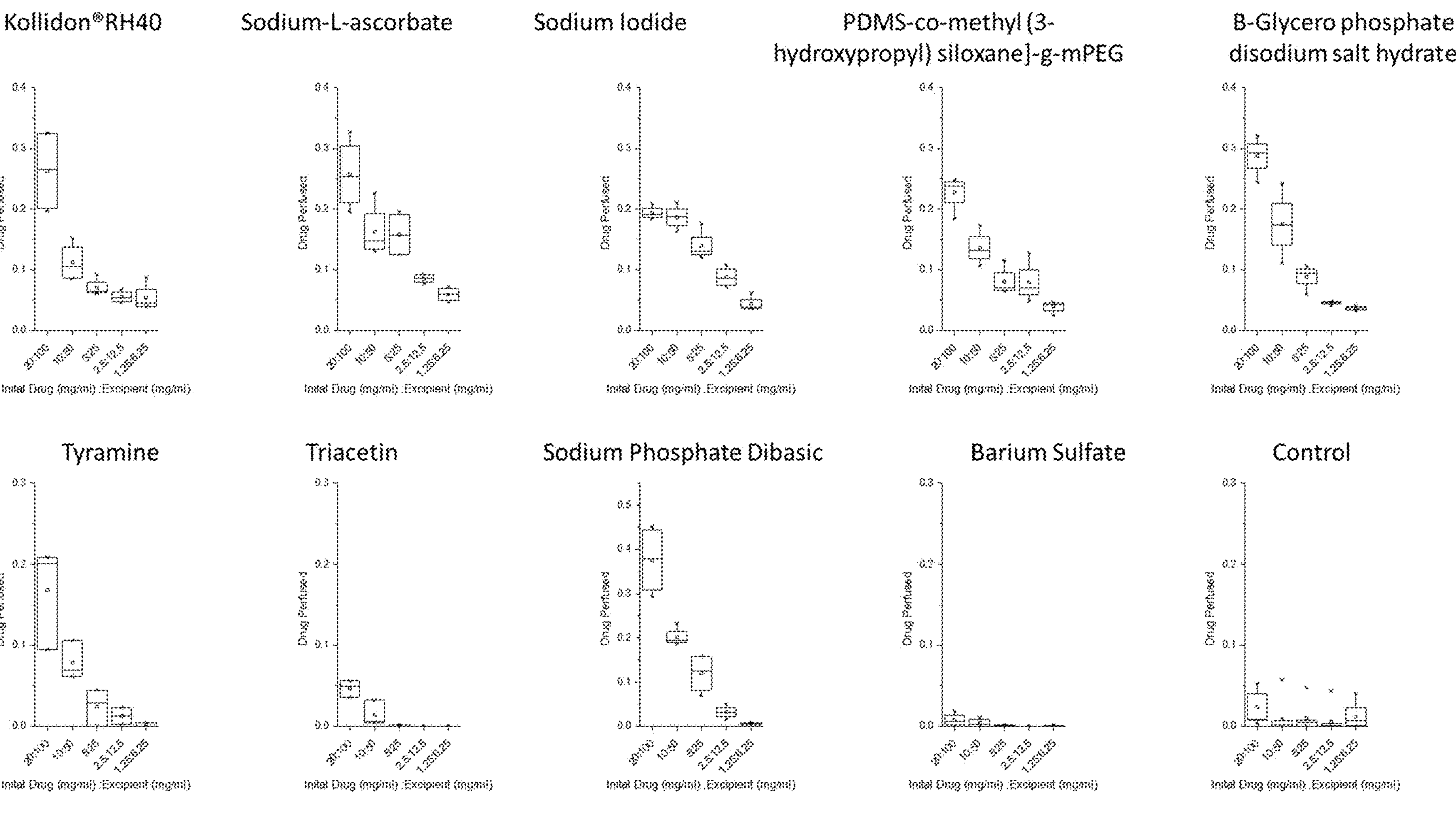
FIG. 10 provides graphs showing perfusion of meloxicam formulated in the indicated formulations in intestinal tissue explants, wherein different meloxicam concentrations were tested to mimic dilution in the intestine.

Further, simultaneous dissolution and absorption high-throughput screens were carried out using indomethacin, meloxicam and furosemide. Indomethacin and meloxicam are BCS class II drugs, whereas furosemide is a BCS class IV drug (low solubility/low permeability). Based on this screening, several formulations for meloxicam were further tested. FIG. 9 shows the dose-dependent effect of excipients on absorption of meloxicam in fixed drug concentration (20 mg/ml) in the presence of intestinal fluid. FIG. 10 shows absorption using different concentrations of drug-excipient formulations, with a constant ratio), to mimic dilution in the intestine. Rather than changing the tissue area this enabled maintenance of the high throughput capability of the system. Specifically, the drug and excipient concentration was systematically changed to mimic the changes in surface area within the gastrointestinal tract. The drug excipient solution can be prepared in any transport buffer as well as native gastrointestinal fluid. The highest drug excipient concentration was determined according to the water solubility limit of the drug. The concentrations used include concentrations above the drug solubility limit in water in and concentrations within the solubility limit. This assay enabled analysis of formulation dependent intestinal drug absorption enhancement of poorly soluble drugs, and found it is dependent on the surface area that the formulation is exposed to.

These results indicated the intestinal tissue explant is useful for identifying formulations that enhance dissolution and absorption in a high-throughput and efficient manner.

Figure 11:
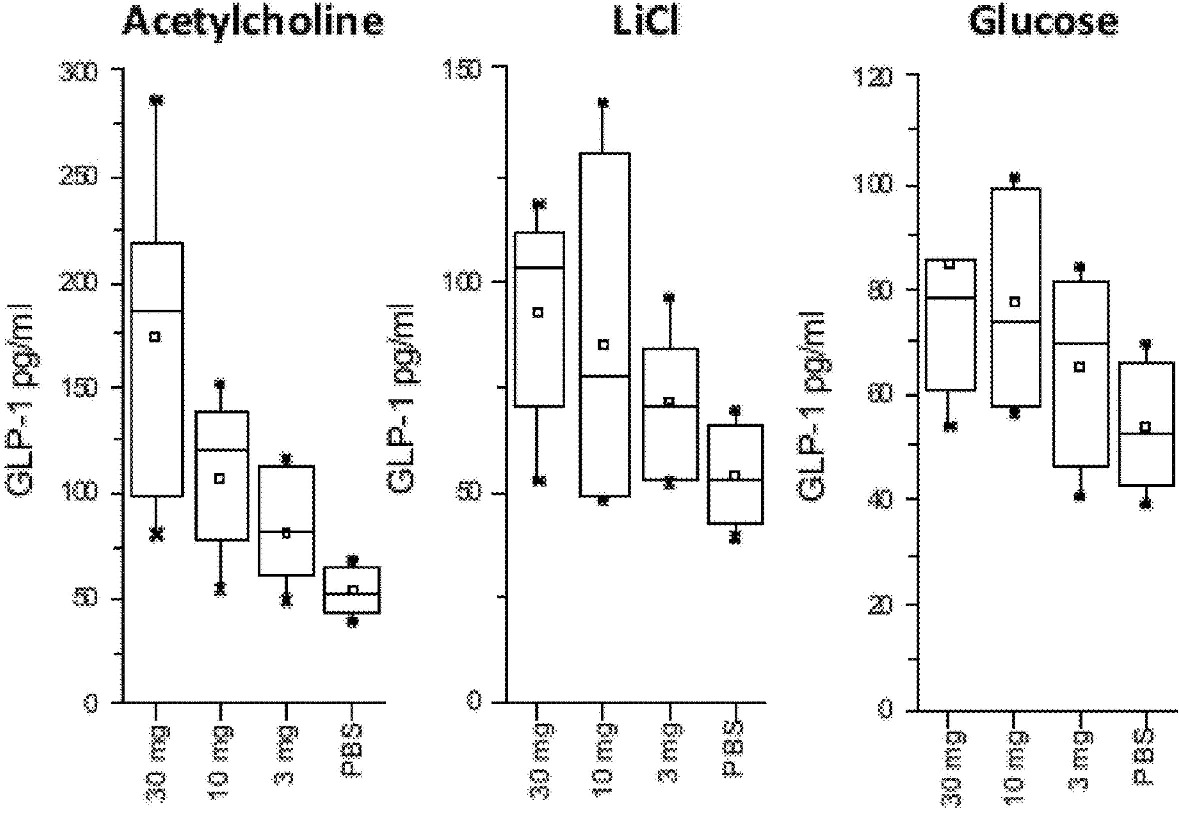
FIG. 11 provides graphs showing GLP-1 stimulation of intestinal tissue explants, as determined by ELISA, upon treatment with known GLP-1 stimulators acetylcholine (left), LiCl (middle) and glucose (right).

Example 8: Endocrine Stimulation Screening in the Intestinal Tissue Explant Platform As determined in Example 1, the intestinal tissue explant comprises endocrine cells, determined by the expression of Claudin-1 and Glucagon-like peptide-1 (GLP-1). Therefore, the ability of the intestinal tissue explant to respond to known GLP-1 stimulants was investigated. Specifically, acetylcholine, LiCl, and glucose were added to the intestinal tissue explant at varying doses for 24 hours, then cells within the apical side of the intestinal epithelium were isolated. The concentration of active cleaved peptide of GLP-1 (GLP-1 (7-36)) of these cell lysates was determined by ELISA analysis. As shown in FIG. 11, the intestinal tissue explant were found to show increased concentration so of GLP-1 (7-36) in a dose-dependent manner in response to the known stimulants. The stimulation of GLP-1 secretion by acetylcholine, LiCl and glucose, which act through different pathways, indicated these pathways were intact in the intestinal tissue explant. The Acetylcholine and LiCl act as non-nutrient stimulators of GLP-1 that are reported to simulate GLP-1 activity via neuronal regulation. Glucose triggers GLP-1 activity via nutrient-based pathways.

Based on these results, a screen of 600 compounds based on a kinase library and 240 GRAS/inactive ingredient compounds were tested for GLP-1 stimulation (data not shown). GLP-1 simulants can be used for various treatment applications including type 2 diabetes and obesity.

These results confirmed the presence of responsive endocrine cells in the intestinal tissue explant, and the usefulness of the tissue explant in identifying formulations that stimulate GLP-1 secretion.

Example 9: Toxicity Screening of the Intestinal Tissue Explant Platform

Gastrointestinal side effects are common in virtually all orally administered drugs. It is estimated that gastrointestinal side effects account for 20-40% of drug induced adverse effects (DIAE). DIAE account for 100,000 deaths per year in the USA and account for 5% of all hospital admissions. Ways to lower the gastrointestinal side effects of existing drugs are needed but challenges to test for local gastrointestinal toxicity form a major barrier. Accordingly, the use of the intestinal tissue explant to test and predict gastrointestinal toxicity was investigated.

Figure 12:
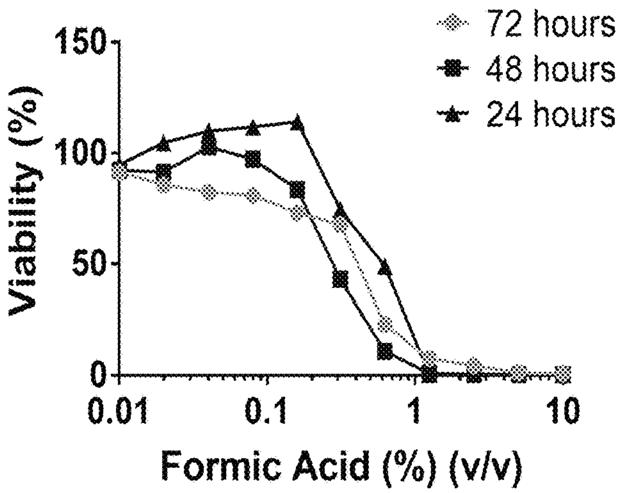
FIG. 12 shows percentage of viability of intestinal tissue explants cultured for 24, 48 or 72 hours ex vivo, and subsequently exposed to varying doses of Formic acid, formalin, or methanol.
Figure 12:
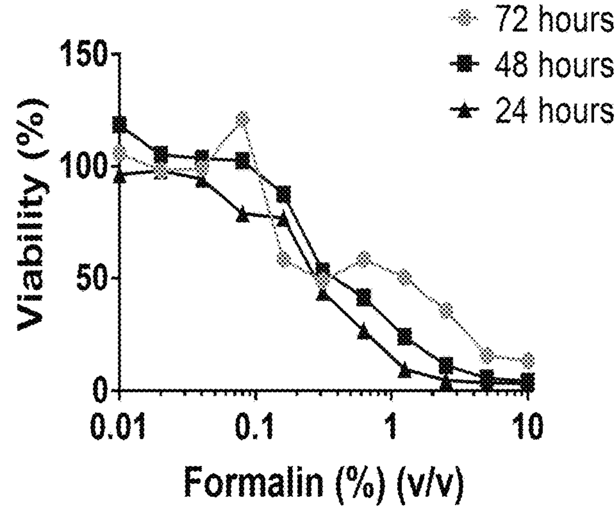
Figure 12:
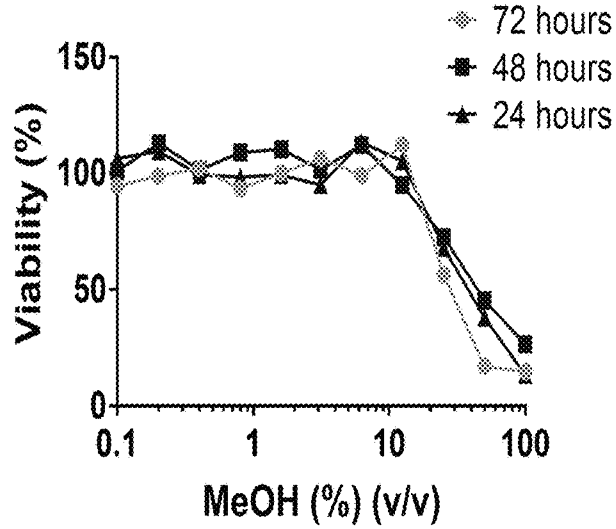
Figure 13:
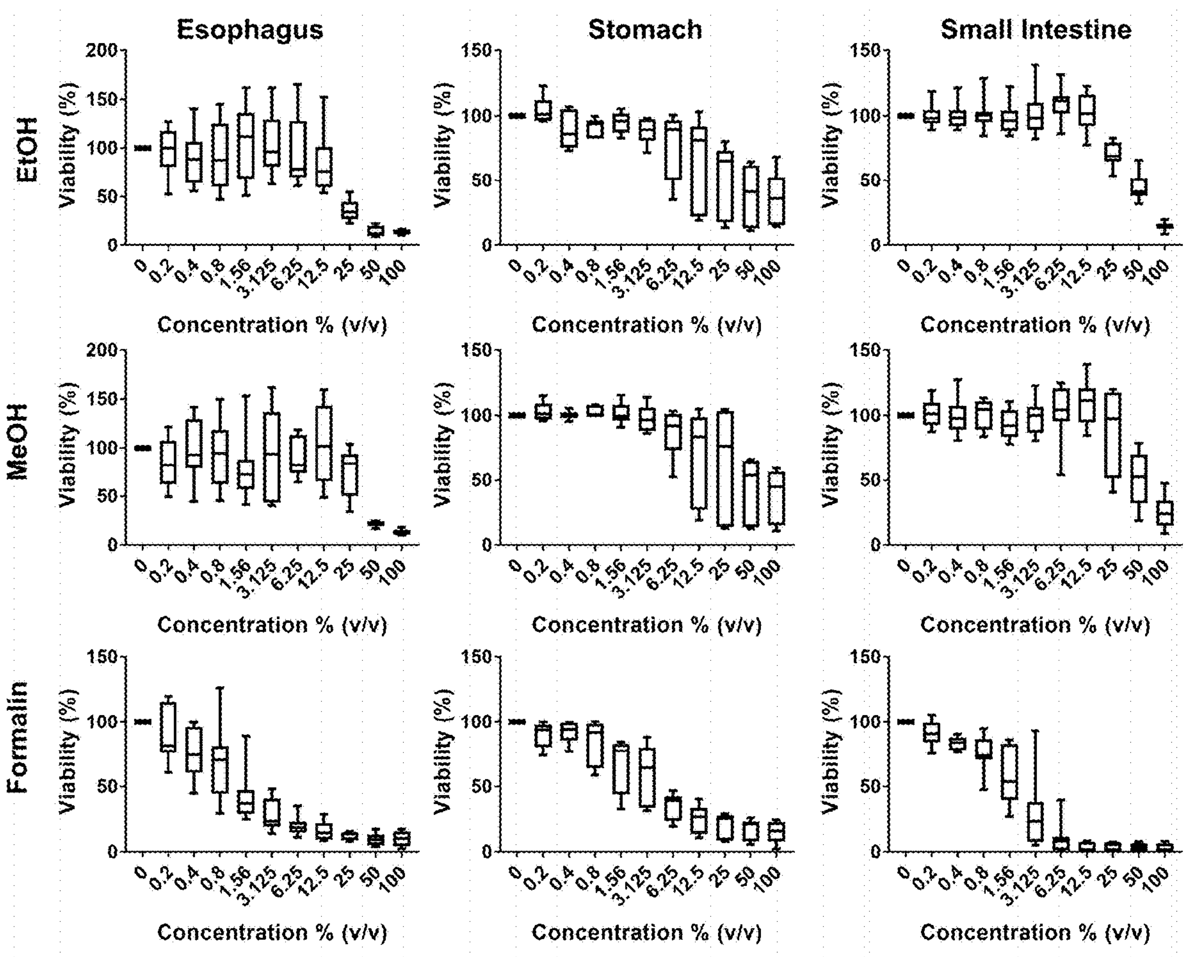
FIG. 13 provides graphs showing percentage of viability in tissue explants derived from the esophagus (left), stomach (middle) and small intestine (right) and treated with ethanol (top), methanol (middle) or formalin (bottom).

To determine responsiveness of the intestinal tissue explant to toxins, a resazurin-based viability analysis was conducted in various segments of the gastrointestinal tract after exposure to chemicals for a 24 hour time period. Resazurin is an oxidation-reduction indicator and established viability assay for mammalian cells. Resazurin is irreversibly reduced to the pink colored and highly red fluorescent resorufin in metabolizing cells. FIG. 12 shows a dose-dependent chemically induced decrease in intestinal tissue using tissue that was either freshly cultivated or cultured ex vivo for 24, 48, or 72 hours prior to the exposure. Interestingly, a recovery of the measured viability of the ex vivo cultured tissue explant after initial chemical exposure was observed (data not shown). FIG. 13 shows a dose-dependent chemically induced decrease in tissue viability of gastrointestinal tissue explants derived from either the esophagus, stomach or small intestine and treated with ethanol, methanol or formalin. Tissue was incubated in multiwell plates containing media in the receiver chamber and various chemicals at different concentrations in PBS in the donor chamber. After 24 hours viability was measured by resazurin-based viability analysis.

Figure 14:
FIG. 14 provides graphs showing the percentage of viability in intestinal tissue explants, or Log $IC_{50}$ values for cell lines, compared to drugs classified as having local gastrointestinal toxicity or no gastrointestinal toxicity.
Figure 14:
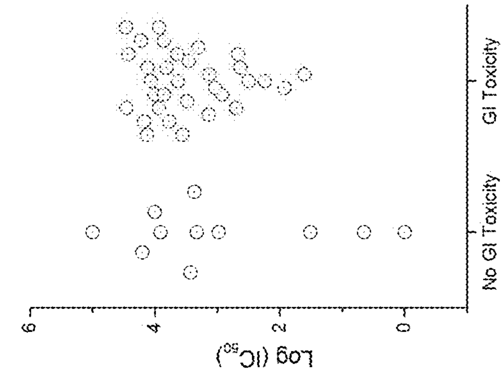
Figure 14:
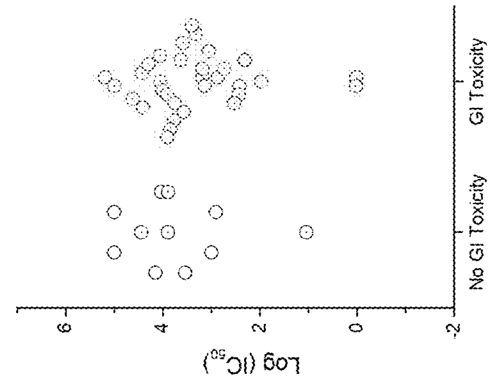
Figure 14:
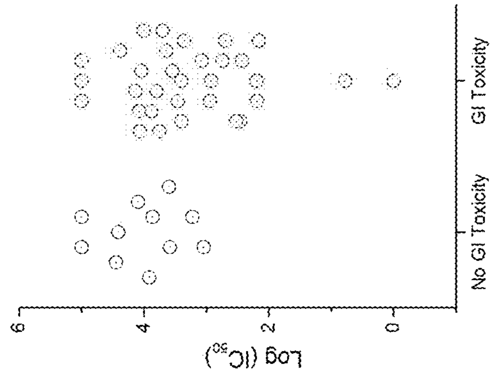
Figure 14:
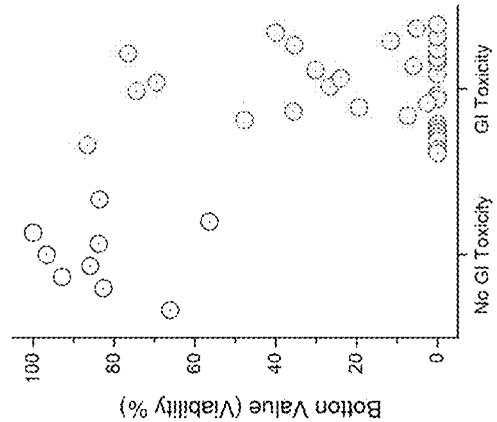

Once it was determined the tissue explant could detect drug induced toxicity, the correlation to local drug-induced gastrointestinal toxicity in humans was analyzed. Specifically, a systematic analysis of the reported side effects of all approved drugs was conducted. Based on this analysis, a panel of drugs clearly classified as having local gastrointestinal toxicity or no gastrointestinal side effects were tested. Dose-dependent viability assays with these drugs were assayed on the intestinal tissue explant, along with 3 different cell lines (HT29-MTX-E1; C2BBe1; HeLa) (FIG. 14). The comparison revealed little to no correlation between the cell based toxicity analysis and local gastrointestinal toxicity in humans.

Upon establishment that the intestinal tissue explant can predict local drug-induced gastrointestinal toxicity in humans, the system was used for a large-scale screening analysis to investigate if drug-induced local gastrointestinal toxicity of existing drugs can be modulated by excipient co-formulation. 15 orally administered drugs in use for a wide range of conditions and show local gastrointestinal side effects were used: antibiotics (cefpodoxime and doxycycline; NSAIDs (meloxicam, mesalamine, naproxen, indomethacin); bisphophanate (etidronate); bronchodilator (theophylline); antiviral (tenofovir and oseltamivir); vasodilator (tadalafil); diuretic (amiloride); and proton pump inhibitor (omeprazole). The drugs were co-formulated with a custom assembled compound library that were GRAS listed or used as inactive ingredients approved for oral administration. Drug-induced gastrointestinal toxicity was screened simultaneously while measuring drug absorption.

Formulation-dependent differences in local gastrointestinal drug toxicity were observed, and were found to be drug dependent (data not found). There was no clear correlation between changes in formulation-dependent viability and drug absorption, indicating changes in viability cannot solely be explained by altered drug perfusion (data not shown).

Figure 15:
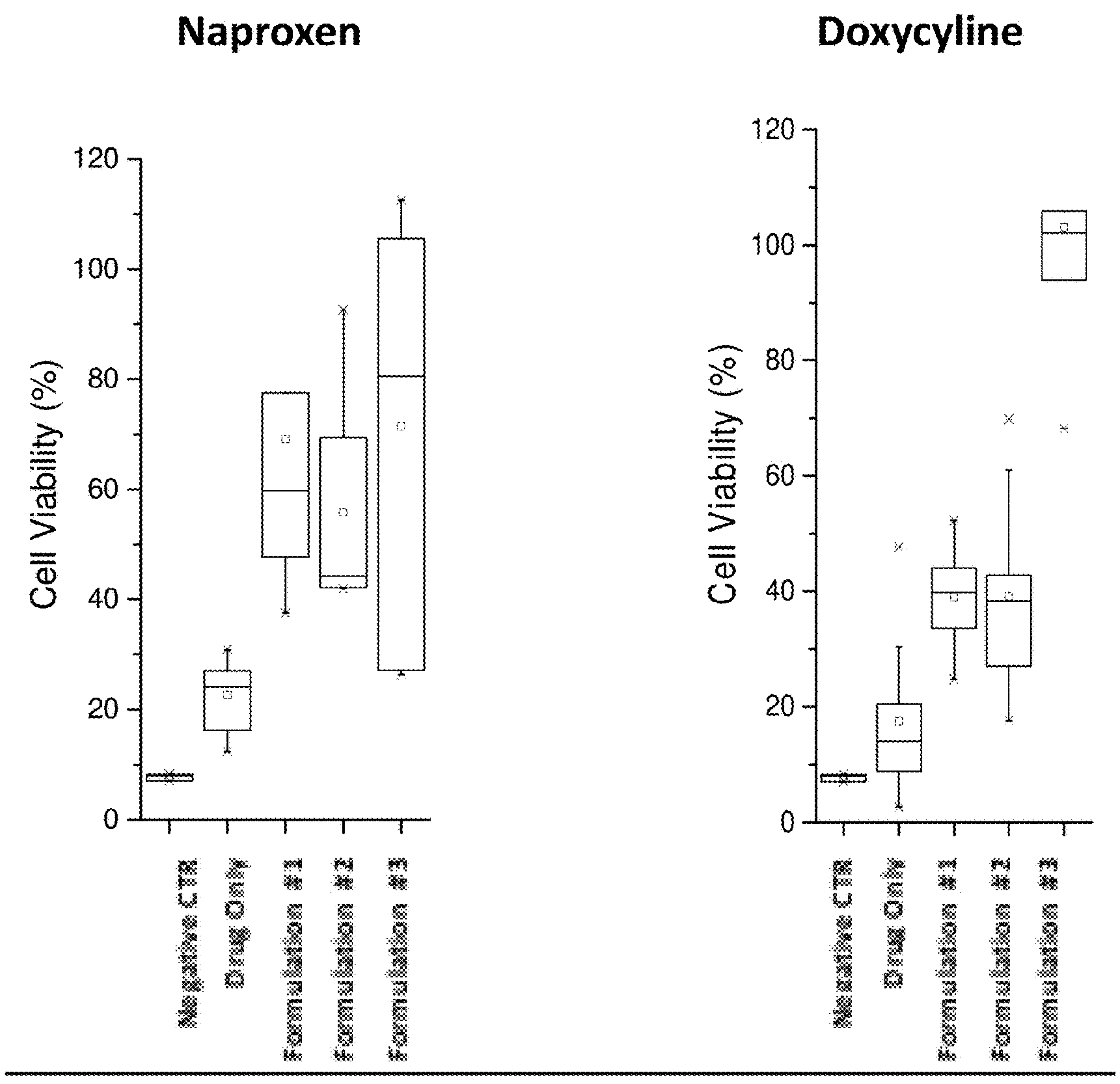
FIG. 15 provides graphs showing percentage of cell viability of intestinal tissue explants treated with naproxen (left) or doxycycline (right) formulated in three different formulations compared to drug alone and a negative control (100% ethanol).

Screening results for naproxen and doxycycline were validated in the intestinal tissue explant. FIG. 15 shows that three different formulations tested significantly improved viability compared to administration of the drug alone. Tissue viability was confirmed by immunobiological quantification of various cell toxicity markers (cleaved caspase 3, cleaved lamin A and phosphorylated histone H2B) as well as by pathological assessment by a pathologist.

Overall, these results indicated the intestinal tissue explant could accurately predict gastrointestinal toxicity in humans and be used to screen for formulations to reduce toxicity.

Example 10: Analysis of Tissue Explant on a Substrate

To analyze whether a tissue explant derived from a gastrointestinal tract of a large mammal is in planar contact with a substrate described herein, several methods can be employed.

Specifically, a solution containing a marker (e.g. dye) is added to the tissue explant in contact with a substrate to observe a uniform distribution of the marker across the tissue surface within the area contacted with the substrate. For example, the solution is added to the microwells of a substrate comprising the same. An aqueous solution containing a marker such as fluorophore or colored compound that readily stains the surface of the tissue explant enables detection on the surface of the tissue via photographic inspection, spectrophotometrically or via laser scanner based techniques. As an example, the fluorescent marker fluorescein at a concentration of 0.1 mg/ml in PBS can be used. Fluorescein solution is added to the tissue explant (e.g., within microwells of a substrate), incubated for 30 minutes, washed and subsequently analyzed spectrophotometrically and by using confocal microscopy. The tissue explant is considered to be in planar contact with the substrate if there is no significant difference in variability of the fluorescence signal within the area (e.g., microwell area) compared to an equivalent area of non-mounted tissue that was completely immersed in the fluorescein solution.

Alternatively, planar contact of the tissue explant with the substrate can be determined by coating the surface of the device with a marker (e.g. dye) to observe a uniform distribution (or pattern) of the marker on the tissue surface of the tissue area that is not within the area contacted by the substrate (e.g., within the microwells of a substrate comprising the same). Specifically, the entire area of the device facing the tissue is coated with a marker that forms a uniform layer on the surface of the device. This coating will stain tissue when placed in close contact. The resulting staining on the tissue remains intact once the device and tissue are separated and can subsequently be analyzed by visual inspection. As an example, the surface of the device is coated with a uniform layer of commercially available histology dyes such as CDI's Tissue Marking (Cancer Diagnostics Inc.). Then, the coated device is assembled with the tissue exactly how the device-tissue assembly is intended to be used. Afterwards, the device is separated from the tissue and the color markings on the tissue analyzed by photography. The tissue explant is in planar contact with the substrate if the tissue shows a regular pattern of markings across the entire tissue that correlate with the substrate set up (e.g., microwell set up).

The invention claimed is:

1. A high-throughput screening composition comprising:

(i) a first plate comprising a plurality of microwells;

(ii) a second plate comprising a plurality of microwells, wherein the number of microwells of the second plate matches the number of microwells of the first plate; and (iii) an isolated tissue explant from a large, non-human, mammalian gastrointestinal tract comprising a luminal surface and a basolateral surface that is placed in between the first plate and the second plate, wherein the luminal surface of the tissue explant is in planar contact with more than one microwell of the first plate and the basolaterial surface of the tissue explant is in planar contact with more than one microwell of the second plate, wherein each of the plurality of microwells of the first plate is a through hole that facilitates contact of a test compound with the luminal surface of the tissue explant, and wherein each of the plurality of microwells of the second plate is a receiver chamber capable of containing media that receives the test compound at the basolateral surface of the tissue explant;

wherein the second plate comprises a solid surface separating each microwell of the plurality of microwells, and wherein the solid surface of the second plate is in planar contact with non-microwell areas of the basolateral surface of the tissue explant; and wherein the first and second plates apply pressure to non-microwell areas of the tissue explant to minimize well-to-well leakage.

2. The composition of claim 1, wherein the receiver chambers of the second plate contain media.

3. The composition of claim 1, wherein the tissue explant is incubated in media contained in the receiver chambers of the second plate.

4. The composition of claim 1, wherein the tissue explant comprises small intestine epithelium.

5. The composition of claim 1, wherein the tissue explant is derived from ileum, jejunum, or duodenum of the gastrointestinal tract.

6. The composition of claim 1, wherein the tissue explant comprises a circular muscular layer and intestinal villi.

7. The composition of claim 1, wherein the gastrointestinal tract is a porcine gastrointestinal tract.

8. The composition of claim 1, wherein the tissue explant comprises an intact extracellular matrix.

9. The composition of claim 1, wherein the first plate and the second plate further comprise an aperture for receiving and mounting a fastener therein.

10. The composition of claim 9, wherein the fastener is a screw or a magnet.

11. The composition of claim 1, wherein the first plate and the second plate each comprise 6, 12, 24, 48, 96, 384 or 1536 microwells.

12. The composition of claim 1, wherein the tissue explant comprises intact crypts.

13. The composition of claim 1, wherein the tissue explant comprises at least one drug transporter.

14. The composition of claim 1, wherein the tissue explant comprises at least one metabolizing enzyme.

15. A high-throughput screening composition comprising:

(i) a first plate comprising a plurality of microwells;

(ii) a second plate comprising a plurality of microwells, wherein the number of microwells of the second plate matches the number of microwells of the first plate; and (iii) an isolated tissue explant from a large, non-human, mammalian gastrointestinal tract comprising a luminal surface and a basolateral surface that is placed in between the first plate and the second plate, wherein the luminal surface of the tissue explant is in planar contact with more than one microwell of the first plate and the basolateral surface of the tissue explant is in planar contact with more than one microwell of the second plate, wherein each of the plurality of microwells of the first plate is a through hole that facilitates contact of a test compound with the luminal surface of the tissue explant;

wherein each of the plurality of microwells of the second plate is a through hole;

wherein the first and second plates are mounted to a third plate comprising a plurality of microwells, wherein the number of microwells of the third plate matches the number of microwells of the first plate and the second plate; wherein each of the plurality of microwells of the third plate is a receiver chamber capable of containing media that receives the test compound at the basolaterial surface of the tissue explant;

wherein the second plate comprises a solid surface separating each microwell of the plurality of microwells, and wherein the solid surface of the second plate is in planar contact with non-microwell areas of the basolateral surface of the tissue explant; and wherein the first and second plates apply pressure to non-microwell areas of the tissue explant to minimize well-to-well leakage.

16. The composition of claim 15, wherein the receiver chambers of the third plate contain media.

17. The composition of claim 15, wherein the tissue explant is incubated in media contained in the receiver chambers of the third plate.

18. The composition of claim 15, wherein the tissue explant comprises small intestine epithelium.

19. The composition of claim 15, wherein the tissue explant is derived from ileum, jejunum, or duodenum of the gastrointestinal tract.

20. The composition of claim 15, wherein the tissue explant comprises a circular muscular layer and intestinal villi.

21. The composition of claim 15, wherein the gastrointestinal tract is a porcine gastrointestinal tract.

22. The composition of claim 15, wherein the tissue explant comprises an intact extracellular matrix.

23. The composition of claim 15, wherein the first plate and the second plate further comprise an aperture for receiving and mounting a fastener therein.

24. The composition of claim 23, wherein the fastener is a screw or a magnet.

25. The composition of claim 15, wherein the first plate and the second plate each comprise 6, 12, 24, 48, 96, 384 or 1536 microwells.

26. The composition of claim 15, wherein the tissue explant comprises intact crypts.

27. The composition of claim 15, wherein the tissue explant comprises at least one drug transporter.

28. The composition of claim 15, wherein the tissue explant comprises at least one metabolizing enzyme.

* * * * *